(12) United States Patent
Nakabe et al.

(10) Patent No.: US 12,727,936 B2
(45) Date of Patent: Sep. 8, 2026

(54) ELECTRODE UNIT, TREATMENT SYSTEM AND METHOD FOR OPERATING ELECTRODE UNIT

(71) Applicant: OLYMPUS CORPORATION, Tokyo (JP)

(72) Inventors: Kazuya Nakabe, Tokyo (JP); Soichi Ikuma, Tokyo (JP); Nagahide Sakai, Tokyo (JP); Shogo Matsumoto, Chofu (JP); Toshifumi Katsuragi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 879 days.

(21) Appl. No.: 17/941,113

(22) Filed: Sep. 9, 2022

(65) Prior Publication Data

US 2023/0000541 A1 Jan. 5, 2023

Related U.S. Application Data

(63) Continuation of application No. PCT/JP2020/010476, filed on Mar. 11, 2020.

(51) Int. Cl.
*A61B 18/14* (2006.01)
*A61B 18/12* (2006.01)

(52) U.S. Cl.
CPC ........ *A61B 18/149* (2013.01); *A61B 18/1206* (2013.01); *A61B 2018/126* (2013.01)

(58) Field of Classification Search
CPC ...... A61B 2018/126; A61B 2018/1422; A61B 2018/1432; A61B 2018/1475; A61B 18/1206; A61B 18/149
See application file for complete search history.

(56) References Cited

U.S. PATENT DOCUMENTS 5,443,463 A * 8/1995 Stern ........................ A61N 1/06 606/51
5,582,610 A * 12/1996 Grossi .................. A61B 18/149 606/41

(Continued)

FOREIGN PATENT DOCUMENTS

CN 101035478 A 9/2007
CN 106413598 A 2/2017

(Continued)

OTHER PUBLICATIONS

International Search Report dated Apr. 21, 2020 issued in PCT/JP2020/010476.

*Primary Examiner* — Michael F Peffley
*Assistant Examiner* — Samantha M Good
(74) *Attorney, Agent, or Firm* — Scully, Scott, Murphy & Presser, P.C.

(57) ABSTRACT

An electrode unit of the invention includes: an electrode including one end and another end, the other end including a free end; and an electrode supporting portion that supports the one end of the electrode. The electrode is disposed in a second plane that is different from a first plane in which the electrode supporting portion is moved to advance or withdraw when the electrode supporting portion is moved to advance or withdraw in a direction along a longitudinal axis of the electrode supporting portion, and the electrode is supported by the electrode supporting portion via a flexed portion projecting from the first plane to the second plane.

15 Claims, 31 Drawing Sheets

(56) References Cited

U.S. PATENT DOCUMENTS

| | | | | |
|---|---|---|---|---|
| 2007/0066976 | A1 | 3/2007 | Hayashida et al. | |
| 2007/0270797 | A1 * | 11/2007 | Lu | A61B 18/1492 606/50 |
| 2009/0043303 | A1 * | 2/2009 | Shimomura | A61B 18/149 606/46 |
| 2012/0059219 | A1 * | 3/2012 | St. George | A61B 18/149 600/105 |
| 2017/0042522 | A1 | 2/2017 | Kogiso | |
| 2017/0119426 | A1 | 5/2017 | Akagane | |
| 2017/0360501 | A1 * | 12/2017 | Branovan | A61B 18/1206 |
| 2018/0193092 | A1 * | 7/2018 | Gearheart | A61B 18/1206 |

FOREIGN PATENT DOCUMENTS

| | | | |
|---|---|---|---|
| EP | 3138462 | A1 | 3/2017 |
| JP | H09-84804 | A | 3/1997 |
| JP | 3730796 | B2 | 1/2006 |
| JP | 2009119218 | A | 6/2009 |
| JP | 4495493 | B2 | 7/2010 |
| JP | 2010220886 | A | 10/2010 |
| JP | 2012050758 | A | 3/2012 |
| JP | 2012-081055 | A | 4/2012 |
| WO | 2015166980 | A1 | 11/2015 |

* cited by examiner

ELECTRODE UNIT, TREATMENT SYSTEM AND METHOD FOR OPERATING ELECTRODE UNIT

CROSS REFERENCE TO RELATED APPLICATION

This application is a continuation application of PCT/JP2020/010476 filed on Mar. 11, 2020, the entire contents of which are incorporated herein by this reference.

BACKGROUND OF THE INVENTION

1. Field of the Invention

The present invention relates to an electrode unit, a treatment system and a method for operating the electrode unit, and more specifically relates to an electrode unit for treating a tissue inside a body cavity using a high-frequency electric current, a treatment system and a method for operating the electrode unit.

2. Description of the Related Art

Conventionally, in the medical field, endoscope systems, which are medical apparatuses for, under endoscopic observation, performing treatment, for example, resection or coagulation of a living tissue inside a body cavity of a subject such as a human body, using an energy device, such as an electric surgical knife, that uses a high-frequency electric current, have been publicly known. Endoscope systems including this type of energy device have widely been used when treatment, for example, resection of a living tissue inside an organ such as a bladder, is performed.

For example, Japanese Patent Nos. 4495493 and 3730796 each disclose an endoscope system in which under endoscopic observation, a living tissue inside a body cavity of a subject is subjected to treatment such as resection or coagulation using an energy device that uses a high-frequency electric current.

The endoscope system disclosed in Japanese Patent No. 4495493 includes an electrode unit that includes an electrode formed in a hook-shaped shape, and performs treatment, such as resection or coagulation of a desired living tissue, by making a high-frequency electric current flow in the hook-shaped electrode. The hook-shaped electrode disclosed in Japanese Patent No. 4495493 is configured to be capable of being arbitrarily set in two states, a state in which the electrode is rotatable relative to a sheath around an axis of the sheath with an entirety of the electrode projecting from a distal end of the sheath and a rotation-restricted state in which the electrode is restricted from rotating relative to the sheath around the axis of the sheath with only an arbitrary length of the electrode projecting from the distal end of the sheath.

This configuration enables the endoscope system disclosed in Japanese Patent No. 4495493 to during treatment such as resection of a living tissue, restrict rotation of the hook-shaped electrode around the sheath axis and hold the electrode in a stable posture. Therefore, the configuration enables a user to more stably perform a desired operation.

SUMMARY OF THE INVENTION

An electrode unit according to an aspect of the present invention includes: an electrode including one end and another end, the other end including a free end; and an electrode supporting portion that supports the one end of the electrode. The electrode is disposed in a second plane that is different from a first plane in which the electrode supporting portion is moved to advance or withdraw when the electrode supporting portion is moved to advance or withdraw in a direction along a longitudinal axis of the electrode supporting portion, and the electrode is supported by the electrode supporting portion via a flexed portion projecting from the first plane to the second plane.

A treatment system according to an aspect of the present invention includes: an endoscope including an insertion portion; and an electrode unit that projects from a distal end of the insertion portion, the electrode unit being configured to treat a tissue. The electrode unit includes an electrode including one end and another end, the other end including a free end, and an electrode supporting portion that supports the one end of the electrode, the electrode is disposed in a second plane that is different from a first plane in which the electrode supporting portion is moved to advance or withdraw when the electrode supporting portion is moved to advance or withdraw in a direction along a longitudinal axis of the electrode supporting portion, and the electrode is supported by the electrode supporting portion via a flexed portion projecting from the first plane to the second plane.

A method for operating an electrode unit according to an aspect of the present invention is a method for operating an electrode unit for treating a tissue inside a body cavity using a high-frequency electric current, the method including: creating a detached fragment, a part of the detached fragment sticking to an inside of the body cavity, via an electrode; applying the electrode to the part of the detached fragment, the part sticking to the inside of the body cavity, with an electrode supporting portion disposed under the detached fragment, the electrode supporting portion supporting the electrode; providing energy to the electrode to create the detached fragment, a part of the detached fragment sticking to the inside of the body cavity; applying the electrode to the part of the detached fragment, the part sticking to the inside of the body cavity, with a part of the electrode unit disposed under the detached fragment; and providing energy to the electrode to separate the detached fragment off from the inside of the body cavity.

BRIEF DESCRIPTION OF THE DRAWINGS

FIG. 46 is a schematic diagram illustrating a section along a line [46]-[46] in

FIG. 45;

DETAILED DESCRIPTION OF THE PREFERRED EMBODIMENTS

Figure 1:
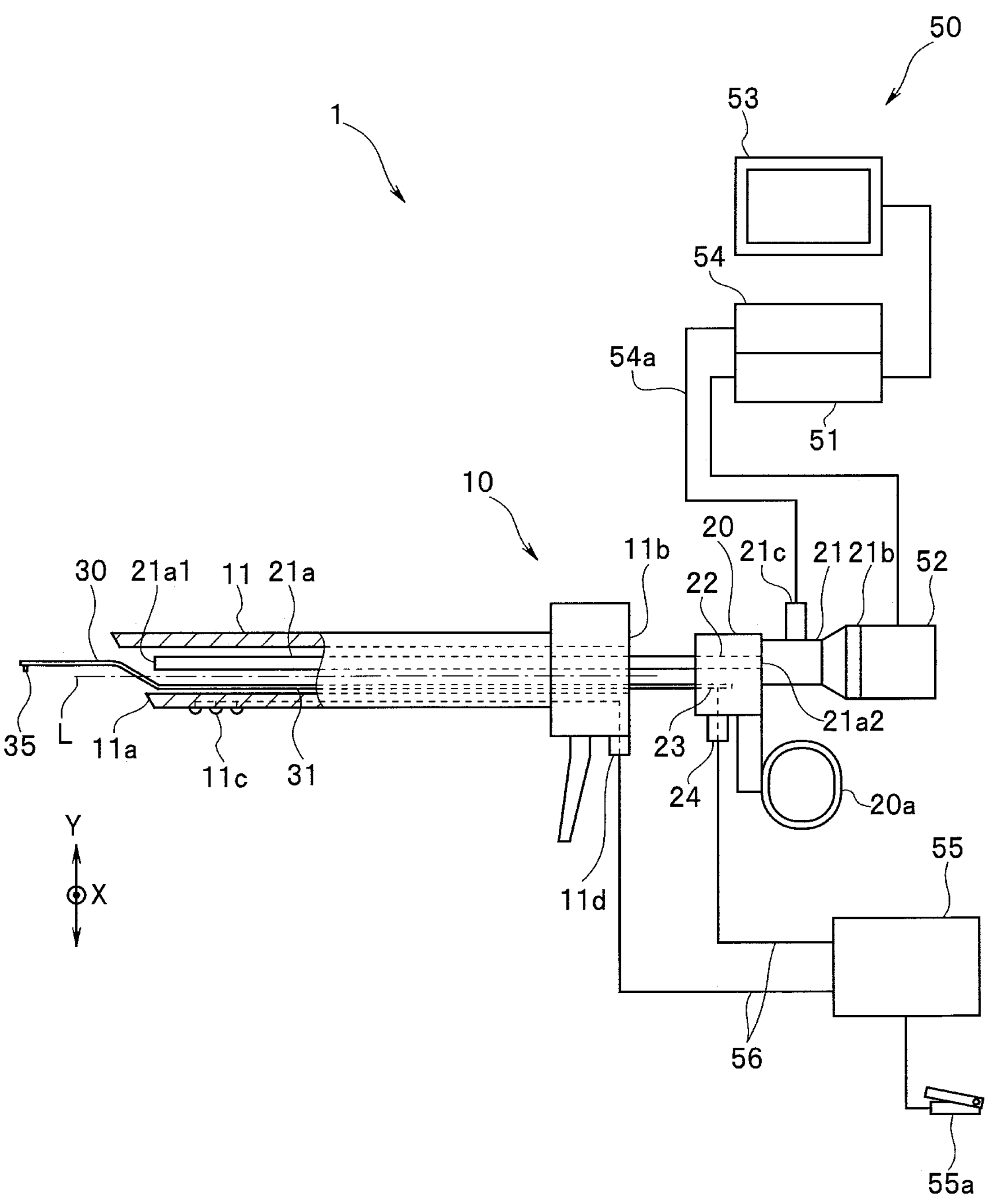
FIG. 1 is a schematic diagram illustrating a configuration of an endoscope system including an electrode unit of a first embodiment of the present invention.

Generally, in conventional endoscope systems of a type that includes an electrode unit including a hook-shaped electrode, in order to resect a desired lesion region in one piece, for example, it is necessary to successively perform a plurality of different operations such as an operation of marking the periphery of the lesion region, an operation of dissecting the periphery of the lesion region and an operation of detaching the dissected region, which requires complicated handling and thus is problematic in requiring much skill.

Furthermore, in the aforementioned endoscope system disclosed in Japanese Patent No. 4495493, even enhancement in ease of handing is achieved by preventing rotation of the electrode during a procedure, no control in depth direction in which the electrode penetrates from a wall surface of a living tissue is considered, which may cause unevenness in thickness of the resected living tissue.

Generally, in a case where a resected living tissue is used for a biopsy, the tissue needs to have a predetermined thickness, and thus, it is considered preferable that a thickness of the resected tissue, that is, a resection depth be constant.

On the other hand, the apparatus disclosed in Japanese Patent No. 3730796 includes an electrode unit that includes an electrode formed in a looped shape, and performs treatment, such as resection or coagulation of a living tissue, by making a high-frequency electric current flow in the looped electrode. The looped electrode-type electrode unit is advantageous in ease of handling.

However, in conventional endoscope systems of the type that includes an electrode unit including a looped electrode, a dimension in a width direction of the electrode is restricted by, e.g., a diameter of a sheath that allows insertion of the electrode, or a diameter of a channel of an endoscope, the channel allowing insertion of the sheath, and thus, a resection width narrows, causing the problem of impossibility of performing one-piece resection of a desired lesion region.

Generally, a size of an electrode, the size allowing the electrode to be inserted through a device channel of, e.g., a resectoscope or a cystoscope, is less than 1 cm. On the other hand, in ordinary cases, a living tissue desired to be resected in one piece is around 4 cm at a maximum.

Therefore, the present invention enables provision of an electrode unit that performs treatment of a tissue inside a body cavity using a high-frequency electric current, the electrode unit having a structure that enables one-piece resection of a living tissue inside a body cavity to be performed easily, and a method for operating the electrode unit.

The present invention will be described below based on embodiments illustrated in the drawings. Each of the drawings used for the below description is a schematic one, and in order to illustrate respective components in sizes that are large enough to be recognized in the drawings, the components may be illustrated so as to be different in, e.g., dimensional relationship among respective members and scale. Therefore, the present invention is not limited to the illustrated forms in terms of, e.g., counts of the respective components, shapes of the respective components, ratios in size among the respective components and relative positional relationships among the respective components indicated in each drawing.

First Embodiment

An endoscope system including an electrode unit of a first embodiment of the present invention is a medical apparatus for under endoscopic observation, performing desired treatment such as resection or coagulation of a living tissue inside a subject.

Therefore, before detailed description of the electrode unit of the first embodiment of the present invention, first, a schematic configuration of the entire endoscope system including the electrode unit of the present embodiment will be described below with reference to FIG. 1.

FIG. 1 is a diagram schematically illustrating a configuration of an endoscope system including an electrode unit of the first embodiment of the present invention.

As illustrated in FIG. 1, an endoscope system 1 including an electrode unit 30 of the present embodiment includes, e.g., a resectoscope 10, which is an endoscope, the electrode unit 30 of the present embodiment and an external apparatus 50.

The endoscope system 1 includes the electrode unit 30 of the present embodiment is an example of an endoscope system in which a subject is a human body. Furthermore, in the endoscope system 1 in the example configuration in FIG. 1, an endoscope of a form generally called a resectoscope is employed. However, the electrode unit of the present invention is not limited to this example configuration and can also be applied to, for example, a flexible endoscope.

In the endoscope system 1 including the electrode unit 30 of the present embodiment, the resectoscope 10 includes, e.g., a sheath 11, a slider 20 and a telescope 21.

The sheath 11 is formed in a straight shape along a longitudinal axis L and is formed of a hollow tubular member. Opposite ends in a direction along the longitudinal axis L of the sheath 11 are open. The sheath 11 is a part that is inserted into a subject from the outside of the subject when the resectoscope 10 is used. When the resectoscope 10 is used, the telescope 21 and the electrode unit 30 are inserted into the sheath 11.

On an outer circumference of the sheath 11, an outer sheath for introducing a perfusate into a subject is disposed. A configuration of an outer sheath or the like provided for introducing a perfusate into a subject is publicly known, and thus, description of such configuration will be omitted. In the present embodiment, the perfusate is, for example, an electrolyte solution having electrical conductivity, such as saline.

Of the opposite ends in the direction along the longitudinal axis L of the sheath 11, one end on the side that is inserted into a subject is referred to "distal end 11*a*" and the other end on the opposite side from the distal end 11*a* is referred to as "proximal end 11*b*". The proximal end 11*b* of the sheath 11 is a part disposed outside the subject when the resectoscope 10 is used.

Figure 3:
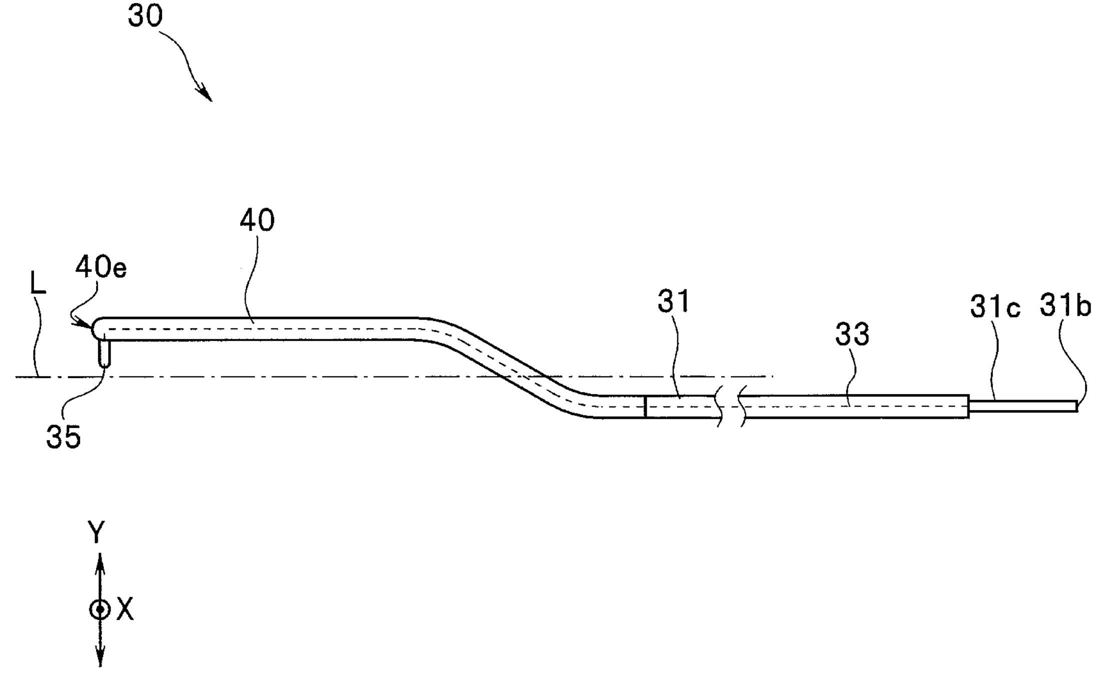
FIG. 3 is a left side view in a direction of arrow [3] in FIG. 2.

Here, a first axis X and a second axis Y that are a pair of axes orthogonal to the longitudinal axis L and orthogonal to each other are set. Furthermore, it is assumed that: one of directions along the first axis X is a rightward direction; and the other is a leftward direction. In this case, it is assumed that: the right side as the distal end side (far end side) is viewed from the proximal end side is the rightward direction; and the left side as the distal end side (far end side) is viewed from the proximal end side is the leftward direction (FIG. 3). Furthermore, it is assumed that one of directions along the second axis Y is an upward direction; and the other is a downward direction.

In this case, in an image picked up using the telescope 21, a horizontal direction of the image is substantially parallel to the first axis X and a vertical direction is substantially parallel to the second axis Y. Furthermore, the upward direction and the downward direction on the second axis Y of the image correspond to the upper side and the lower side of the image in the image picked up using the telescope 21.

In at least a surface in the vicinity of the distal end 11*a* of the sheath 11, a collection electrode 11*c* including an electrically conductive material is provided so as to be exposed to the outside.

The entire sheath 11 includes an electrically conductive material such as a metal. Accordingly, instead of provision of the collection electrode 11*c*, the sheath 11 may be configured such that an entire surface of the sheath 11 functions as a collection electrode.

In the vicinity of the proximal end 11*b* of the sheath 11, a sheath connector 11*d* is provided. The sheath connector 11*d* is electrically connected to the collection electrode 11*c*. A cable 56 is connected to the sheath connector 11*d*. The cable 56 electrically connects the sheath connector 11*d* and a high-frequency power supply control device 55 (which will be described later) included in the external apparatus 50.

The slider 20 is an operation member disposed on the proximal end 11*b* side of the sheath 11. The slider 20 is configured to move so as to be capable of advancing/withdrawing relative to the sheath 11 in the direction along the longitudinal axis L. A handle 20*a* is provided at the slider 20. A user applying an amount of force in the direction along the longitudinal axis L to the handle 20*a* with, e.g., his/her fingers makes the slider 20 move so as to advance/withdraw relative to the sheath 11 in the direction along the longitudinal axis L.

For a mechanism for guiding the slider 20 such that the slider 20 is movable relative to the sheath 11, a configuration that is substantially the same as a configuration of a conventional resectoscope is employed. Therefore, detailed illustration and description of the mechanism (mechanism of advancing/withdrawing movement of the slider 20) will be omitted.

The slider 20 includes, e.g., a scope holding portion 22, an electrode unit holding portion 23 and an electrode connector 24. Here, the scope holding portion 22 is a component portion provided to hold the telescope 21.

The telescope 21 is a component unit for optically observing the inside of the subject. The telescope 21 is a component unit including, e.g., an elongated insertion portion 21*a*, an eyepiece portion 21*b* and a light source connection portion 21*c*.

The insertion portion 21*a* is a component portion that is inserted into the sheath 11 when the telescope 21 is fixed in the scope holding portion 22.

In a distal end portion 21*a*1 of the insertion portion 21*a*, an observation window, an illuminating light output window, etc., which are not illustrated, are arranged. Furthermore, in a proximal end portion 21*a*2 of the insertion portion 21*a*, e.g., the eyepiece portion 21*b* and the light source connection portion 21*c* of the telescope 21 are arranged.

An image pickup unit 52 included in the external apparatus 50 is fitted to the eyepiece portion 21*b*. The image pickup unit 52 is electrically connected to a video processor 51 included in the external apparatus 50. An image display device 53 included in the external apparatus 50 is electrically connected to the video processor 51.

Furthermore, one end of an optical fiber cable 54*a* is connected to the light source connection portion 21*c*. The other end of the optical fiber cable 54*a* is connected to a light source device 54 included in the external apparatus 50.

An image of light from a subject, the light entering the observation window provided in the distal end portion 21*a*1 of the insertion portion 21*a*, is picked up by the image pickup unit 52, and as a result, an image based on image data generated by the image pickup unit 52 is displayed in a form in which the image can be viewed via the image display device 53.

Furthermore, illuminating light emitted from the light source device 54 is outputted toward the subject from the illuminating light output window provided in the distal end portion 21*a*1 of the insertion portion 21*a*.

It is assumed that respective configurations of the telescope 21 and the external apparatus 50 (the video processor 51, the image pickup unit 52, the image display device 53, the light source device 54, etc.) connected to the telescope 21 are substantially the same as respective configurations in a conventional resectoscope 10. Therefore, detailed description of the respective devices will be omitted.

In the slider 20, the electrode unit holding portion 23 is a component portion provided to hold the electrode unit 30 of the present embodiment. Furthermore, the electrode connector 24 is electrically connected to a proximal end portion of the electrode unit 30. One end of the cable 56 is connected to the electrode connector 24. The other end of the cable 56 is electrically connected to the high-frequency power supply control device 55 of the external apparatus 50. Consequently, the electrode connector 24 and the cable 56 are interposed between the electrode unit 30 and the high-frequency power supply control device 55, ensuring electrical connection.

Although in the present embodiment, a form in which the electrode connector 24 is configurated separately from the sheath connector 11*d* is indicated as an example, the present invention is not limited to the example configuration. For example, a form configured by forming an electrode connector 24 and a sheath connector 11*d* integrally may be employed.

The proximal end portion of the electrode unit 30 of the present embodiment is fixed in the electrode unit holding portion 23, and the rest of the electrode unit 30 is disposed so as to be inserted through a device channel (not illustrated) inside the sheath 11.

Here, as described above, the slider 20 is configured to be capable of moving so as to advance/withdraw relative to the sheath 11 in the direction along the longitudinal axis L together with the telescope 21 and the electrode unit 30.

Therefore, when the slider 20 is moved so as to advance/withdraw relative to the sheath 11 in the direction along the longitudinal axis L, a part on the distal end side of the electrode unit 30 projects outward from the distal end 11*a* of the sheath 11. A later-described electrode 35 is arranged in a part of the electrode unit 30, the part projecting from the distal end 11*a* of the sheath 11.

The electrode unit 30, the collection electrode 11*c* and the high-frequency power supply control device 55 configure what is called a bipolar electrosurgical apparatus. The electrosurgical apparatus is not limited to a bipolar electrosurgical apparatus and may be a monopolar electrosurgical apparatus.

Here, the high-frequency power supply control device 55 includes a switch 55*a*. The switch 55*a* is a component unit including a switch member for performing an operation to turn on/off the high-frequency power supply control device 55. For a specific example configuration of the switch 55*a*, for example, what is called a foot switch configured to allow an operation to turn on/off the switch member to be performed by the user pushing the switch 55*a* with his/her foot is employed. The high-frequency power supply control device 55 switches between output and non-output of a high-frequency electric current in response to the operation to turn on/off the switch 55*a*.

The high-frequency electric current outputted from the high-frequency power supply control device 55 flows in the electrode 35, the perfusate and the collection electrode 11*c* inside the subject. If the electrode 35 is brought into contact with a living tissue of the subject in a state in which the high-frequency power supply control device 55 is outputting the high-frequency electric current, the living tissue generates heat. In this way, the electrode 35 is configured to be capable of performing desired treatment such as resection or coagulation of a living tissue.

The schematic configuration of the endoscope system 1 including the electrode unit 30 of the present embodiment has been described above. Detailed description of the rest of the configuration of the endoscope system 1 will be omitted because the rest of the configuration of the endoscope system 1 is similar in the configuration of a conventional endoscope system of a same type.

Next, a configuration of the electrode unit 30 of the present embodiment will be described in detail below.

The electrode unit 30 of the present embodiment is a high-frequency energy device that subjects a living tissue inside a body cavity of a subject to desired treatment using a high-frequency electric current. The electrode unit 30 is used by making the slider 20, which is an operation member provided on the proximal end side, advance/withdraw relative to the sheath 11 in the direction along the longitudinal axis L in a state in which the electrode unit 30 is inserted through, e.g., the device channel (not illustrated; see sign 10*a* in FIG. 8 referred to later) of the resectoscope 10 or an instrument channel of an endoscope.

Figure 2:
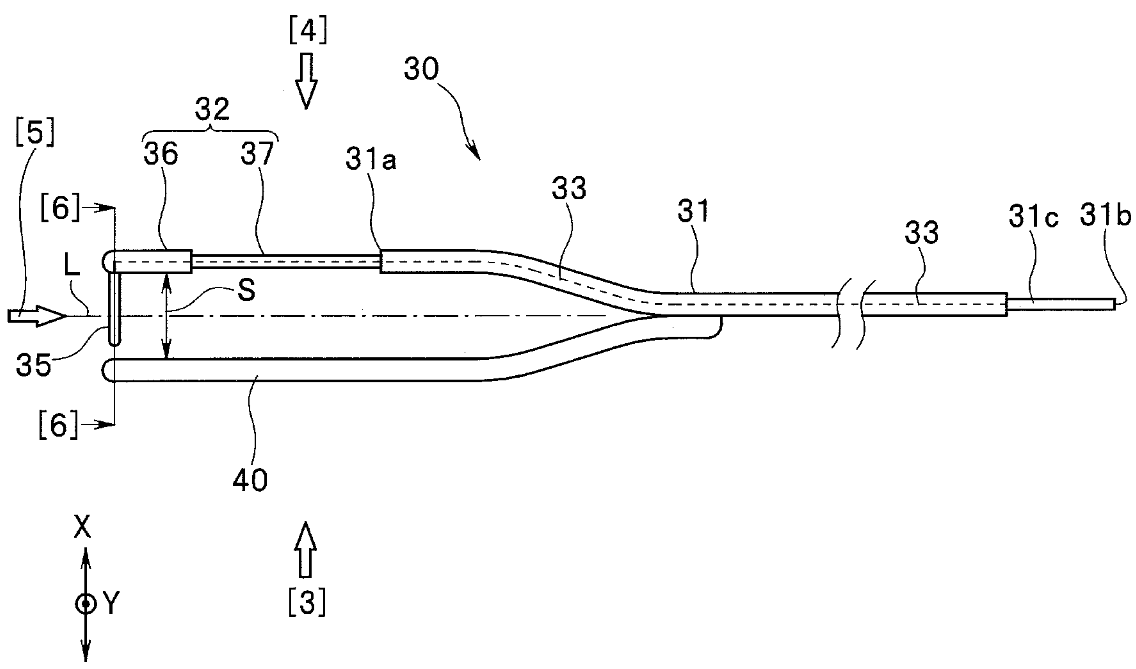
FIG. 2 is a plan view of the electrode unit of the first embodiment of the present invention from an upper side.

Here, FIGS. 2 to 8 are diagrams each illustrating the electrode unit of the present embodiment. Of the figures, FIG. 2 is a plan view of the electrode unit of the present embodiment from the upper side. Here, it is assumed that: the upper side of the figure in a direction along the first axis X in FIG. 2 is referred to as a rightward direction of the electrode unit; and the lower side of the figure in the direction along the first axis X in FIG. 2 is referred to as a leftward direction of the electrode unit.

Figure 4:
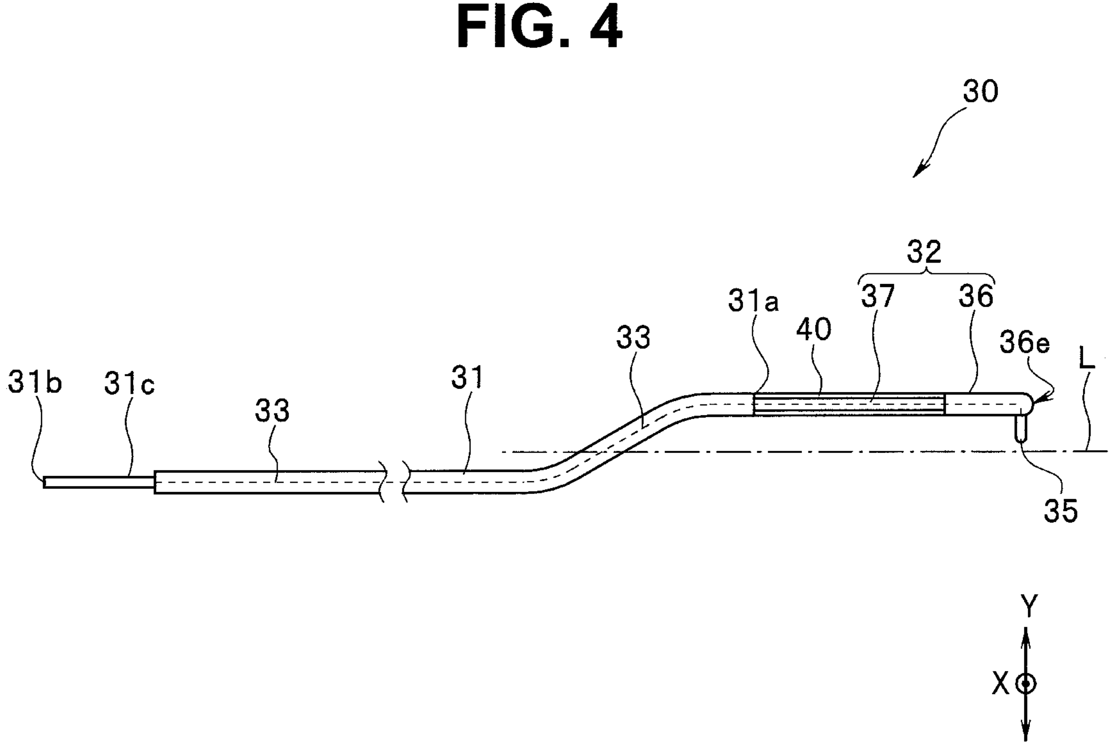
FIG. 4 is a right side view in a direction of arrow [4] in FIG. 2.

FIG. 3 is a left side view of the electrode unit of the present embodiment. In other words, FIG. 3 is a diagram as viewed in a direction of arrow [3] in FIG. 2. FIG. 4 is a right side view of the electrode unit of the present embodiment. In other words, FIG. 4 is a diagram as viewed in a direction of arrow [4] in FIG. 2. Here, it is assumed that: the upper side of the figure in a direction along the second axis Y in each of FIGS. 3 and 4 is referred to as an upward direction of the electrode unit; and the lower side of the figure in the direction along the second axis Y in each of FIGS. 3 and 4 is referred to as a downward direction of the electrode unit.

Figure 5:
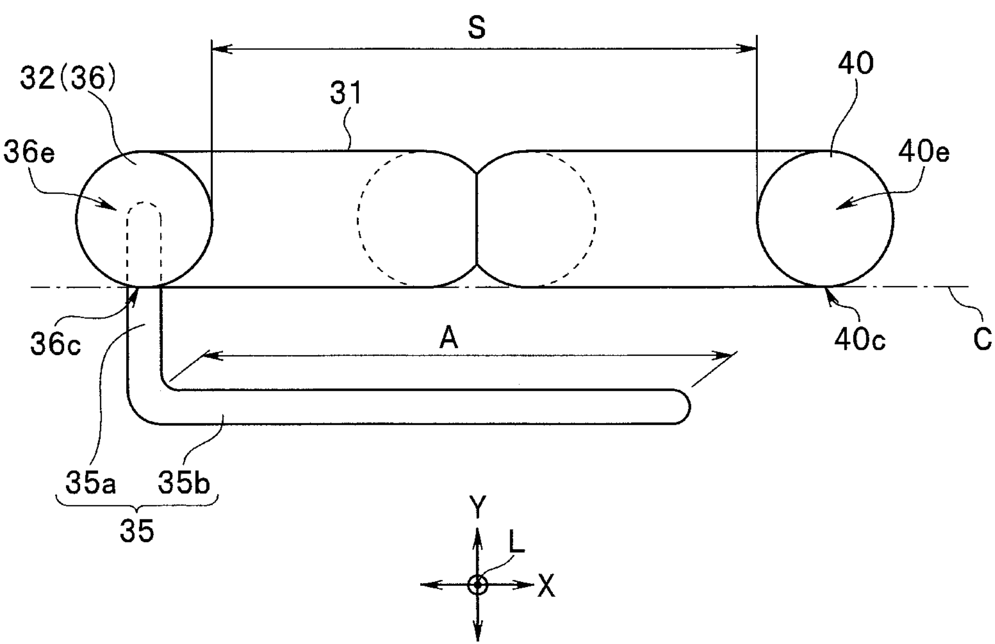
FIG. 5 is a front view in a direction of arrow [5] in FIG. 2.
Figure 6:
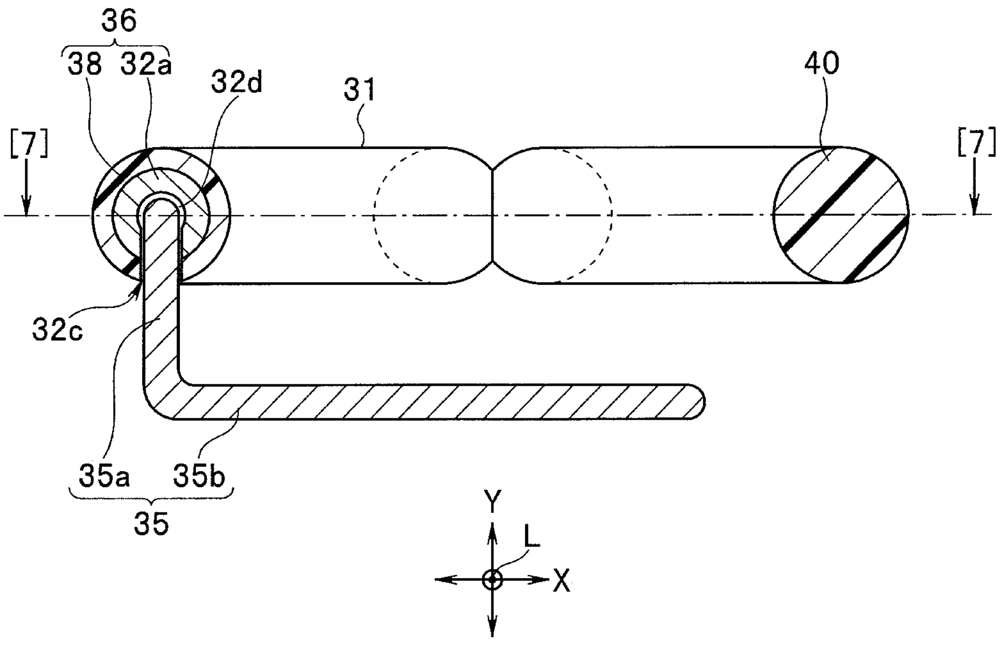
FIG. 6 is a sectional view along a line [6]-[6] in FIG. 2.
Figure 7:
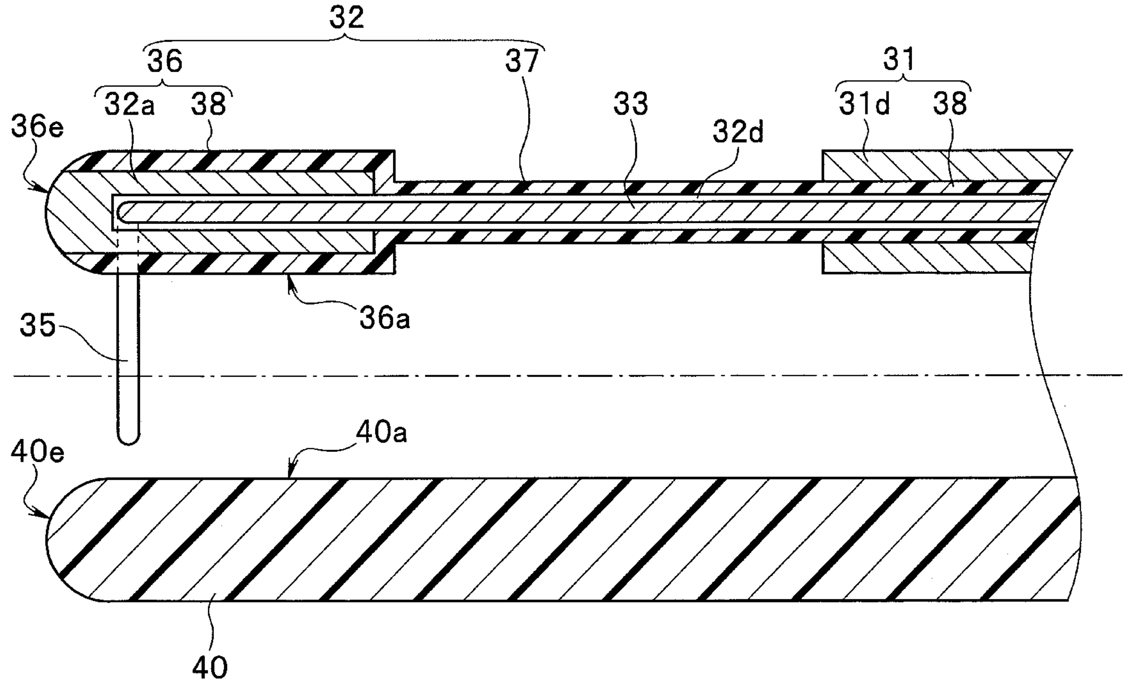
FIG. 7 is a sectional view along a line [7]-[7] in FIG. 6.

FIG. 5 is a front view of the electrode unit from a point facing a distal end surface of the electrode unit of the present embodiment. In other words, FIG. 5 is a diagram as viewed in a direction of arrow [5] in FIG. 2. FIG. 6 is a sectional view along a line [6]-[6] in FIG. 2. Therefore, in the direction along the first axis X in FIGS. 5 and 6, the right side of the figure is a leftward direction of the electrode unit and the left side of the figure is a rightward direction of the electrode unit. Furthermore, in the direction along the second axis Y in FIGS. 5 and 6, the upper side of the figure is an upward direction of the electrode unit and the lower side of the figure is a downward direction of the electrode unit. FIG. 7 is a sectional view along a line [7]-[7] in FIG. 6.

Figure 8:
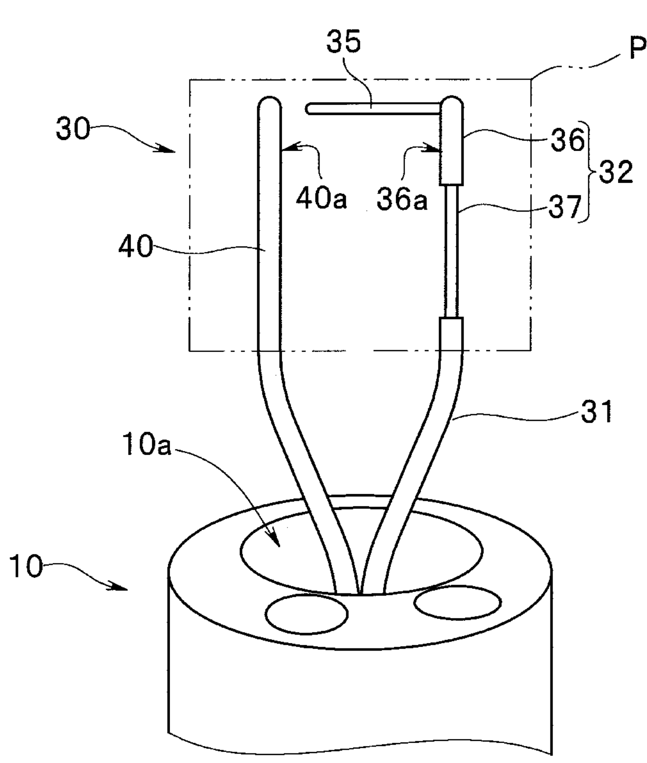
FIG. 8 is a schematic diagram illustrating a state in which the electrode unit of the first embodiment of the present invention is inserted through a device channel of a resectoscope.

FIG. 8 is a schematic diagram illustrating a state in which the electrode unit of the present embodiment is inserted through the device channel of the resectoscope. FIG. 8 illustrates a state in which a distal end part of the electrode unit projects toward the outer front side from a distal end surface of the device channel of the resectoscope.

As illustrated in FIGS. 2 to 4, the electrode unit 30 of the present embodiment is formed in an elongated shape with the direction along the longitudinal axis L as a longitudinal direction. The electrode unit 30 mainly includes, e.g., a proximal end rigid portion 31, an electrode supporting portion 32, an electrode wire 33, the electrode 35 and a tissue retaining portion 40.

The proximal end rigid portion 31 is a component member fixed to the electrode unit holding portion 23 (see FIG. 1) of the resectoscope 10. The electrode supporting portion 32 is joined to a distal end 31*a* (see FIGS. 2 and 4) of the proximal end rigid portion 31. An electrical connection portion 31*c* is arranged at a proximal end 31*b* (see FIGS. 2 to 4) of the proximal end rigid portion 31. When the proximal end rigid portion 31 is fixed to the electrode unit holding portion 23 (see FIG. 1), the electrical connection portion 31*c* is electrically connected to the electrode connector 24 of the resectoscope 10. Furthermore, the electrical connection portion 31*c* is electrically connected to the electrode 35 via the electrically conductive electrode wire 33 inserted through the inside of the electrode unit 30.

The electrode wire 33 is a linear member having electrical conductivity and is disposed so as to be inserted through the inside of each of the proximal end rigid portion 31 and the electrode supporting portion 32 of the electrode unit 30. The electrode wire 33 electrically connects the electrical connection portion 31*c* provided at the proximal end 31*b* of the electrode unit 30, and the electrode 35. When the resectoscope 10 is used, the electrode wire 33 serves as a component member that ensures electrical connection between the high-frequency power supply control device 55 and the electrode 35.

The electrode supporting portion 32 is a component portion that fixes and supports a proximal end 35*a* (see FIGS. 4 and 5) of the electrode 35. Furthermore, the electrode supporting portion 32 is formed in a substantially straight shape in its entirety and is disposed in parallel with the later-described tissue retaining portion 40.

The electrode supporting portion 32 is a part that when the resectoscope 10 is used, projects substantially linearly toward the outer front side from the distal end 11*a* (see FIG.

1) of the sheath 11. The electrode supporting portion 32 includes a distal end rigid portion 36 and an elastic region 37.

The distal end rigid portion 36 is a component portion having a hollow columnar outer shape with the direction along the longitudinal axis L as a longitudinal direction. In the present embodiment, the distal end rigid portion 36 is illustrated in a form having a substantially circular shape in section, but the distal end rigid portion 36 is not limited to this shape. For example, the sectional shape of the distal end rigid portion 36 may be, e.g., a polygonal shape.

As illustrated in FIGS. 6 and 7, the distal end rigid portion 36 includes a ceramic pipe 32*a* and a coating portion 38. Each of the ceramic pipe 32*a* and the coating portion 38 includes a material having an electrical insulating property.

The ceramic pipe 32*a* is an elongated tubular member including a through-hole 32*d* inside, the electrode wire 33 being inserted through the through-hole 32*d*. The coating portion 38 is a tubular member including, for example, a resin material. The coating portion 38 coats the ceramic pipe 32*a*.

In a part close to a distal end of each of the ceramic pipe 32*a* and the coating portion 38, a through-hole 32*c* for holding the proximal end 35*a* of the electrode 35 opens downward. The through-hole 32*c* communicates with the through-hole 32*d* of the ceramic pipe 32*a*.

The electrode 35 is a component portion that when the electrode unit 30 is used, implements resection treatment of a living tissue or a function that stops bleeding through coagulation of a tissue, by making a high-frequency electric current flow. The electrode 35 is formed using, for example, a linear member or a rod-shaped member including a material having electrical conductivity and rigidity (for example, a metal wire). The proximal end 35*a* of the electrode 35 is fixed to and supported by a predetermined part close to a distal end 36*e* of the distal end rigid portion 36. For the electrode 35 employed in the electrode unit 30 of the present embodiment, for example, a member including a rod-shaped portion having a diameter of around 0.5 mm is employed.

In the present embodiment, for the electrode 35, a material that is the same as a material of the electrically conductive (for example, metal) electrode wire 33 inserted through the inside of the electrode unit 30 is employed. In the present embodiment, the electrode 35 and the electrode wire 33 are integrally formed by a single metal wire member. Note that the electrode 35 is not limited to the form indicated in the present embodiment, and, for example, a form in which an electrode and an electrode wire are separate from each other and are provided continuously so as to ensure electrical connection between the electrode and the electrode wire may be employed.

The electrode 35 is arranged such that the proximal end 35*a* projects from a surface of the distal end rigid portion 36. In more detail, as illustrated in FIGS. 5 and 6, the proximal end 35*a* of the electrode 35 is provided so as to project outward from the part close to the distal end 36*e* of the distal end rigid portion 36 and extend a predetermined length in the downward direction along the second axis Y. Here, as illustrated in FIG. 5, the proximal end 35*a* extends in the downward direction relative to a plane including a line C (see FIG. 5) connecting a lower end surface 36*c* of the distal end rigid portion 36 and a lower end surface 40*c* of the tissue retaining portion 40.

At a part of the electrode 35, the part being farther than the proximal end 35*a*, a beam portion 35*b* is provided so as to extend in the leftward direction along the first axis X, by the electrode 35 being flexed.

Here, a length A (see FIG. 5) of the beam portion 35*b* extending in the leftward direction of the electrode unit 30 of electrode 35 (toward the right side of the figure in FIGS. 5 and 6) along the first axis X is set to be a length that allows the beam portion 35*b* to be located in a space between the electrode supporting portion 32 and the tissue retaining portion 40 (area indicated by sign S; see FIG. 2).

Furthermore, as viewed in the direction along the longitudinal axis L (see FIGS. 5 and 6), the proximal end 35*a* and the beam portion 35*b* of the electrode 35 form a substantially L-shape. Furthermore, as viewed in the direction along the first axis X (see FIGS. 2 to 4), the beam portion 35*b* extends in a direction substantially orthogonal to the longitudinal axis L.

The electrode 35 is electrically connected to the electrode wire 33 inside the distal end rigid portion 36. Here, as described above, the electrode 35 and the electrode wire 33 are formed by the same metal linear member.

In this way, the beam portion 35*b* of the electrode 35 is a free end and the electrode 35 is formed in a cantilevered shape. Furthermore, the electrode 35 is configured such that a high-frequency electric current is applied to the electrode 35 by electrical connection of the electrode 35 with the high-frequency power supply control device 55 being ensured via the electrode wire 33, the electrical connection portion 31*c*, the electrode unit holding portion 23, the electrode connector 24 and the cable 56.

The elastic region 37 of the electrode supporting portion 32 is a member that is interposed between, and connects, a proximal end of the distal end rigid portion 36 and the distal end 31*a* of the proximal end rigid portion 31. The elastic region 37 is formed so as to be elastic in a bending direction. A bending rigidity of the elastic region 37 is set to be lower than a bending rigidity of each of the distal end rigid portion 36 and the proximal end rigid portion 31. Note that in the present embodiment, as for the bending rigidity of the elastic region 37, for example, respective bending rigidities of the elastic region 37, the distal end rigid portion 36 and the proximal end rigid portion 31 can arbitrarily be set by making materials of the elastic region 37, the distal end rigid portion 36 and the proximal end rigid portion 31 different from one another.

Furthermore, the elastic region 37 is configured by a coating portion 38, which is a resin tube. The present embodiment indicates an example in which the coating portion 38 of the distal end rigid portion 36 and the coating portion 38 of the elastic region 37 are configured by a same member that extends continuously in the direction along the longitudinal axis L.

The electrode wire 33 is inserted through the inside of the coating portion 38 of the elastic region 37. In other words, in the present embodiment, the ceramic pipe 32*a* inserted inside the coating portion 38 serves to enhance the bending rigidity of the distal end rigid portion 36 relative to the bending rigidity of the elastic region 37.

As illustrated in FIG. 7, the proximal end rigid portion 31 of the present embodiment is configured by a coating portion 38 formed of a resin tube, and a metal pipe 31*d*. The present embodiment indicates an example in which the coating portion 38 of the proximal end rigid portion 31 and the coating portion 38 of the elastic region 37 are configured by a same member that extends continuously in the direction along the longitudinal axis L.

The electrode wire 33 is inserted through the inside of the coating portion 38 of the proximal end rigid portion 31. The metal pipe 31*d* covers an outer circumference of the coating portion 38. In other words, in the present embodiment, the metal pipe 31*d* serves to enhance the bending rigidity of the proximal end rigid portion 31 relative to the bending rigidity of the elastic region 37.

The means for providing the configuration in which the bending rigidity of the elastic region 37 is lower than the bending rigidities of the distal end rigid portion 36 and the proximal end rigid portion 31 is not limited to the means of making the materials of the component members different, which has been indicated as an example in the present embodiment. As other means, for example, the bending rigidity of the elastic region 37 can also be set to be lower than the bending rigidities of the distal end rigid portion 36 and the proximal end rigid portion 31 by reducing an outer diameter of the elastic region 37 to be smaller than respective outer diameters of the distal end rigid portion 36 and the proximal end rigid portion 31.

On the other hand, the tissue retaining portion 40 has a function that when the resectoscope 10 is used, retains a surface of a living tissue in resection of a desired part (predetermined region including a lesion part) of the living tissue using the electrode unit 30. Furthermore, the tissue retaining portion 40 is a component portion provided to hold a distance between the electrode 35 and a treatment target living tissue constant in order to curb the electrode 35 penetrating excessively deeply from the surface of the living tissue (stopper function).

The tissue retaining portion 40 is a substantially linear rod-shaped member that is entirely elastic and that is formed with a non-electrically conductive material. In the tissue retaining portion 40, the distal end 40*e* is a free end and a proximal end is fixed to and supported by one side surface portion close to the distal end of the proximal end rigid portion 31, and consequently, the tissue retaining portion 40 is formed in a cantilevered shape.

In more detail, the tissue retaining portion 40 is disposed substantially in parallel with the electrode supporting portion 32 so as to extend along the longitudinal axis L. In this case, respective lengths of extension of the electrode supporting portion 32 and the tissue retaining portion 40 are set to be respective lengths that are substantially the same. The electrode supporting portion 32 and the tissue retaining portion 40 are disposed so as to be spaced a predetermined distance (see sign S in FIG. 2) from each other in the direction along the first axis X (left-right direction of the electrode unit 30).

In other words, the electrode supporting portion 32 and the tissue retaining portion 40 are disposed so as to overlap each other in the direction along the first axis X (see FIGS. 3 and 4). Therefore, the respective portions (32, 40) include respective facing surfaces 36*a*, 40*a* (see FIG. 7) that face each other in the direction along the first axis X.

Here, "facing surfaces that face each other" refers to:

a surface of the distal end rigid portion 36 of the electrode supporting portion 32 disposed on the right side of the electrode unit 30 (as the distal end side is viewed from the proximal end side), the surface facing substantially the leftward direction (sign 36*a* in FIG. 7); and a surface of the tissue retaining portion 40 disposed on the left side of the electrode unit 30 (as the distal end side is viewed from the proximal end side), the surface facing the rightward direction (sign 40*a* in FIG. 7).

In other words, the facing surfaces 36*a*, 40*a* are respective surfaces of the electrode supporting portion 32 and the tissue retaining portion 40, the surfaces facing each other in the space between the electrode supporting portion 32 and the tissue retaining portion 40. Therefore, although the facing surface 36*a* of the electrode supporting portion 32 and the facing surface 40*a* of the tissue retaining portion 40 are disposed in parallel, the facing surface 36*a* and the facing surface 40*a* do not necessarily need to be disposed in parallel.

In the electrode unit 30 configured as above, as illustrated in FIG. 2, etc., as viewed in the direction along the second axis Y, the electrode 35 is exposed to the outside in the space S between the distal end rigid portion 36 of the electrode supporting portion 32 and a region in the vicinity of the distal end portion of the tissue retaining portion 40.

Furthermore, as illustrated in FIG. 5, etc., for example, as viewed from the distal end side (front side), the electrode 35 is exposed to the outside in a region of the space S between the distal end rigid portion 36 of the electrode supporting portion 32 and the region in the vicinity of the distal end portion of the tissue retaining portion 40 in the direction along the longitudinal axis L.

In the electrode unit 30 of the present embodiment, which is configured as above, as illustrated in FIG. 8, an imaginary plane P including respective center axes of the electrode supporting portion 32 and the tissue retaining portion 40 (rectangle indicated by alternate long and two short dashes lines in FIG. 8) is formed. The imaginary plane P corresponds to a contact surface when the electrode unit 30 is brought into contact with a wall surface of a living tissue during use of the resectoscope 10.

Here, the electrode 35 is disposed so as to project in the downward direction in the direction along the second axis Y relative to an imaginary line connecting the respective center axes of the electrode supporting portion 32 and the tissue retaining portion 40 and extending along the first axis X. Here, the imaginary line is a parallel line included in the imaginary plane P.

Therefore, in the electrode unit 30 of the present embodiment, the above-described imaginary plane P is formed by the electrode supporting portion 32 and the tissue retaining portion 40, and the electrode 35 is disposed in the downward direction in the second axis Y direction relative to the imaginary plane P. In the electrode unit 30 of the present embodiment, such configuration as above allows the electrode supporting portion 32 and the tissue retaining portion 40 to curb the electrode 35 excessively deeply penetrating inward from a surface of a living tissue during use for treatment.

The electrode unit 30 of the present embodiment is configured as above. An operation and procedure of one-piece resection treatment of a living tissue in a predetermined region including a lesion part inside an organ 100 of a subject using the endoscope system 1 including the electrode unit 30 of the present embodiment, which is configured as above, will be described below with reference to FIGS. 9 to 23 and 58.

Figure 9:
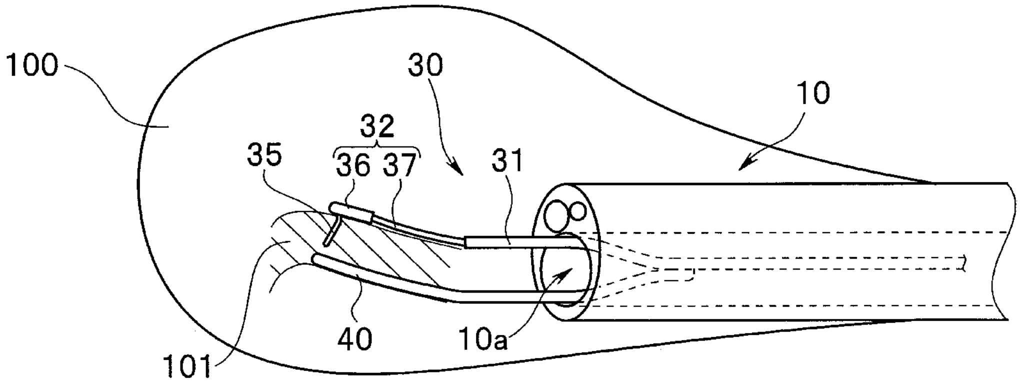
FIG. 9 is a schematic diagram illustrating a state in which the resectoscope to which the electrode unit of the first embodiment of the present invention is applied is inserted into a body cavity of a subject.
Figure 58:
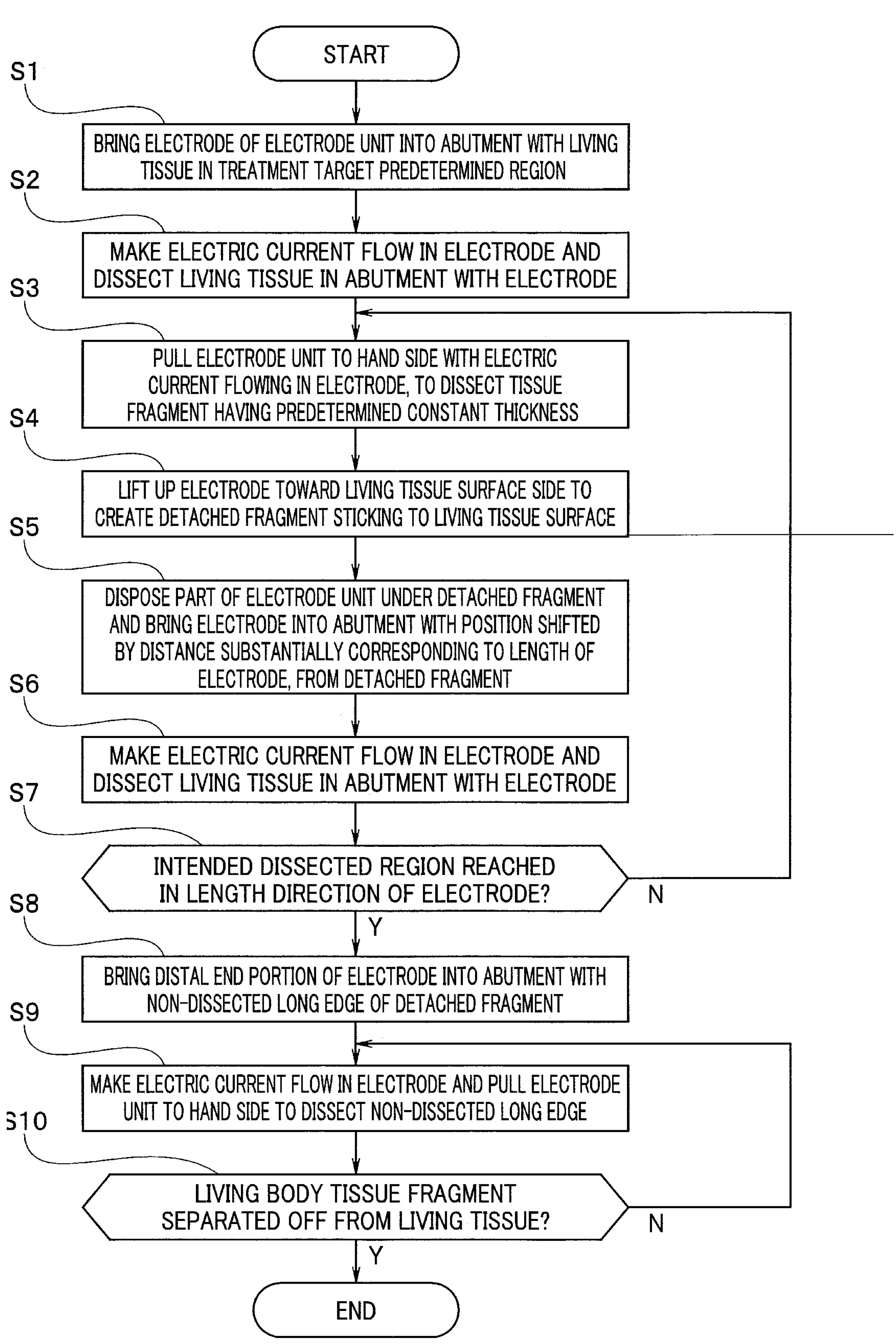
FIG. 58 is a flowchart illustrating a procedure for treatment performed using the resectoscope to which the electrode unit of the first embodiment of the present invention is applied.

FIGS. 9 to 23 are diagrams schematically illustrating a procedure for performing treatment of a living tissue inside a body cavity (organ) of a subject such as a human body using a resectoscope to which the electrode unit of the present embodiment is applied. From among the figures, FIG. 9 is a schematic diagram illustrating a state in which the resectoscope to which the electrode unit of the present embodiment is applied is inserted into a body cavity (organ) of a subject such as a human body. Furthermore, FIG. 58 is a flowchart illustrating a procedure for treatment performed using the resectoscope to which the electrode unit of the present embodiment is applied.

Note that the below-described example treatment procedure is an example of a case where one-piece resection in which a living tissue that is a treatment target (a living tissue including a lesion part, for example, a cancer) is resected such that the living tissue is shaped in a block is performed.

In a case where one-piece resection treatment of a living tissue inside an organ 100 is performed using the electrode unit 30 of the present embodiment, first, a user inserts the resectoscope 10 into the organ 100 in a predetermined procedure. Note that, e.g., the procedure for inserting the resectoscope 10 into the organ 100 and a method for filling the inside of the organ 100 with a perfusate are similar to procedures of cases where a conventional resectoscope is used, and thus, description of the procedures will be omitted.

After a distal end portion of the resectoscope 10 being disposed at a predetermined position (position at which a lesion part or the like is located) inside the organ 100, the user inserts the electrode unit 30 through the device channel 10*a* of the resectoscope 10 and performs an operation to make the distal end of the electrode unit 30 project by a predetermined amount from a distal end portion of the device channel toward the outer front side. The operation is also similar to an operation of a conventional resectoscope.

Next, the user brings the respective lower end surfaces of the distal end rigid portion 36 of the electrode supporting portion 32 and the tissue retaining portion 40 into a posture in which the lower end surfaces face the treatment target living tissue inside the organ 100.

Subsequently, the user makes the imaginary plane P of the electrode supporting portion 32 and the tissue retaining portion 40 face a wall surface 101 of the organ 100 and positions the electrode 35 at a living tissue (living tissue including the lesion part) in a predetermined region that is a treatment target and brings the electrode 35 into abutment with the living tissue (step S1 in FIG. 58). The state at this time is illustrated in FIGS. 9 and 10.

Figure 10:
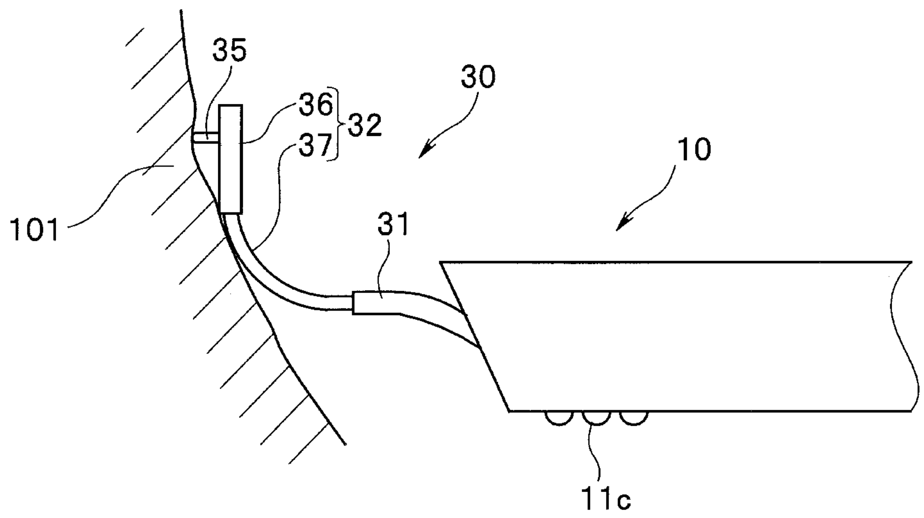
FIG. 10 is a schematic view of the electrode unit in FIG. 9 from a lateral side.

In other words, FIGS. 9 and 10 illustrate a state in which the imaginary plane P of the electrode supporting portion 32 and the tissue retaining portion 40 of the electrode unit 30 is disposed so as to face the wall surface 101 of the living tissue with the electrode unit 30 projecting by the predetermined amount from the distal end portion of the resectoscope 10 and the distal end of the electrode 35 is brought into contact with the wall surface 101. Of the figures, FIG. 9 is a schematic diagram of an outer appearance and FIG. 10 is a schematic view from a lateral side.

Next, the user operates the switch 55*a* to start output of a high-frequency electric current from the high-frequency power supply control device 55. Consequently, the high-frequency electric current flows from the electrode 35 toward the collection electrode 11*c* through the perfusate, and thus, the living tissue that is in contact with the electrode 35 generates heat and the living tissue is thus dissected. Then, when dissection of the living tissue is started by the electrode 35 due to the start of the output of the high-frequency electric current, as illustrated in FIGS. 11 to 13, the electrode 35 penetrates into the living tissue (step S2 in FIG. 58).

Figure 11:
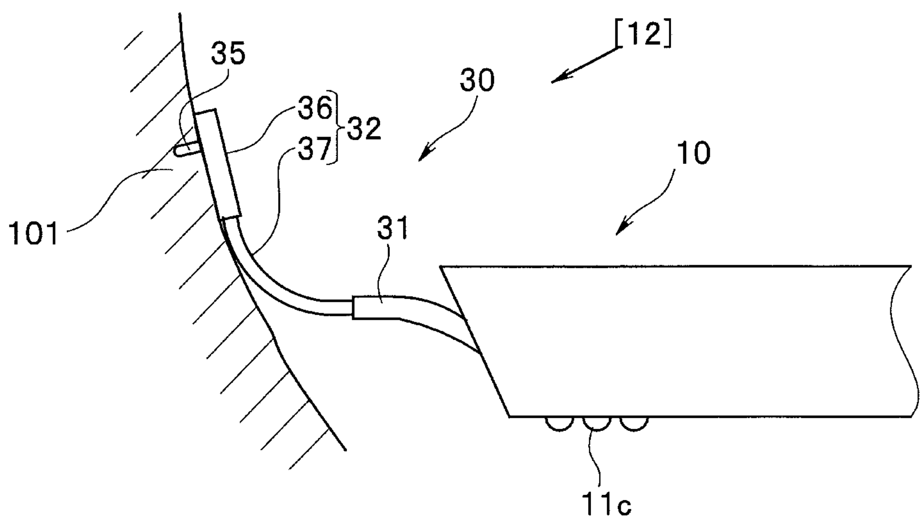
FIG. 11 is a diagram illustrating operation of the electrode unit of the first embodiment of the present invention, which is a schematic view of a state in which an electrode penetrates into a living tissue from a lateral side.
Figure 12:
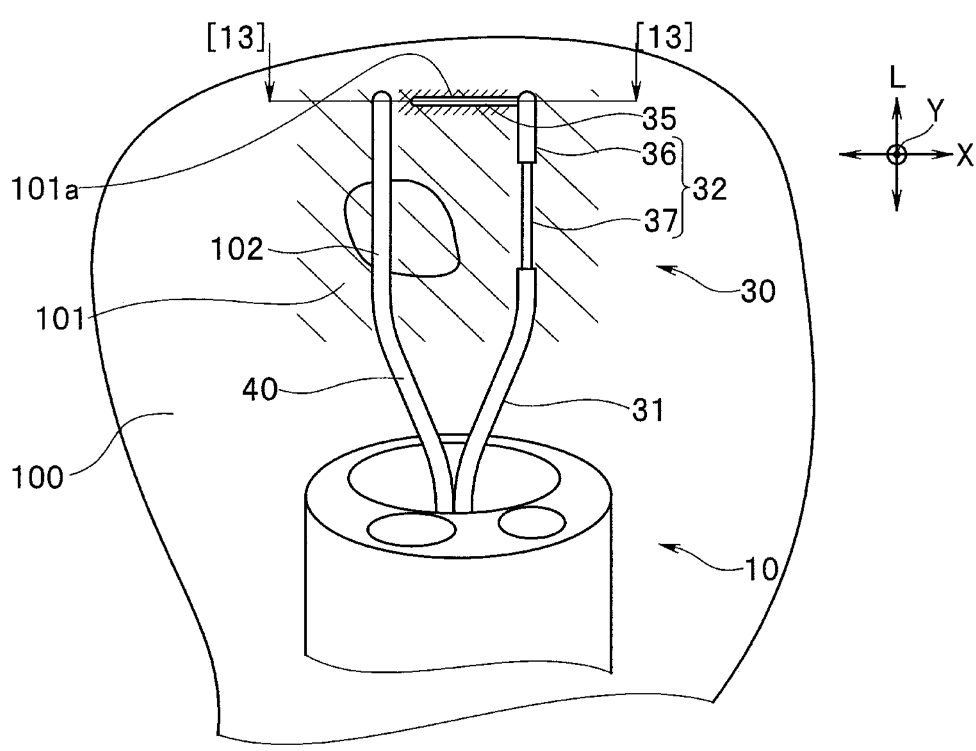
FIG. 12 is a schematic view in a direction of arrow [12] in FIG. 11.
Figure 13:
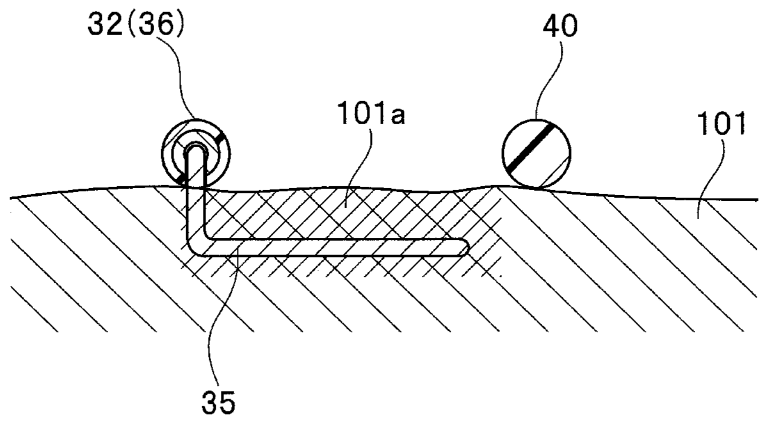
FIG. 13 is a schematic view illustrating a section along a line [13]-[13] in FIG. 12.

FIGS. 11 to 13 illustrate a state in which the electrode 35 penetrates into the living tissue. Of the figures, FIG. 11 is a schematic view from a lateral side, FIG. 12 is a schematic view in a direction of arrow [12] in FIG. 11 and FIG. 13 is a schematic diagram illustrating a section along a line [13]-[13] in FIG. 12.

In this state, the electrode 35 has cauterized the living tissue and penetrated into the tissue. In FIGS. 12 and 13, the part indicated by cross-hatching and sign 101*a* indicates a state in which a part of the living tissue is cauterized. Hereinafter, such part is called "cauterized part". Furthermore, in FIG. 12, sign 102 denotes a lesion part, for example, a cancer.

In this state, when the electrode 35 penetrates to a predetermined depth inside the living tissue, the distal end rigid portion 36 comes into abutment with a tissue surface that is not dissected by the electrode 35. Here, a region cauterized by the electrode 35 depends on a thickness dimension (width dimension) of the electrode 35. In the electrode unit 30 of the present embodiment, a thickness dimension (width dimension) of the distal end rigid portion 36 is set to be larger (wider) than the thickness dimension (width dimension) of the electrode 35, and thus, when the electrode 35 penetrates into the living tissue by an amount corresponding to a length of the proximal end 35*a*, the distal end rigid portion 36 comes into abutment with a tissue surface not cauterized by the electrode 35. A tissue surface that the tissue retaining portion 40 is concurrently in abutment with is not cauterized, the tissue retaining portion 40 being provided in plane and parallel with the distal end rigid portion 36 and being included in the imaginary plane P, and thus, the tissue retaining portion 40 does not penetrate into the living tissue. Therefore, the distal end rigid portion 36 and the tissue retaining portion 40 thus function as a stopper that restricts the electrode 35 from penetrating to a predetermined amount of depth or more inside the living tissue.

In this state, the imaginary plane P of the distal end of the electrode unit 30 is pressed against the wall surface 101 of the living tissue with a predetermined amount of force. Then, the electrode supporting portion 32 and the tissue retaining portion 40 of the electrode unit 30 are pressed against the living tissue, and thus parts of the living tissue, which are in contact with the electrode supporting portion 32 and the tissue retaining portion 40, respectively, are depressed inward. On the other hand, a part of the living tissue, the part being located in a region between the electrode supporting portion 32 and the tissue retaining portion 40, deforms into a bulging shape projecting outward from the tissue surface as indicated by sign 101*b* in FIGS. 14 and 15. At this time, as described above, the electrode supporting portion 32 and the tissue retaining portion 40 restrict penetration to the predetermined depth or more inside the living tissue, and thus, the bulging shape portion formed by the living tissue is consistently kept constant in shape. This pressing operation defines a depth (thickness) dimension of the living tissue to be resected.

Figure 14:
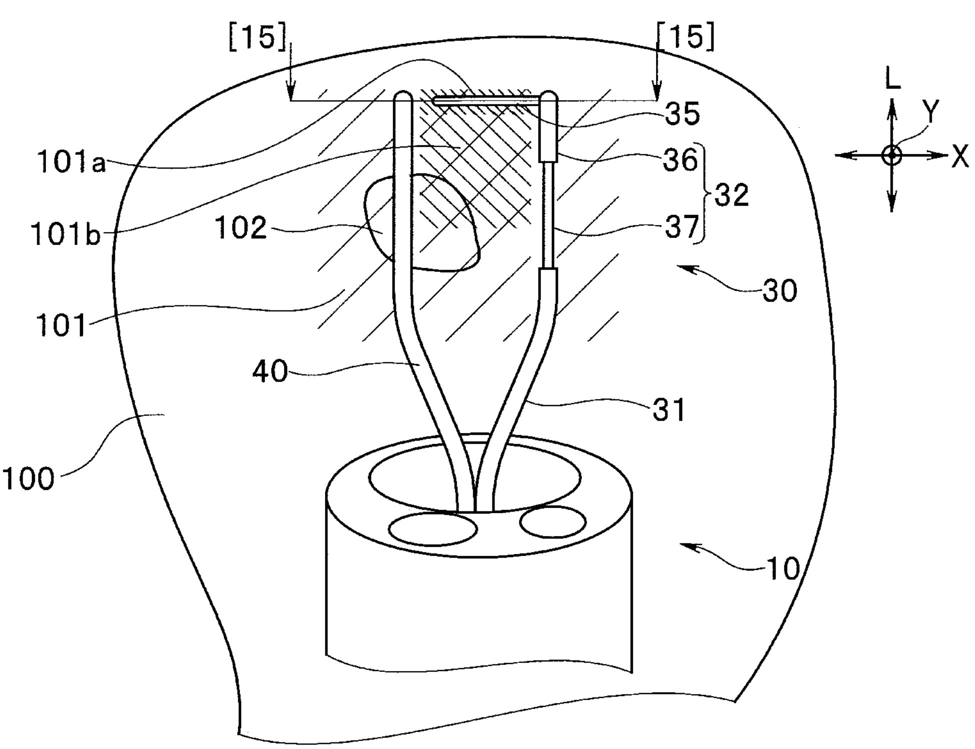
FIG. 14 is a schematic diagram illustrating a state in the electrode unit of the first embodiment of the present invention when a pressing force is applied to a distal end of the electrode unit with the electrode penetrating into the living tissue.
Figure 15:
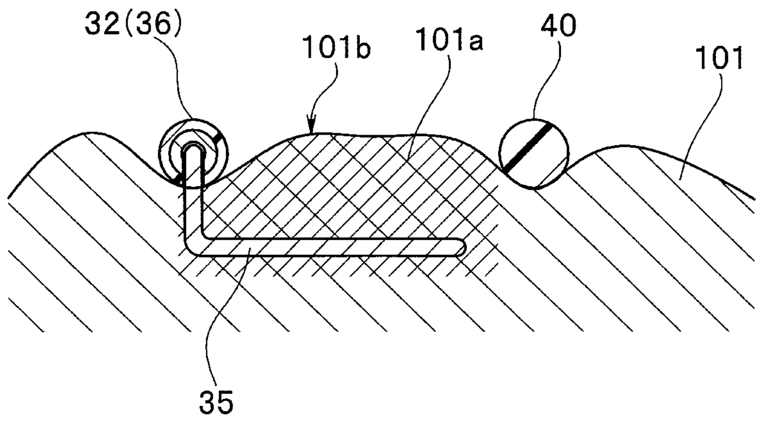
FIG. 15 is a sectional view along a line [15]-[15] in FIG. 14.

FIGS. 14 and 15 are schematic diagrams illustrating a state in which a pressing force is applied to the distal end of the electrode unit with the electrode 35 penetrating into the living tissue. Of the figures, FIG. 14 is a schematic diagram corresponding to FIG. 12 and FIG. 15 is a sectional view corresponding to FIG. 13 and along a line [15]-[15] in FIG. 14.

In the state illustrated in FIGS. 14 and 15, the user operates the resectoscope 10 to pull the electrode unit 30 toward the hand side (proximal end side, that is, the arrow L1 direction in FIG. 16) in the direction along the longitudinal axis L and move the electrode supporting portion 32 along the wall surface 101 of the organ 100. Then, inside the living tissue, the electrode 35 moves in a direction along the wall surface 101 (step S3 in FIG. 58). At this time, since the electrode 35 penetrates into the tissue by the predetermined depth dimension, a tissue fragment having a predetermined constant thickness is resected.

Figure 16:
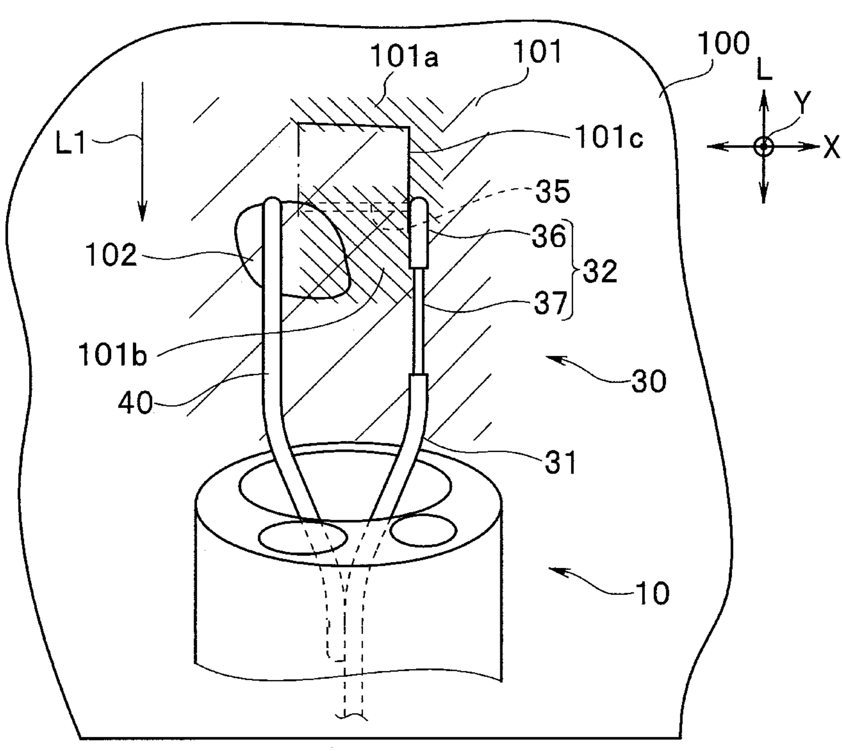
FIG. 16 is a schematic diagram illustrating a state of a dissection operation being performed after the state illustrated in FIGS. 14 and 15.
Figure 17:
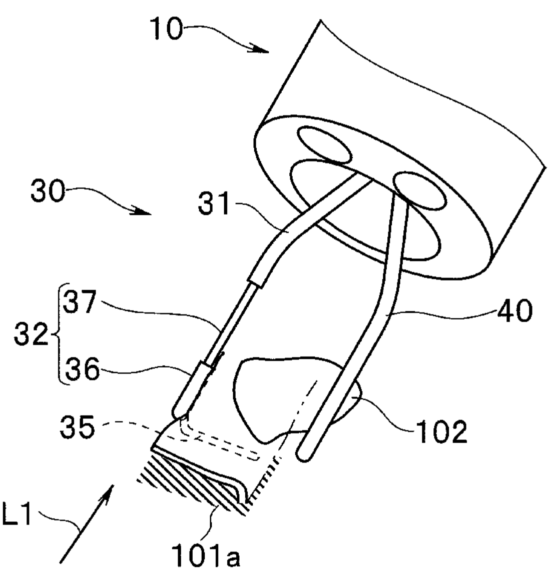
FIG. 17 is a schematic view of the electrode unit in the state in FIG. 16 in an obliquely rightward direction from the front side.

Here, FIGS. 16 and 17 are schematic diagrams illustrating a state in which a dissection operation in which the electrode unit 30 is pulled in the arrow L1 direction is performed after the state illustrated in FIGS. 14 and 15 (state in which the electrode 35 penetrates into the living tissue and a pressing force is applied to the distal end of the electrode unit). Of the figures, FIG. 16 is a schematic diagram corresponding to FIGS. 12 and 14. Furthermore, FIG. 17 is a schematic view of the electrode unit in the state in FIG. 16 in an obliquely rightward direction from the front side.

In this situation, as described above, the user presses the distal end part (the electrode supporting portion 32 and the tissue retaining portion 40) of the electrode unit 30 against the wall surface 101 of the organ 100. At this time, even if the pressing force varies during the operation in which the electrode unit 30 is pulled, the depth of penetration of the electrode 35 into the tissue is maintained constant by the imaginary plane P. Furthermore, even if the pressing force provided by the user varies, an amount of force with which the electrode 35 is pressed against the living tissue side is maintained substantially constant because of the elastic region 37 appropriately bending via an elastic force of the elastic region 37 itself. Consequently, an amount of force with which the distal end rigid portion 36 and the tissue retaining portion 40 deform the living tissue is also maintained substantially constant, and thus, the depth of penetration of the electrode 35 into the tissue is also maintained substantially constant.

Therefore, in the situation illustrated in FIGS. 16 and 17, when the electrode unit 30 is pulled in the direction along the longitudinal axis L, the electrode 35 that has penetrated to the predetermined depth inside the living tissue dissects a part of the living tissue, the part being the bulging shape portion 101*b*, to the predetermined depth. Here, sign 101*c* in FIG. 16 denotes a dissection line of dissection of the living tissue by an operation to move the electrode 35 in a longitudinal axis L1 direction (first-round operation).

At this time, since the electrode unit 30 is pulled in a longitudinal axis L direction and also presses the tissue surface with the constant amount of force, the position of the bulging shape portion 101*b* is shifted as the electrode unit 30 is moved in the longitudinal axis L direction.

Furthermore, in the electrode unit 30 of the present embodiment, the electrode 35 is arranged on the electrode supporting portion 32 side alone, and thus, the tissue retaining portion 40 side merely moves while pressing the surface of the living tissue. Accordingly, on the electrode supporting portion 32 side, the living tissue is dissected by the electrode 35, and on the tissue retaining portion 40 side, the living tissue is not dissected.

Figure 18:
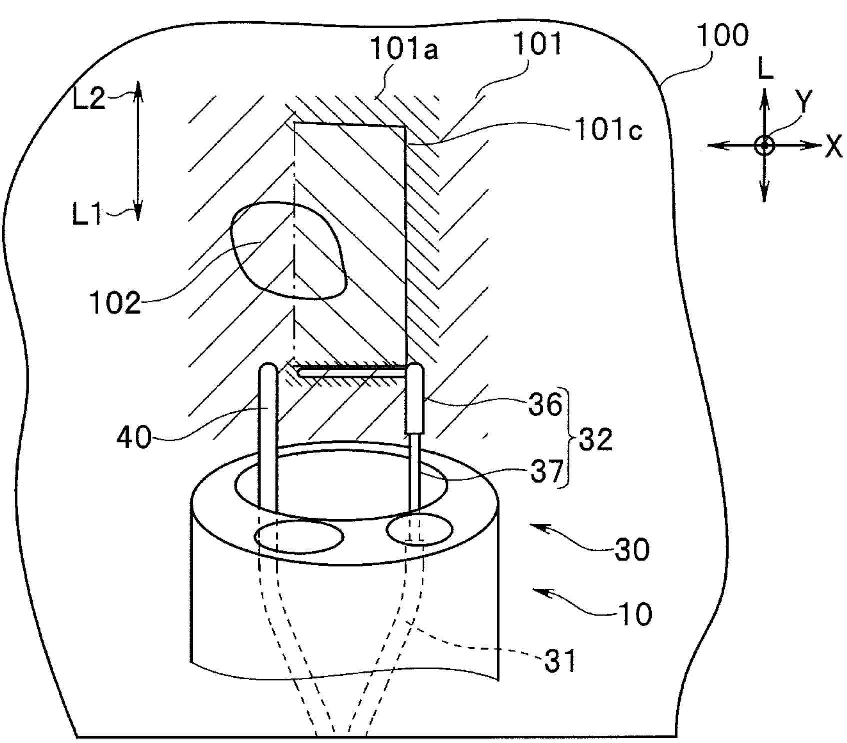
FIG. 18 is a schematic diagram illustrating a state in which the electrode has reached a dissection end position after the operation in FIGS. 16 and 17.

FIG. 18 illustrates a state in which the electrode 35 has reached a dissection end position, which is a goal, in the treatment target predetermined region after the operation illustrated in FIGS. 16 and 17 (operation of pulling the electrode 35 in the longitudinal axis L1 direction to dissect the living tissue). When the state illustrated in FIG. 18 is reached, the user performs an operation to lift up the electrode 35 toward the living tissue surface side (step S4 in FIG. 58).

At this time, in the living tissue, a channel shape (U-shape) dissection line 101*c* in which two dissected edges that are parallel to the axis direction of the electrode 35 and each have a length dimension substantially equal to a length of the electrode 35 and one dissected long edge having a predetermined length dimension in the direction along the longitudinal axis L are continuous with one another (hereinafter, referred to as "channel dissection line") is formed. When the substantially rectangular region in the living tissue surface, the substantially rectangular region including the channel dissection line 101*c*, is viewed, the other long edge at a point facing the dissected long edge included in the channel dissection line 101*c* (hereinafter referred to as "non-dissected long edge) is not dissected by the electrode 35. In other words, a detached fragment sticking to the living tissue surface via the non-dissected long edge is created (step S4 in FIG. 58).

After the state illustrated in FIG. 18, a next second-round dissection operation is performed. The user operates the switch 55*a* to terminate the output of the high-frequency electric current from the high-frequency power supply control device 55. Then, the detached fragment is turned up and the electrode unit 30 is moved in the arrow L2 direction in FIG. 18 and the electrode supporting portion 32 is disposed so as to slide under the detached fragment. In other words, the electrode supporting portion 32 is disposed on the part cauterized in the first round and the detached fragment is disposed on the electrode supporting portion 32. In this state, the user positions the electrode 35 at the distal end of the electrode supporting portion 32 at a point in the vicinity of the initial cauterized part 101*a*, the point being shifted by a distance substantially corresponding to the length of the electrode 35 from the non-dissected long edge, and brings the electrode 35 into abutment with the point (step S5 in FIG. 58).

Figure 19:
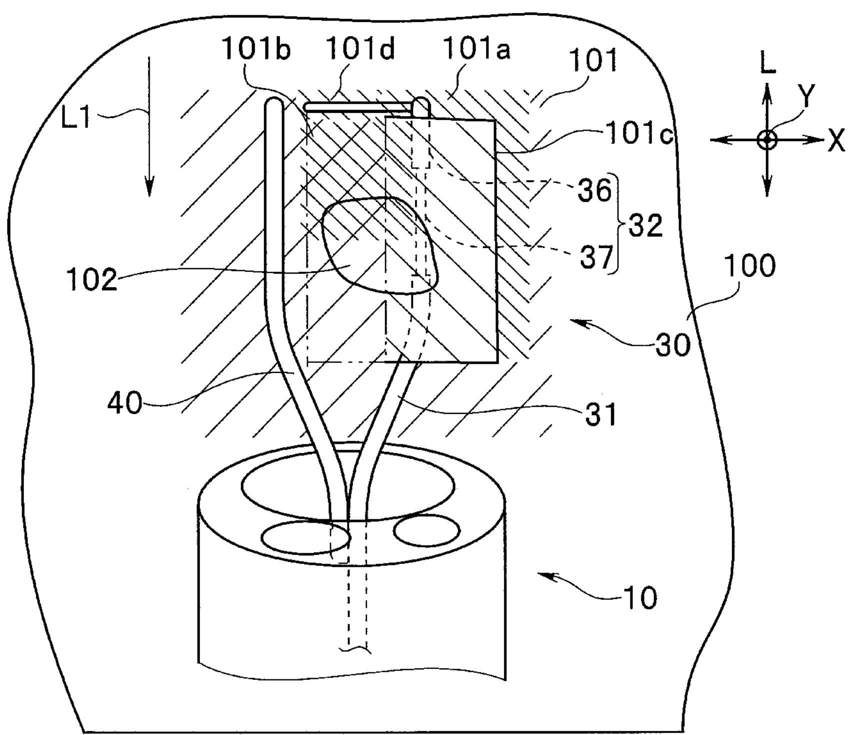
FIG. 19 is a schematic diagram illustrating a disposition of the electrode when a next second-round dissection operation is performed after the state illustrated in FIG. 18.

Next, the user operates the switch 55*a* to start output of a high-frequency electric current from the high-frequency power supply control device 55 and dissects a living tissue that is in contact with the electrode 35. Disposition of the electrode 35 at this time is illustrated in FIG. 19. FIG. 19 illustrates a state in which a living tissue in the vicinity of the first-round cauterized part 101*a* has been cauterized by the electrode 35 in the second-round operation. Here, a cauterized part resulting from the second-round operation is denoted by sign 101*d* in the figure (step S6 in FIG. 58).

The second-round dissection operation is performed from the state in FIG. 19. The second-round dissection operation itself is similar to the first-round dissection operation (see FIGS. 14 to 18). In other words, the user operates the resectoscope 10 to pull the electrode unit 30 toward the hand side (proximal end side, that is, the arrow L1 direction in FIG. 16) in the direction along the longitudinal axis L to move the electrode supporting portion 32 along the wall surface 101 of the organ 100 (step S3 in FIG. 58). Subsequently, when the electrode 35 has reached the goal dissection end position in the treatment target predetermined region, the user performs an operation to lift up the electrode 35 toward the living tissue surface side. Consequently, a detached fragment sticking to the living tissue surface via a non-dissected long edge is created so as to have a size that is larger than a size of the detached fragment created in the first round by an amount of the shifting by the distance substantially corresponding to the length of the electrode 35 (step S4 in FIG. 58). Details of respective steps of the second-round dissection operation are the same as the steps of the first-round operation. Therefore, description of the details will be omitted.

Figure 20:
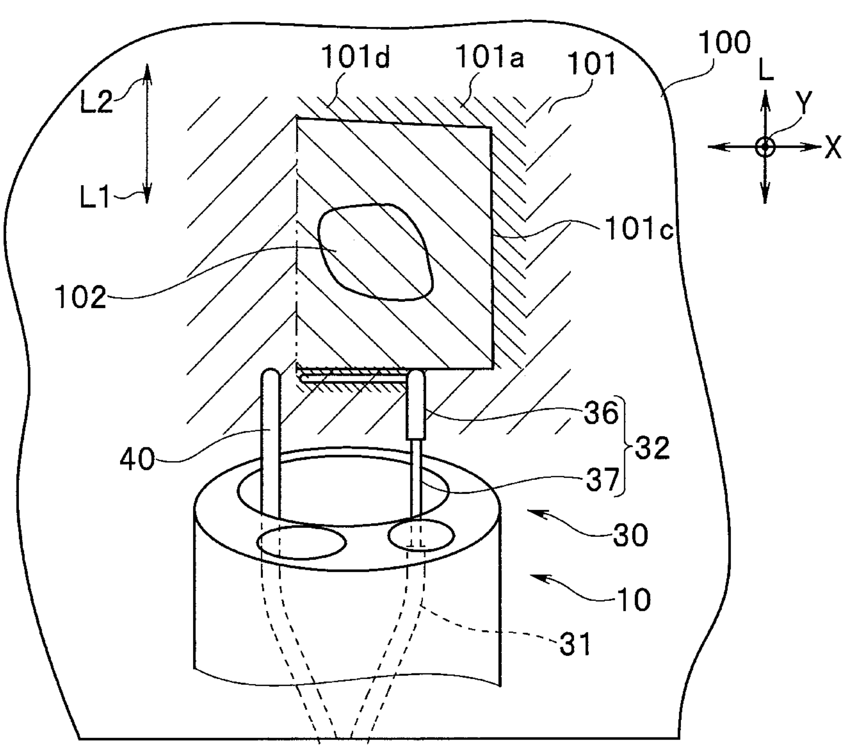
FIG. 20 is a schematic diagram illustrating a state in which the electrode has reached the dissection end position from the state illustrated in FIG. 19 by the second-round operation being performed.

FIG. 20 illustrates a state in which the electrode 35 has reached the goal dissection end position in the treatment target predetermined region after the second-round operation (operation of pulling the electrode 35 in the longitudinal axis L1 direction to dissect the living tissue) from the state illustrated in FIG. 19. After the state illustrated in FIG. 20 being reached, the user performs an operation to lift up the electrode 35 toward the living tissue surface side and operates the switch 55*a* to terminate the output of the high-frequency electric current from the high-frequency power supply control device 55. Then, the detached fragment is turned up and the electrode unit 30 is moved in the arrow L2 direction in FIG. 20 and the electrode supporting portion 32 is disposed so as to be slid under the detached fragment to achieve the state illustrated in FIG. 21.

Consequently, the channel dissection line 101*c* having the channel shape (U-shape), which is formed in the living tissue, is a form in which the two dissected edges parallel to an axis direction of the electrode 35 are extended. Even in this state, the non-dissected long edge at the point facing the dissected long edge of the channel dissection line 101*c* is not dissected by the electrode 35.

Subsequently, a next n-th round dissection operation is performed from the state in FIG. 21. In other words, in a procedure for performing one-piece resection of a living tissue using the electrode unit 30 of the present embodiment, a series of the above-described steps of the operation (first-round dissection operation: see FIGS. 14 to 18) is repeated a plurality of times (n times) (looped processing in steps S3 to S6 in FIG. 58), and if a dissected region in the axis direction (length direction) of the electrode 35 has reached the predetermined region including the lesion part inside the organ 100 of the subject (region intended to be dissected), a final dissection operation described next is performed (step S7 in FIG. 58). Here, the final dissection operation is an operation to dissect the non-dissected long edge to resect a block-shaped living tissue fragment in one piece. In the example procedure described here, a third-round dissection operation will be described as the final dissection operation.

After the state illustrated in FIG. 20, in order to perform the next third-round (last) dissection operation, the electrode unit 30 is moved in the arrow L2 direction in FIG. 20 and the electrode 35 is positioned at, and brought into abutment with, the vicinity of the second-round cauterized part 101*d*. Disposition of the electrode 35 at this time is illustrated in FIG. 21. FIG. 21 illustrates a state in which a living tissue in the vicinity of the second-round cauterized part 101*d* has been cauterized by the electrode 35 in the this-time (third-round, that is, last) operation. Here, sign 101*e* denotes the cauterized part in the third-round operation.

Figure 22:
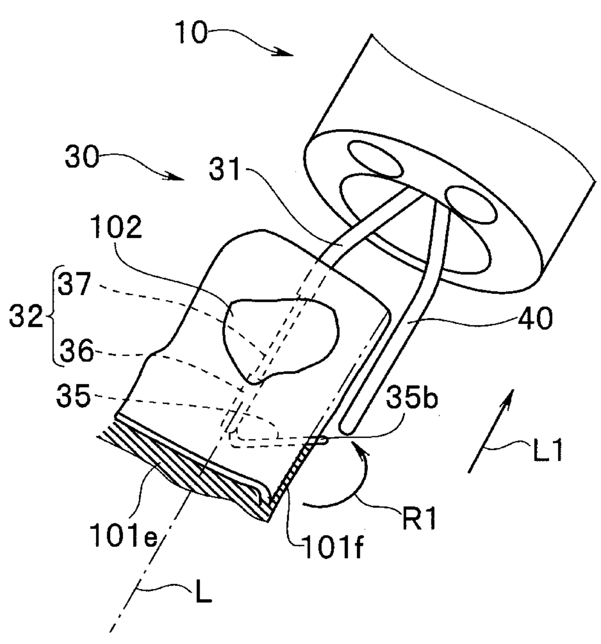
FIG. 22 is a schematic view of the electrode unit during the final dissection operation being performed after the state in FIG. 21, in an obliquely rightward direction from the front side.
Figure 23:
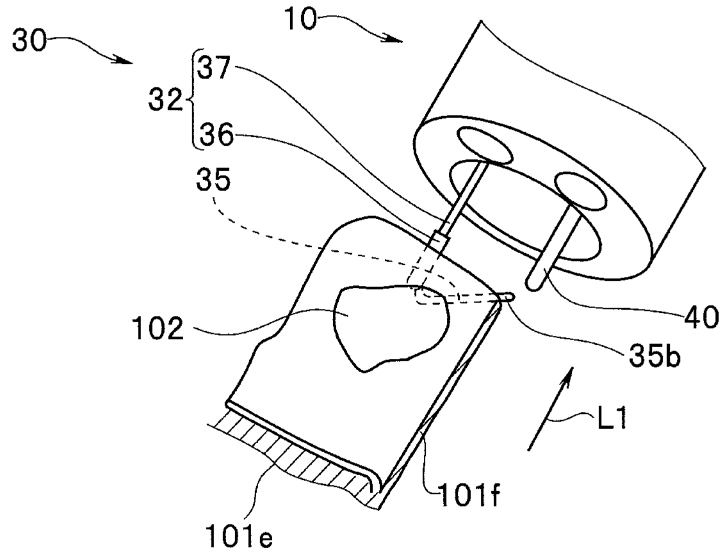
FIG. 23 is a schematic diagram illustrating a state in which the electrode has reached the dissection end position separating off a living tissue fragment in the final dissection operation after the state in FIG. 22.

FIGS. 22 and 23 are schematic views of the electrode unit during the third-round dissection operation in an obliquely rightward direction from the front side. Of the figures, FIG. 22 is a diagram illustrating a state during the third-round dissection operation being performed. FIG. 23 illustrates a state in which the electrode has reached the dissection end position separating off a living tissue fragment in the third-round dissection operation.

Figure 21:
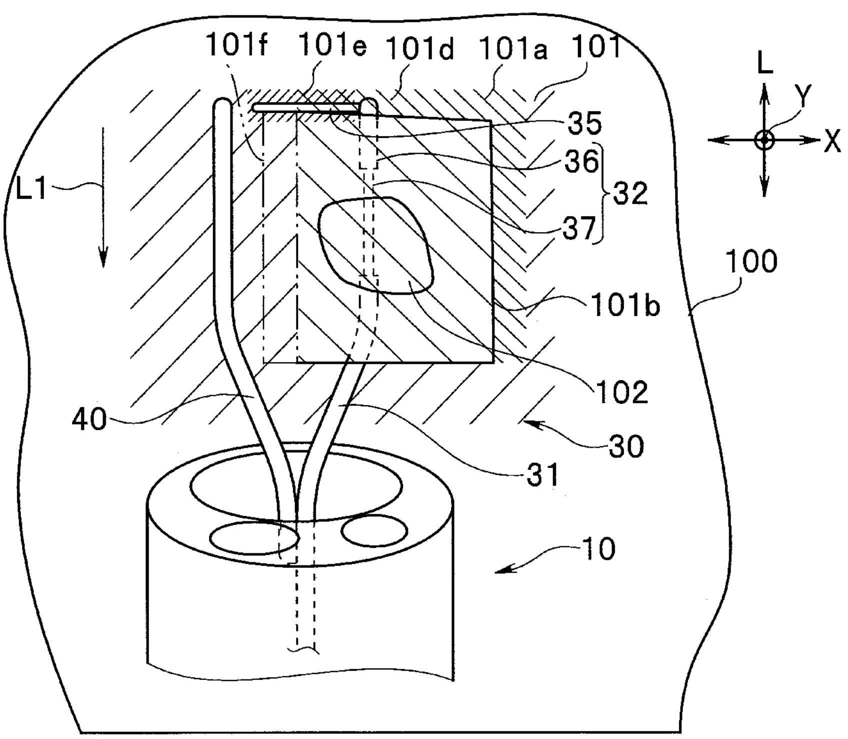
FIG. 21 is a schematic diagram illustrating a disposition of the electrode when a next third-round dissection operation (final dissection operation) is performed after the state illustrated in FIG. 20.

The third-round dissection operation is performed from the state in FIG. 21. As described above, the third-round dissection operation performed here is a final dissection operation in which the non-dissected long edge is dissected to resect a block-shaped living tissue fragment in one piece.

As illustrated in FIGS. 21 and 22, in the third-round dissection operation, first, the vicinity of a distal end portion of the beam portion 35*b* of the electrode 35 is brought into abutment with the vicinity of a point of intersection between one of the two resected edges and a non-dissected long edge 101*f* (step S8 in FIG. 58). In this state, the user operates the switch 55*a* to start output of a high-frequency electric current from the high-frequency power supply control device 55 and performs an operation to pull the electrode unit 30 in the arrow L1 direction (step S9 in FIG. 58). Then, the non-dissected long edge 101*f* is dissected.

In this case, the electrode unit 30 is rotated slightly around the longitudinal axis L in the arrow R1 direction in FIG. 22 to make the distal end portion of the beam portion 35*b* of the electrode 35 be slightly spaced from the living tissue surface, and the pressing force of the electrode unit 30 pressing the living tissue surface is reduced, enabling easy dissection of the non-dissected long edge 101*f*. At this time, the tissue retaining portion 40 is made to retain the living tissue surface slightly, enabling stably retaining the living tissue fragment to be separated off.

Then, when the electrode 35 has reached the target dissection end position in the treatment target region as a result of the final dissection operation being performed from the state illustrated in FIGS. 21 and 22, the state turns into the state illustrated in FIG. 23. At this point of time, dissection of the non-dissected long edge 101*f* is completed. Consequently, the living tissue fragment that is the target of the resection procedure (living tissue including a lesion part such as a cancer) is separated off from the wall surface 101 of the organ 100, and the one-piece resection processing is completed (step S10 in FIG. 58).

Although the description of the first embodiment above, the third-round dissection operation is the final dissection operation, the present invention is not limited to this example. For example, if operations of the third round onwards are performed in a manner that is similar to the manner of the second-round dissection operation and the above-described final dissection operation is performed as a last dissection operation, a wider area of a living tissue can be resected.

Furthermore, although in the present embodiment, as a form of the electrode 35, an example configuration including a proximal end 35*a* provided so as to extend in the downward direction along the second axis Y and a beam portion 35*b* extending from an extremity of the proximal end 35*a* in the leftward direction along the first axis X has been indicated, the present invention is not limited to this form.

As a form of the electrode 35, the form being different from the above, for example, the electrode 35 can be configured by a beam portion 35*b* alone, the beam portion 35*b* extending from the facing surface 36*a* of the distal end rigid portion 36 in the leftward direction along the first axis X.

In the electrode unit 30 of the present embodiment, the electrode supporting portion 32 and the tissue retaining portion 40 are brought into abutment with a living tissue and then press the living tissue in a same direction, which makes a part of the living tissue, the part being between the electrode supporting portion 32 and the tissue retaining portion 40, deform into an outwardly bulging shape. Therefore, even the electrode 35 being formed so as to extend in the first axis X direction (horizontal direction) from the facing surface 36*a* of the distal end rigid portion 36 still enables resection of a living tissue that is stable in shape.

As described above, according to the first embodiment, in an electrode unit that performs treatment of a living tissue inside a body cavity, for example, more specifically, one-piece resection of a living tissue including a lesion part such as a cancer, using a high-frequency electric current, the electrode supporting portion 32 and the tissue retaining portion 40 are brought into abutment with the living tissue, enabling the electrode 35 supported by the electrode supporting portion 32 to be stable on a surface of the living tissue and also enabling restriction of a depth to which the electrode 35 penetrates in a depth direction from the surface of the living tissue. Consequently, there are no concerns of, e.g., the electrode 35 pierces a wall surface of the living tissue.

Furthermore, in this state, the electrode supporting portion 32 being slid from the distal end side (far end side) to the proximal end side in the longitudinal axis L direction enables the electrode 35 to be slid in the same direction to dissect the living tissue. Furthermore, at this time, the tissue retaining portion 40 moves in a direction that is the same as the direction of sliding of the electrode 35 while retaining the surface of the living tissue, enabling a resection target region to be kept stable. Therefore, an operation to dissect the living tissue via the electrode 35 can stably and reliably be performed. Then, mere repetition of such simple operation enables one-piece resection of a desired region of the living tissue.

Therefore, as a result of the above, the resected living tissue is in one piece. Therefore, use of a one-piece resected fragment (pathology specimen) enables, for example, efficient pathological diagnosis and can contribute to enhancement in accuracy of diagnosis.

Note that respective configurations of the electrode supporting portion, the electrode and the tissue retaining portion included in the electrode unit of the present invention are not limited to the example configurations indicated in the first embodiment described above. Various other example configurations of the first embodiment of the present invention will be described below.

First Modification

Figure 24:
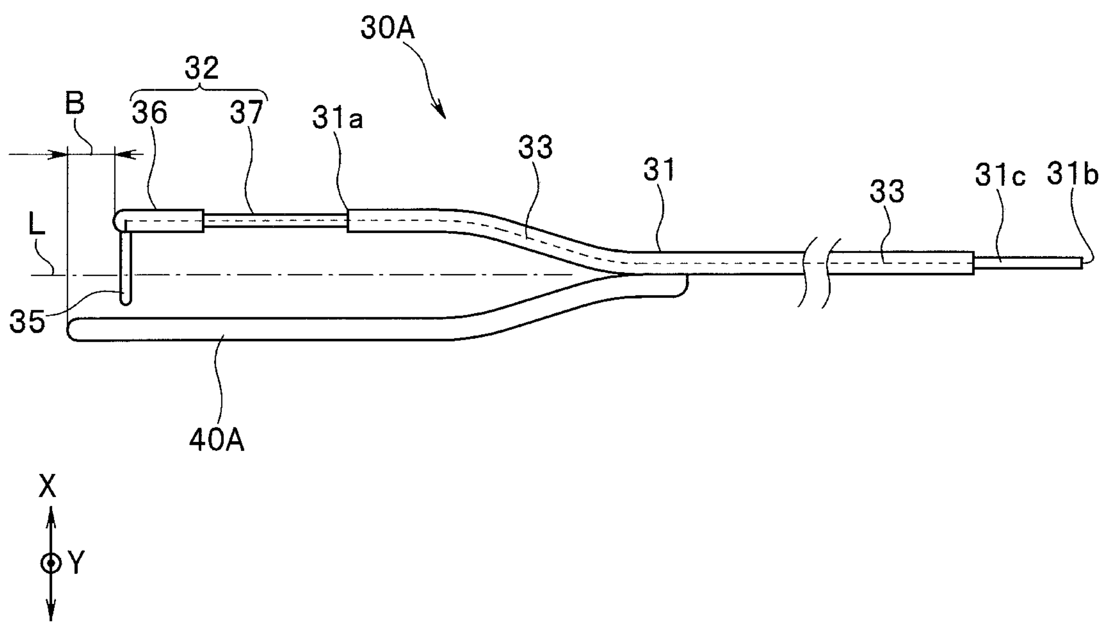
FIG. 24 is a plan view of an electrode unit of a first modification of the first embodiment of the present invention from the upper side.
Figure 25:
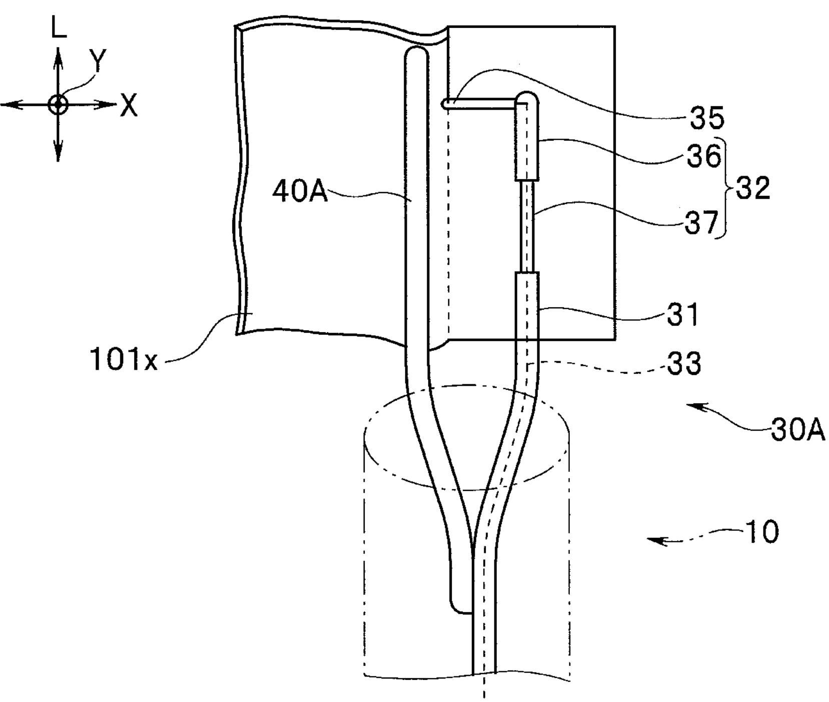
FIG. 25 is a schematic diagram illustrating a state of a final dissection operation when a living tissue inside a body cavity is resected in one piece using the electrode unit in FIG. 24.

FIGS. 24 and 25 are diagrams illustrating a first modification of the first embodiment of the present invention. Of the figures, FIG. 24 is a plan view of an electrode unit of the present modification from the upper side. FIG. 25 illustrates one-piece resection of a living tissue inside a body cavity using the electrode unit of the present modification. More specifically, FIG. 25 illustrates a state during a final dissection operation being performed.

As illustrated in FIG. 24, an electrode unit 30A of the present modification is different from the electrode unit 30 of the first embodiment in that a length dimension of a tissue retaining portion 40A is set to be longer than a length dimension of an electrode supporting portion 32.

In other words, the tissue retaining portion 40A in the present modification is formed so as to extend farther on the far end side than a distal end of the electrode supporting portion 32. In the example configuration in FIG. 24, the tissue retaining portion 40A is formed so as to extend farther on the far end side than the distal end of the electrode supporting portion 32 by the amount indicated by a sign B. The rest of configuration is similar to the configuration of the above-described first embodiment.

When one-piece resection of a living tissue is performed using the electrode unit 30A of the first modification, which is configured as described above, as illustrated in FIG. 25, the tissue retaining portion 40A can more reliably retain a dissected living tissue 101*x*.

Furthermore, in the electrode unit 30A of the present modification, a length of the tissue retaining portion 40A is set to be longer than the electrode supporting portion 32 by the amount indicated by the sign B, and thus, even when the electrode 35 has reached a dissection end position, a distal end of the tissue retaining portion 40A remains inside the living tissue 101*x* that has already been dissected.

Therefore, when dissection operations of a second round onwards are performed, the electrode 35 can be moved to a start point of a next dissection operation simply by sliding the electrode unit 30A from the proximal end side to the distal end side (far end side) as it is, with no need for operation to slide the tissue retaining portion 40A under the dissected living tissue 101*x*.

As described above, the electrode unit 30A of the present modification enables reliably and stably retaining the dissected living tissue 101*x* and enables contribution to enhancement in ease of handling.

Second Modification

Figure 26:
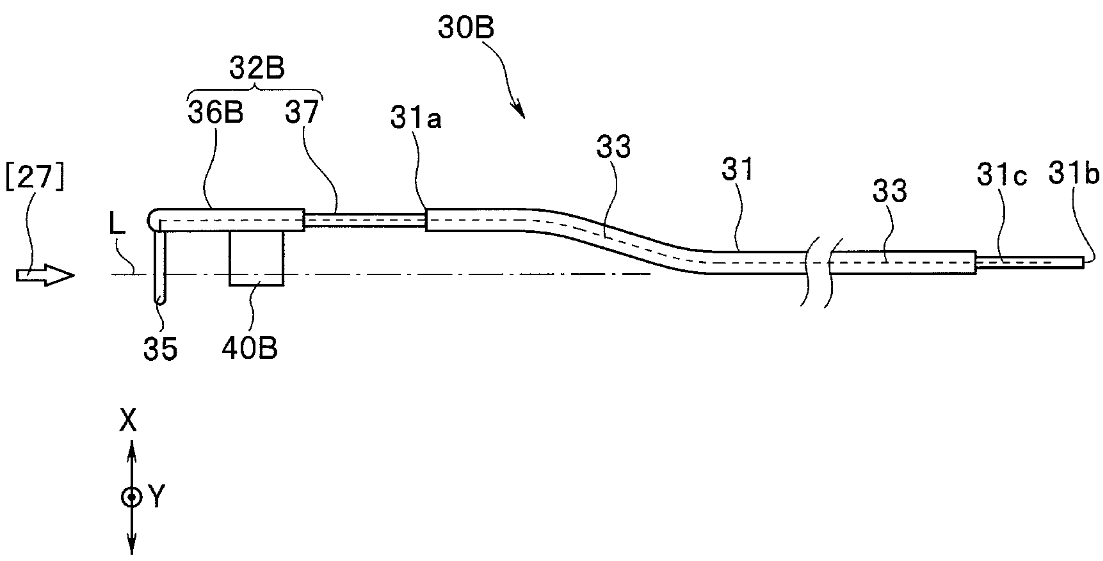
FIG. 26 is a plan view of an electrode unit of a second modification of the first embodiment of the present invention from the upper side.
Figure 27:
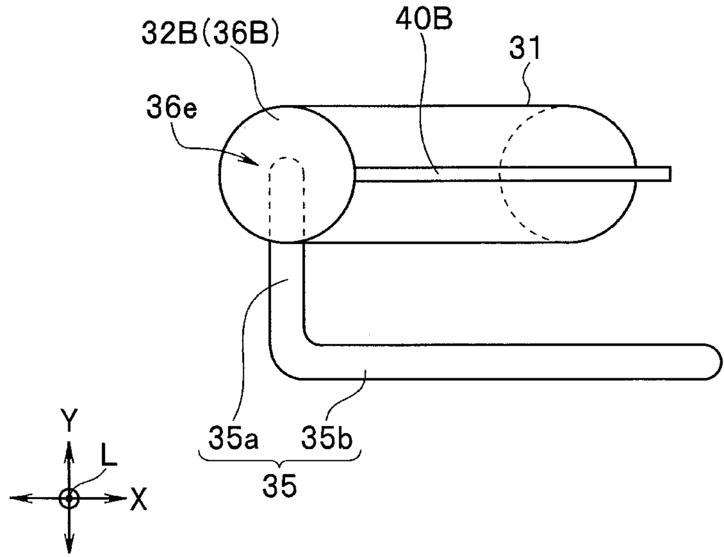
FIG. 27 is a front view in a direction of arrow [27] in FIG. 26.

FIGS. 26 and 27 are diagrams illustrating a second modification of the first embodiment of the present invention. Of the figures, FIG. 26 is a plan view of an electrode unit of the present modification from the upper side. FIG. 27 is a front view in a direction of arrow [27] in FIG. 26.

As illustrated in FIGS. 26 and 27, the electrode unit 30B of the present modification is different from the above-described first embodiment in form of a tissue retaining portion 40B.

In other words, the tissue retaining portion 40B in the electrode unit 30B of the present modification is provided at a distal end rigid portion 36B of an electrode supporting portion 32B. In this case, an entirety of tissue retaining portion 40B is formed in a plate shape. One end of the plate-shaped tissue retaining portion 40B is supported by the electrode supporting portion. The plate-shaped tissue retaining portion 40B extends in parallel with a beam portion 35*b* of an electrode 35 in a direction in which the beam portion 35*b* of the electrode 35 extends. Furthermore, in the example configuration of the present modification, the plate-shaped tissue retaining portion 40B is arranged at a position on the distal end rigid portion 36B, the position being closer to a proximal end of the distal end rigid portion 36B than the electrode 35 in the longitudinal axis L direction.

The plate-shaped tissue retaining portion 40B has a function that when the beam portion 35*b* of the electrode 35 penetrates into a living tissue from a surface of the living tissue, restricts a depth of the penetration in a depth direction of the electrode 35 from the surface of the living tissue and maintains a posture in a horizontal direction of the electrode 35 relative to the living tissue surface. The rest of configuration is similar to the configuration of the above-described first embodiment.

When one-piece resection of a living tissue is performed using the electrode unit 30B of the second modification, which is configured as above, the tissue retaining portion 40B more reliably retains the living tissue (not illustrated) immediately before dissection by the electrode 35, enabling stably performing an operation to resect the living tissue.

Third Modification

Figure 28:
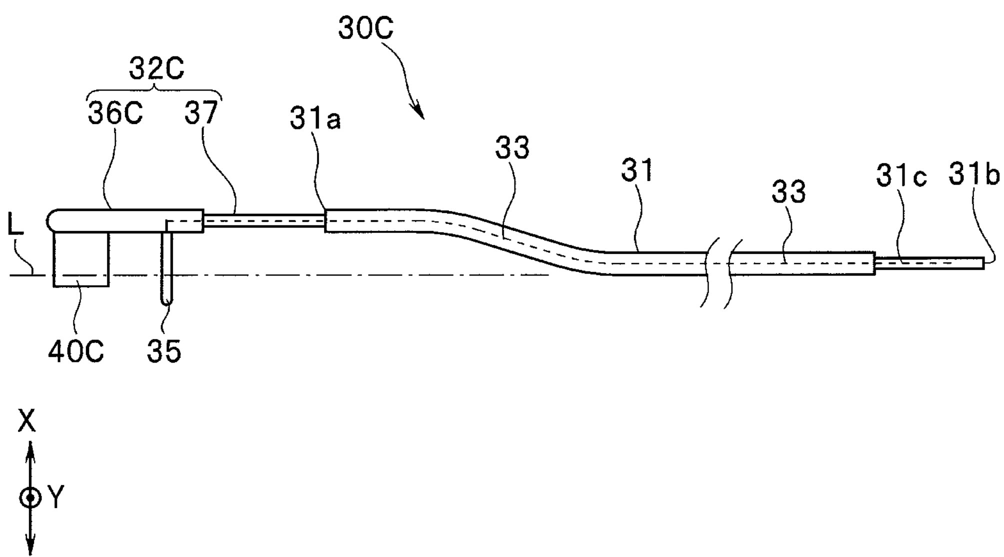
FIG. 28 is a plan view of an electrode unit of a third modification of the first embodiment of the present invention from the upper side.
Figure 29:
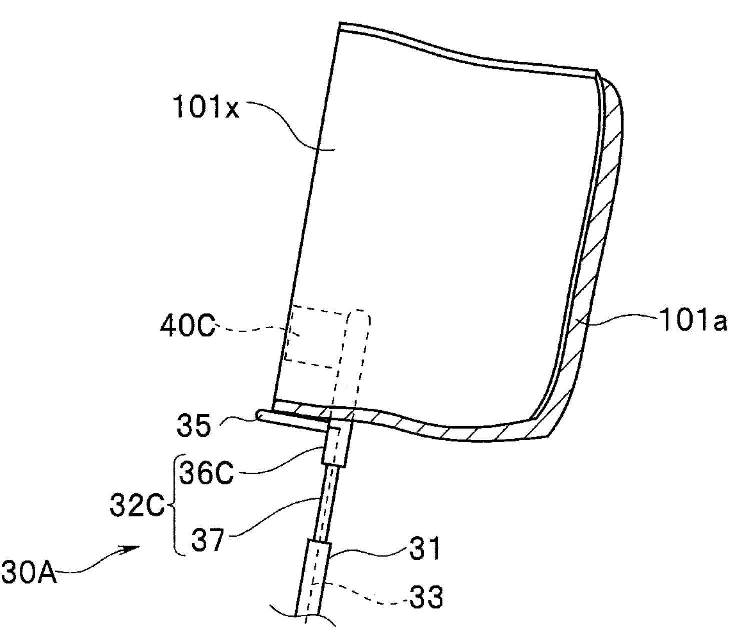
FIG. 29 is a schematic diagram illustrating a state of a final dissection operation when a living tissue inside a body cavity is resected in one piece using the electrode unit in FIG. 28.

FIGS. 28 and 29 are diagrams illustrating a third modification of the first embodiment of the present invention. Of the figures, FIG. 28 is a plan view of an electrode unit of the present modification from the upper side. FIG. 29 illustrates one-piece resection of a living tissue inside a body cavity using the electrode unit of the present modification. FIG. 29 specifically illustrates a state during a final dissection operation being performed.

As illustrated in FIGS. 28 and 29, an electrode unit 30C of the present modification is different from the second modification only in disposition of a tissue retaining portion 40C.

The tissue retaining portion 40C of the electrode unit 30C of the present modification is similar to the second modification in that tissue retaining portion 40C is provided at a distal end rigid portion 36C of an electrode supporting portion 32C.

In the example configuration of the present modification, the plate-shaped tissue retaining portion 40C is arranged at a position on the distal end rigid portion 36C, the position being closer to a far end (distal end) of the distal end rigid portion 36C than an electrode 35 in the longitudinal axis L direction.

The plate-shaped tissue retaining portion 40C is similar to the second modification also in having a function that when a beam portion 35*b* of the electrode 35 penetrates into a living tissue from a surface of the living tissue, restricts a depth of the penetration in a depth direction of the electrode 35 from the surface of the living tissue and maintains a posture in a horizontal direction of the electrode 35 relative to the living tissue surface. The rest of configuration is similar to the above-described configuration of the first embodiment.

When one-piece resection of a living tissue is performed using the electrode unit 30C of the third modification, which is configured as above, as with the second modification above, the tissue retaining portion 40C more reliably retains a living tissue 101*x* in a region immediately subsequent to dissection by the electrode 35, enabling stably performing an operation to resect the living tissue. In addition, the configuration of the present modification enables provision of effects that are similar to the effects of the first modification because of the tissue retaining portion 40C being provided at a position closer to the distal end than the electrode 35.

Shapes and sizes (plate areas) of the plate-shaped tissue retaining portions 40B, 40C in the second and third modifications are not limited to the examples illustrated in the figures and may appropriately be set according to an object to be subjected to a procedure and/or a type of the procedure.

Fourth Modification

Figure 30:
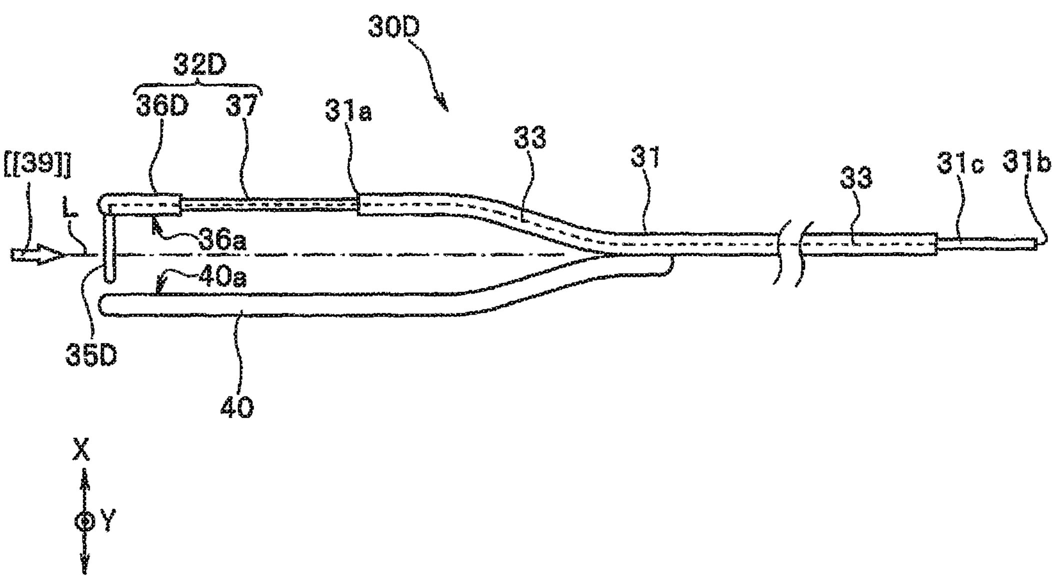
FIG. 30 is a plan view of an electrode unit of a fourth modification of the first embodiment of the present invention from the upper side.
Figure 31:
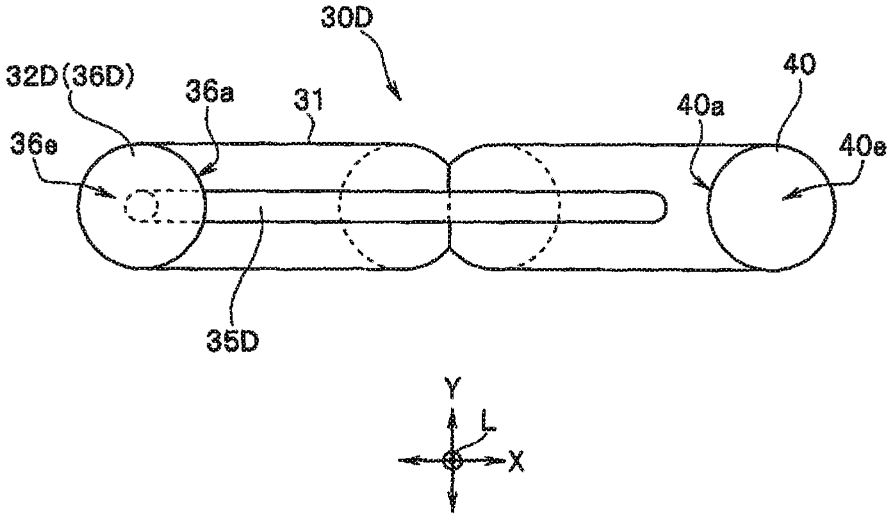
FIG. 31 is a front view in a direction of arrow [39] in FIG. 30.
Figure 32:
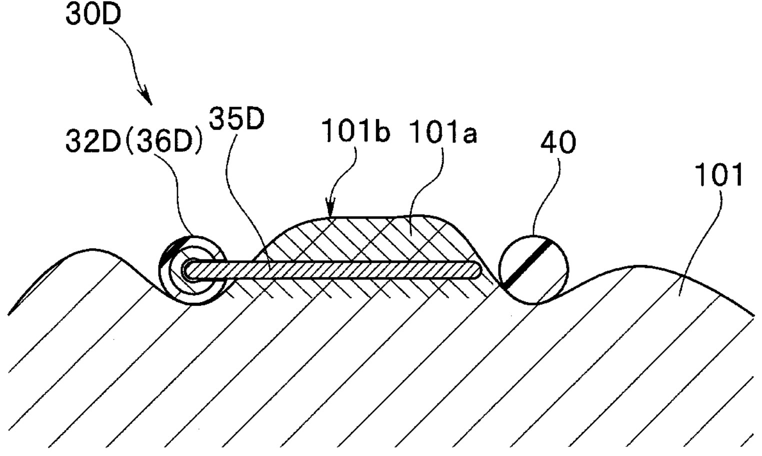
FIG. 32 is a sectional view illustrating a state at a time of one-piece resection of a living tissue inside a body cavity using the electrode unit in FIG. 30.

FIGS. 30 to 32 are diagrams illustrating a fourth modification of the first embodiment of the present invention. Of the figures, FIG. 30 is a plan view of an electrode unit of the present modification from the upper side. FIG. 31 is a front view in a direction of arrow [39] in FIG. 30. FIG. 32 is a sectional view illustrating a state of one-piece resection of a living tissue inside a body cavity using the electrode unit of the present modification.

As illustrated in FIGS. 30 and 31, an electrode unit 30D of the present modification is different from the configurations of the first embodiment and the respective modifications in shape of an electrode 35D.

The electrode 35D in the electrode unit 30D of the present modification extends from a facing surface 36*a* of a distal end rigid portion 36D of an electrode supporting portion 32D substantially horizontally toward a facing surface 40*a* of a tissue retaining portion 40. The rest of configuration is similar to the configuration of the first embodiment.

When one-piece resection of a living tissue is performed using the electrode unit 30D of the fourth modification, which is configured as above, first, the electrode supporting portion 32D and the tissue retaining portion 40 of the electrode unit 30D are brought into abutment with, and then pressed against, a living tissue surface.

When the pressing of the electrode unit 30D against the living tissue is continued, in due course, the electrode 35D comes into abutment with the living tissue surface. At this time, if a high-frequency electric current flows in the electrode 35D, the electrode 35D cauterizes the living tissue.

When a pressing force is applied to the electrode unit 30D in the same direction in such state, the electrode 35D penetrates into the living tissue while cauterizing the tissue. Concurrently, as illustrated in FIG. 32, a part of the living tissue, the part being between the electrode supporting portion 32D and the tissue retaining portion 40, deforms into a bulging shape projecting outwardly from the tissue surface (see sign 101*b*).

In this state, the electrode unit 30D is slid from the distal end side to the proximal end side. Consequently, the electrode 35D is also slid in a direction that is the same as the direction of the sliding of the electrode unit 30D. At this time, the electrode 35D dissects the living tissue in the bulging shape portion 101*b*.

As described above, when one-piece resection is performed using an electrode unit of any of the first embodiment of the present invention and the respective modifications, a dissection operation is performed a plurality of times. In this case, a thickness of a resected fragment in each dissection operation (depth to which the electrode penetrates into a tissue) depends on a pressing force provided by a user. Therefore, even a same user may cause a difference in level at a seam part between dissected regions in the respective dissection operations.

The configuration of the present modification is made so as to substantially horizontally dissect the vicinity of a bottom edge of the bulging shape portion 101*b*, enabling one-piece resection to an even depth to be performed without causing such level difference and thus enabling acquisition of a resected fragment including a smooth dissection surface.

Fifth Modification

Figure 33:
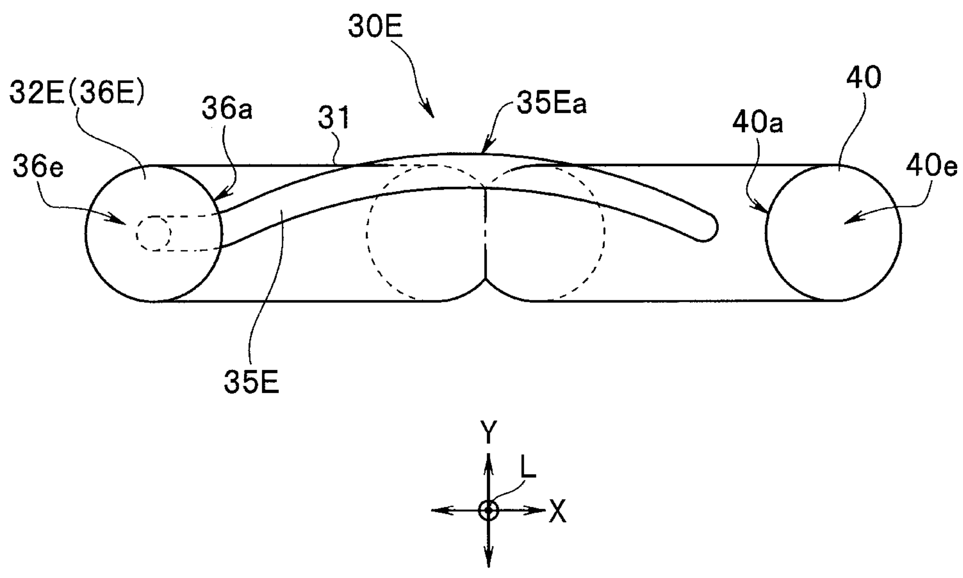
FIG. 33 is a front view of an electrode unit of a fifth modification of the first embodiment of the present invention in a direction along a longitudinal axis L.
Figure 34:
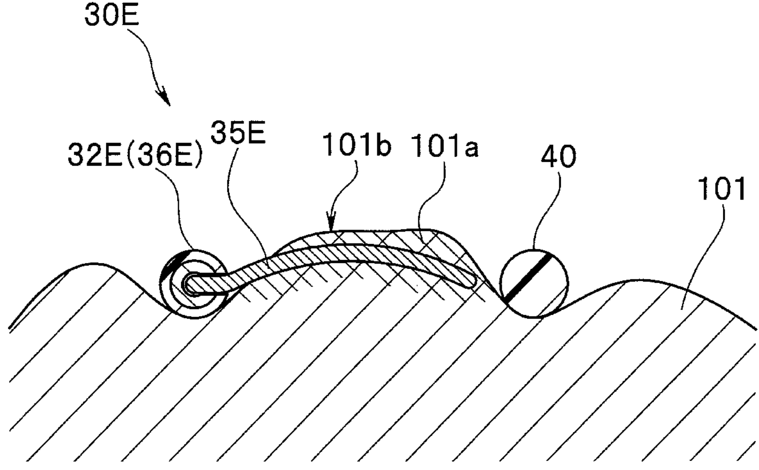
FIG. 34 is a sectional view illustrating a state at a time of one-piece resection of a living tissue inside a body cavity using the electrode unit in FIG. 33.

FIGS. 33 and 34 are diagrams illustrating a fifth modification of the first embodiment of the present invention. Of the figures, FIG. 33 is a front view in a direction along the longitudinal axis L (direction corresponding to a direction of arrow [39] in FIG. 30 referred to in the fourth modification). FIG. 34 is a sectional view illustrating one-piece resection of a living tissue inside a body cavity using an electrode unit of the present modification. Note that a plan view of the electrode unit according to the present modification from the upper side is similar to FIG. 30 referred to in the fourth modification and thus is omitted.

An electrode unit 30E of the present modification is basically similar in configuration to the fourth modification described above. As illustrated in FIG. 33, the present modification is slightly different from the fourth modification only in shape of an electrode 35E.

The electrode 35E of the electrode unit 30E of the present modification includes a convex bent portion 35Ea substantially horizontally extending from a facing surface 36*a* of a distal end rigid portion 36E of an electrode supporting portion 32E toward a facing surface 40*a* of a tissue retaining portion 40 and is then bent in a shape that is convex in an upward direction.

In other words, the convex bent portion 35Ea of the electrode 35E is bent in a shape that is convex in the upward direction as viewed in the direction along the longitudinal axis L (from the front side). The rest of configuration is similar to the above-described configuration of the first embodiment.

Operation when one-piece resection of a living tissue is performed using the electrode unit 30E of the fifth modification, which is configured as described above, is similar to the above-described operation of the fourth modification. In other words, first, as in the fourth modification, the electrode supporting portion 32E and the tissue retaining portion 40 of the electrode unit 30E are brought into abutment with, and then pressed against, a living tissue surface. When the pressing of the electrode unit 30E against the living tissue is continued, in due course, the electrode 35E comes into abutment with the living tissue surface. At this time, if a high-frequency electric current flows in the electrode 35E, the electrode 35E cauterizes the living tissue.

When a pressing force is applied to the electrode unit 30E in the same direction in such state, the electrode 35E penetrates into the living tissue while cauterizing the tissue. Concurrently, a part of the living tissue, the part being between the electrode supporting portion 32E and the tissue retaining portion 40, deforms into a bulging shape projecting outwardly from the tissue surface (see sign 101*b* in FIG. 34).

In this state, the electrode unit 30E is slid from the distal end side to the proximal end side. Consequently, the electrode 35E is also slid in a direction that is the same as the direction of the sliding of the electrode unit 30E. At this time, the electrode 35E dissects the living tissue in the bulging shape portion 101*b*. As described above, the electrode 35E in the present modification includes the convex bent portion 35Ea projecting in the upward direction. When the electrode 35E is slid from the distal end side to the proximal end side, the convex bent portion 35Ea dissects the living tissue along an inner surface of the bulging shape portion 101*b*.

Therefore, the configuration of the present modification also enables one-piece resection to be performed without causing a level difference at a seam part between dissected regions generated as a result of a plurality of dissection operations being performed and thus enables acquisition of a resected fragment including a smooth dissection surface.

Sixth Modification

Figure 35:
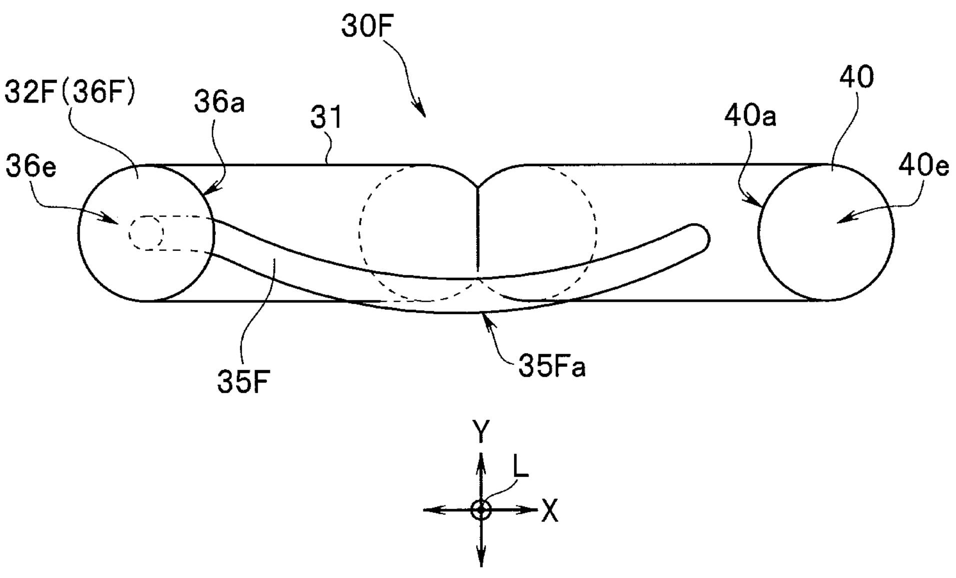
FIG. 35 is a front view of an electrode unit of a sixth modification of the first embodiment of the present invention in a direction along the longitudinal axis L.
Figure 36:
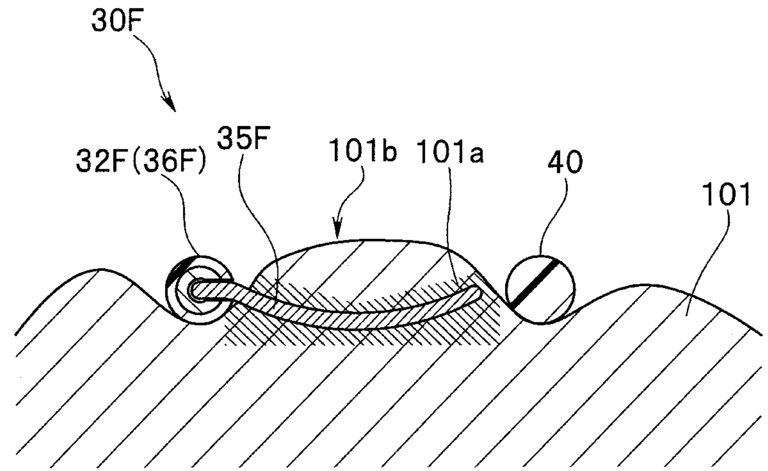
FIG. 36 is a sectional view illustrating a state at a time of one-piece resection of a living tissue inside a body cavity using the electrode unit in FIG. 35.

FIGS. 35 and 36 are diagrams illustrating a sixth modification of the first embodiment of the present invention. Of the figures, FIG. 35 is a front view in a direction along a longitudinal axis L (direction corresponding to the direction of arrow [39] in FIG. 30 referred to in the fourth modification). FIG. 36 is a sectional view of a state of one-piece resection of a living tissue inside a body cavity using an electrode unit of the present modification. Note that a plan view of the electrode unit of the present modification from the upper side is similar to FIG. 30 referred to in the fourth modification and thus is omitted.

An electrode unit 30F of the present modification is basically similar in configuration to the fourth and fifth modifications described above. As illustrated in FIG. 35, the present modification is slightly different from the fourth and fifth modifications only in shape of an electrode 35F.

The electrode 35F of the electrode unit 30F of the present modification includes a convex bent portion 35Fa substantially horizontally extending from a facing surface 36*a* of a distal end rigid portion 36F of an electrode supporting portion 32F toward a facing surface 40*a* of a tissue retaining portion 40 and is then bent in a shape that is convex in a downward direction.

In other words, the convex bent portion 35Fa of the electrode 35F is bent in a shape that is convex in the downward direction as viewed in the direction along the longitudinal axis L (from the front side). The rest of configuration is similar to the above-described configuration of the first embodiment.

Operation when one-piece resection of a living tissue is performed using the electrode unit 30F of the sixth modification, which is configured as described above, is similar to the above-described operation of the fifth modification. In other words, first, as in the fifth modification, the electrode supporting portion 32F and the tissue retaining portion 40 of the electrode unit 30F are brought into abutment with, and then, pressed against, a living tissue surface. When the pressing of the electrode unit 30F against the living tissue is continued, in due course, the electrode 35F comes into abutment with the living tissue surface. At this time, if a high-frequency electric current flows in the electrode 35F, the electrode 35F cauterizes the living tissue.

When a pressing force is applied to the electrode unit 30F in the same direction in such state, the electrode 35F penetrates into the living tissue while cauterizing the tissue. Concurrently, a part of the living tissue, the part being between the electrode supporting portion 32F and the tissue retaining portion 40, deforms into a bulging shape projecting outwardly from the tissue surface (see sign 101*b* in FIG. 36).

In this state, the electrode unit 30F is slid from the distal end side to the proximal end side. Consequently, the electrode 35F is also slid in a direction that is the same as the direction of the sliding of the electrode unit 30F. At this time, the electrode 35F dissects the living tissue in the bulging shape portion 101*b*. As described above, the electrode 35F in the present modification includes a convex bent portion 35Fa projecting in the downward direction. When the electrode 35F is slid from the distal end side to the proximal end side, the convex bent portion 35Fa dissects the living tissue along a bent surface that is away from an inner surface of the bulging shape portion 101*b*.

Therefore, the configuration of the present modification also enables one-piece resection to an even depth to be performed without causing a level difference at a seam part between dissected regions generated as a result of a plurality of dissection operations being performed and thus enabling acquisition of a resected fragment including a smooth dissection surface, the resected fragment resulting from dissection to a constant depth in which a muscle layer is included.

Seventh Modification

Figure 37:
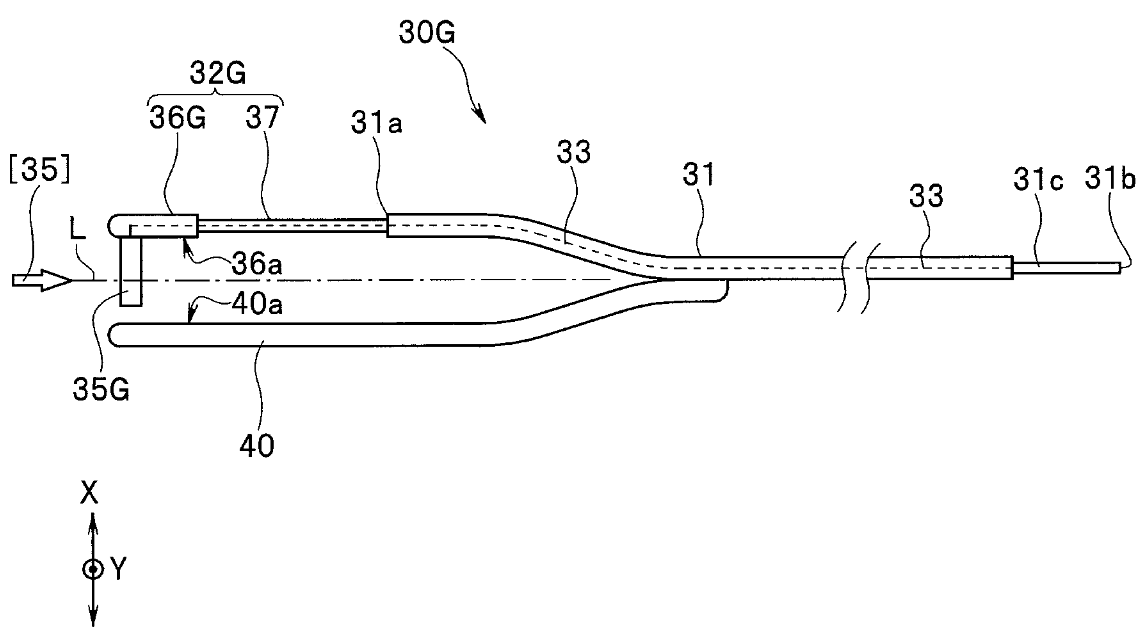
FIG. 37 is a plan view of an electrode unit of a seventh modification of the first embodiment of the present invention from the upper side.
Figure 38:
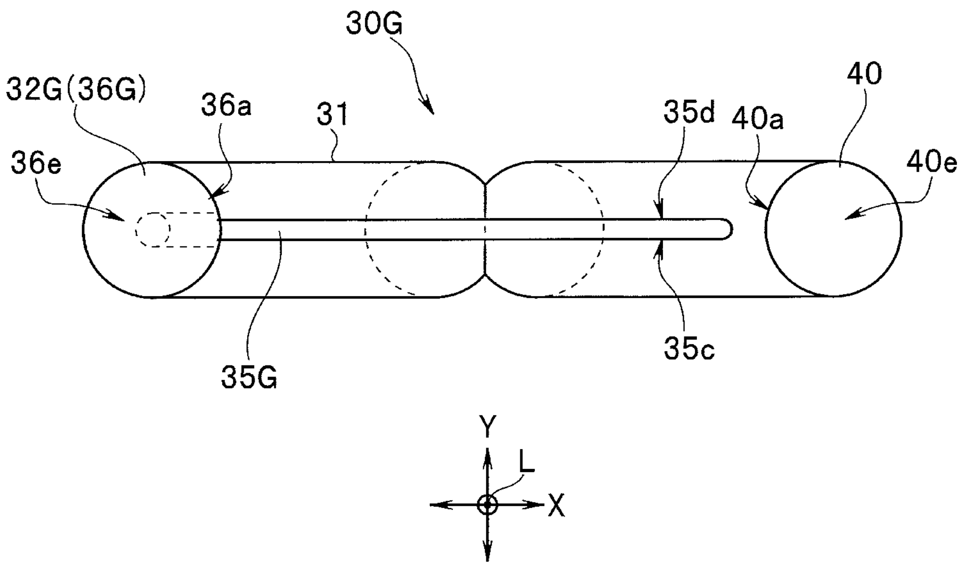
FIG. 38 is a front view of the electrode unit in FIG. 37 in a direction along the longitudinal axis L.

FIGS. 37 and 38 are diagrams illustrating a seventh modification of the first embodiment of the present invention. Of the figures, FIG. 37 is a plan view of an electrode unit of the present modification from the upper side. FIG. 38 is a front view in a direction along a longitudinal axis L (direction corresponding to the direction of arrow [39] in FIG. 30 referred to in the fourth modification).

As illustrated in FIGS. 37 and 38, an electrode unit 30G of the present modification is different from the first embodiment and the respective modifications described above in shape of an electrode 35G.

The electrode 35G of the electrode unit 30G of the present modification includes a strip-shaped member substantially horizontally extending from a facing surface 36*a* of a distal end rigid portion 36G of an electrode supporting portion 32G toward a facing surface 40*a* of a tissue retaining portion 40, the strip-shaped member having a width dimension.

Although the electrodes in the first embodiment and the respective modifications described above each indicate an example configuration in which a linear member or a rod-shaped member provided so as to be continuous with an electrode wire 33 is employed, in the electrode 35G in the present modification, instead of such example configuration, a strip-shaped member is employed. The electrode 35G in the present modification has electrical conductivity and also has rigidity. In order to have a predetermined rigidity, it is desirable that the electrode 35G including the strip-shaped member has, for example, a width dimension of around 1 to 2 mm and a predetermined thickness dimension (at least 0.5 mm or more).

Because of the electrode 35G being configured in a cantilevered form, when the electrode 35G is pressed against a surface of a living tissue, the electrode 35G may be flexed. In such case, resection processing via the electrode 35G is unstable, which may cause the problem of a failure to perform resection to a desired depth (thickness). The configuration of the present modification is a contrivance to eliminate such problem.

In other words, in the present modification, configuring the electrode 35G using an electrically conductive member having rigidity and including a strip-shaped member enables more reliably performing stable resection processing. The rest of configuration is similar to the above-described configuration of the first embodiment. The configuration of the present modification also enables provision of effects that are similar to the effects of the first embodiment and the respective modifications described above.

Although the present modification indicates an example in which a strip-shaped member having rigidity is employed as the electrode 35G, the present invention is not limited to this example configuration. For example, in comparison with the electrode (having a diameter of around 0.5 mm) used in the above first embodiment, etc., the electrode 35G may be configured by a thick linear member or a rod-shaped member having a diameter of around 1 to 2 mm. In this case, also, effects that are similar to the effects of the seventh modification can be achieved.

Furthermore, the following component may be added to the electrode 35G in the seventh modification.

The electrode 35G in the seventh modification indicates an example in which the electrode 35G is configured using a strip-shaped member or a thick linear member having rigidity. In the electrode 35G having such configuration, an insulating coating is formed on some of surfaces of the electrode 35G.

A surface of the electrode 35G, the surface being provided with the insulating coating, is a surface (sign 35*d* in FIG. 38, that is, an upper surface) of the electrode 35G, the surface being not a surface (sign 35*c* in FIG. 38, that is, a lower surface) of the electrode 35G, the surface being is brought into direct abutment with a living tissue and used to perform dissection when one-piece resection treatment is performed using the electrode unit 30G.

In other words, when one-piece resection treatment is performed, first, one surface (lower surface 35*c*) of the electrode 35G is disposed so as to face a surface of a living tissue and the lower surface 35*c* is then brought into abutment with the surface of the living tissue. At this time, the lower surface 35*c* of the electrode 35G cauterizes the living tissue by making the living tissue generate heat. Consequently, the electrode 35G penetrates into the living tissue from the surface of the tissue while cauterizing the tissue. Therefore, from among the surfaces of the electrode 35G, the lower surface 35*c* to be brought into contact with a surface of a living tissue is not provided with the insulating coating.

On the other hand, another surface of the surfaces of the electrode 35G, that is, the upper surface 35*d* that when the lower surface 35*c* of the electrode 35G is brought into contact with a surface of a living tissue, is not in contact with the surface of the living tissue is provided with the insulating coating.

This configuration allows, when one-piece resection treatment is performed using the electrode unit 30G, from among the surfaces of the electrode 35G, the upper surface 35*d* provided with the insulating coating to be brought into contact with an inner surface of a resected fragment after the resected fragment being separated off from a wall surface of a living tissue. However, operation of the insulating coating provided on the surface 35*d* enables curbing thermal invasion of the resected fragment (that is, a pathology specimen).

Second Embodiment

Next, a second embodiment of the present invention will be described below. An electrode unit 30H of the present embodiment is basically similar in configuration to the first embodiment described above. The electrode unit 30H of the present embodiment is different from the first embodiment only in configuration of a distal end rigid portion 36H of an electrode supporting portion 32H and an electrode 35H and in configuration of a tissue retaining portion 40H. Therefore, components that are similar to the above-described components in the first embodiment will be provided with signs that are the same as the signs of the components in the first embodiment and description of such components will be omitted, and only parts that are different from the first embodiment will be described.

Figure 39:
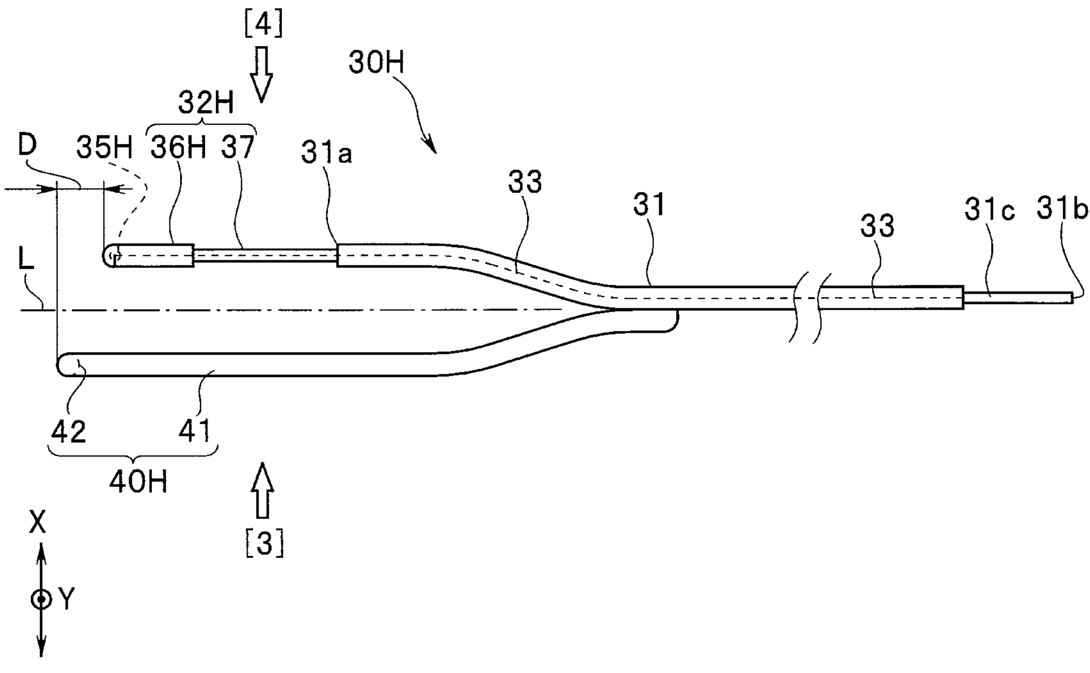
FIG. 39 is a plan view of an electrode unit of a second embodiment of the present invention from the upper side.
Figure 40:
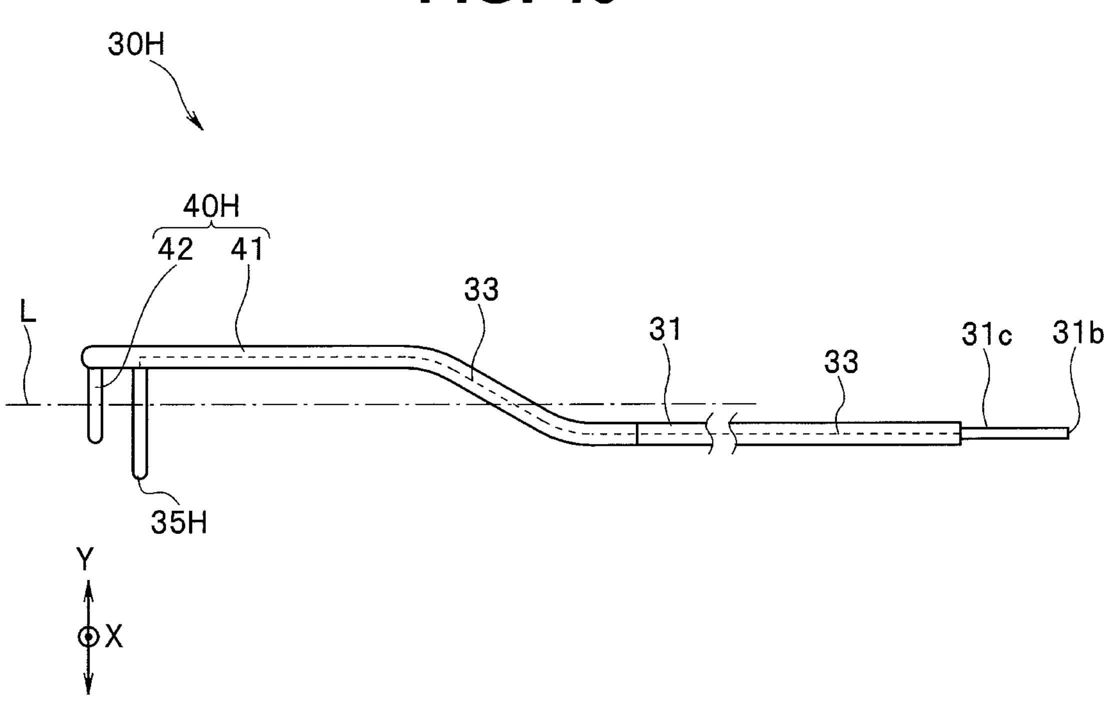
FIG. 40 is a left side view in a direction of arrow [40] in FIG. 39.
Figure 41:
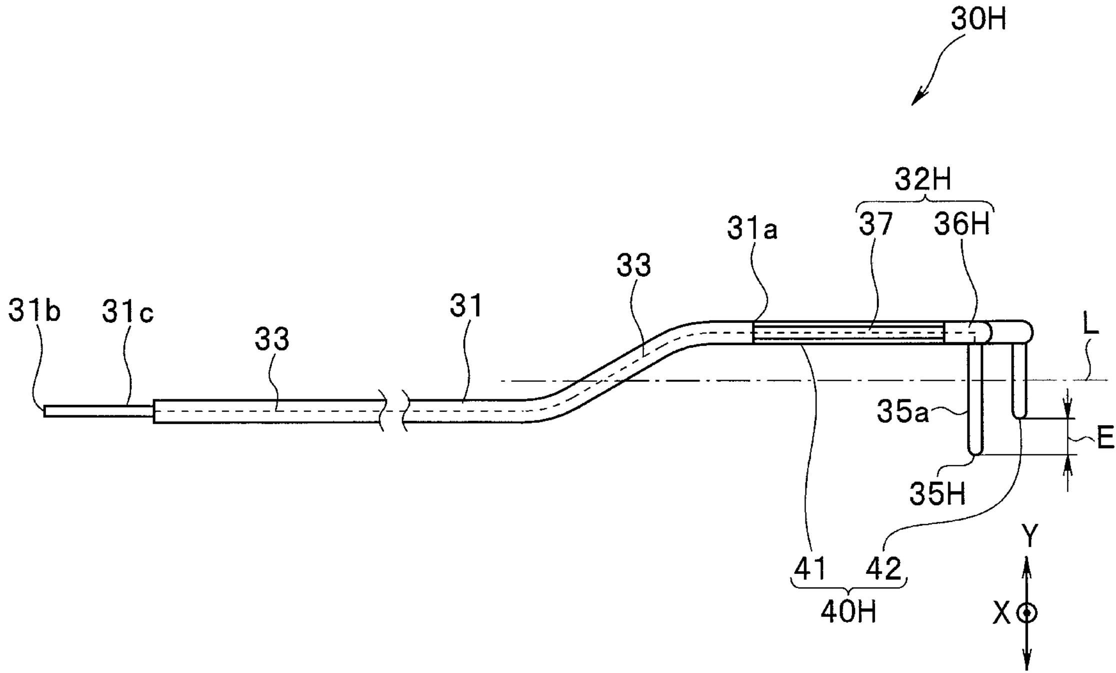
FIG. 41 is a right side view in a direction of arrow [41] in FIG. 39.

FIGS. 39 to 41 are diagrams illustrating an electrode unit of a second embodiment of the present invention. Of the figures, FIG. 39 is a plan view of the electrode unit of the present embodiment from the upper side. FIG. 40 is a left side view of the electrode unit of the present embodiment. In other words, FIG. 40 is a diagram of the electrode unit as viewed in a direction of arrow [40] in FIG. 39. FIG. 41 is a right side view of the electrode unit of the present embodiment. In other words, FIG. 41 is a diagram of the electrode unit as viewed in a direction of arrow [41] in FIG. 39.

As illustrated in FIGS. 39 to 41, the electrode unit 30H of the present embodiment has an elongated shape with a direction along the longitudinal axis L as a longitudinal direction. The electrode unit 30H mainly includes, e.g., a proximal end rigid portion 31, an electrode supporting portion 32H, an electrode wire 33, an electrode 35H and a tissue retaining portion 40H.

The electrode supporting portion 32H is a component portion that fixes and supports a proximal end 35*a* (see FIG. 41) of the electrode 35H. In this case, the electrode supporting portion 32H is formed in a substantially straight shape in an entirety and fixedly supports the proximal end 35*a* of the electrode 35H in a distal end part. The electrode supporting portion 32H is disposed in parallel with the tissue retaining portion 40H.

The electrode supporting portion 32H includes a distal end rigid portion 36H and an elastic region 37. Of these portions, the distal end rigid portion 36H is a component portion having a hollow columnar outer shape with the direction along the longitudinal axis L as a longitudinal direction. The distal end rigid portion 36H includes a material having an electrical insulating property. An electrode wire 33 is inserted through the distal end rigid portion 36H and the electrode wire 33 is electrically connected to the electrode 35H fixedly supported in the vicinity of a distal end portion.

The electrode 35H includes the proximal end 35*a* projecting from a surface of the distal end rigid portion 36H and is disposed in a cantilevered manner. In more detail, the proximal end 35*a* of the electrode 35H is provided so as to project outward from a part close to a distal end of the distal end rigid portion 36H and extend a predetermined length in a downward direction along a second axis Y. As described later, a length of projection of the electrode 35H from the surface of the distal end rigid portion 36H is prescribed based on a relationship with a length of the tissue retaining portion 40H that serves as a stopper (which will be described in detail later).

On the other hand, the tissue retaining portion 40H includes a rod-shaped portion 41 having a substantially straight shape in an entirety, the rod-shaped portion 41 having elasticity in an entirety and including a non-electrically conductive material, and a flexed portion 42 flexed in the downward direction along the second axis Y from the vicinity of a distal end of the rod-shaped portion 41, the flexed portion 42 extending a predetermined length in the downward direction. In the tissue retaining portion 40H, a distal end region including the flexed portion 42 is a free end and a proximal end is fixedly supported by one side surface portion close to a distal end of the proximal end rigid portion 31. This configuration makes the tissue retaining portion 40H be formed in a cantilevered shape.

In more detail, the rod-shaped portion 41 of the tissue retaining portion 40H is disposed substantially in parallel with the electrode supporting portion 32H so as to extend along the longitudinal axis L. In this case, a length of extension in the direction along the longitudinal axis L of the tissue retaining portion 40H is set to be longer than a length of extension in the direction along the longitudinal axis L of the electrode supporting portion 32H by an amount of dimension indicated by sign D illustrated in FIGS. 39 to 41.

Here, a length dimension difference D in the longitudinal axis L direction between the electrode supporting portion 32H and the tissue retaining portion 40H is set as follows. As described later, during one-piece resection treatment being performed using the electrode unit 30H of the present embodiment, the electrode unit 30H is used such that a part of a resected fragment (pathology specimen) that is a treatment target is held between the electrode supporting portion 32H and the tissue retaining portion 40H. The length dimension difference D between the electrode supporting portion 32H and the tissue retaining portion 40H is set to be a length enough to, in the above case, prevent the living tissue from coming off from between the electrode supporting portion 32H and the tissue retaining portion 40H.

The second embodiment is similar to the above-described first embodiment in that the electrode supporting portion 32H and the tissue retaining portion 40H are disposed with a predetermined space from each other in a direction along a first axis X (left-right direction of the electrode unit 30). In this case, the space in the direction along the first axis X between the electrode supporting portion 32H and the tissue retaining portion 40H is set to be around 1 to 2 mm longer than a thickness of a fragment resected from a living tissue. This is because during use of the electrode unit 30H, an operation of holding a resected fragment between the electrode supporting portion 32H and the tissue retaining portion 40H in a thickness direction is performed (details of a procedure of the operation will be described later).

Furthermore, a length of projection of the electrode 35H from the surface of the distal end rigid portion 36H is set to be longer than a length of the flexed portion 42 of the tissue retaining portion 40H by an amount of dimension indicated by sign E in FIG. 41.

Here, the length dimension difference amount E in the second axis Y direction between the electrode 35H and the flexed portion 42 is set as follows. As described later, during one-piece resection treatment being performed using the electrode unit 30H of the present embodiment, the flexed portion 42 of the tissue retaining portion 40H comes into abutment with a surface of a living tissue, the surface being in the vicinity of a resected fragment (pathology specimen) that is a treatment target, preventing the electrode 35H from overly penetrating into the living tissue (stopper function). In this case, respective length dimensions of the electrode 35H and the flexed portion 42, that is, a length dimension difference amount E, are set (see FIG. 43 referred to later) such that when the flexed portion 42 is brought into abutment with the surface of the living tissue and pressed against the living tissue surface with a predetermined amount of force, a distal end of the electrode 35H that has penetrated in the living tissue is inserted in the muscle layer. The rest of configuration is similar to the above-described configuration of the first embodiment.

An operation and procedure of one-piece resection treatment of a living tissue in a predetermined region including a lesion part inside an organ 100 of a subject using the endoscope system 1 including the electrode unit 30H of the present embodiment, which is configured as above, will be described below with reference to FIGS. 42 to 57 and 59.

The example treatment procedure described in the present embodiment is an example of a case where one-piece resection treatment in which a living tissue that is a treatment target (living tissue including a lesion part, for example, a cancer) is resected such that the living tissue is shaped in a block is performed. This is the same as the first embodiment.

Figure 42:
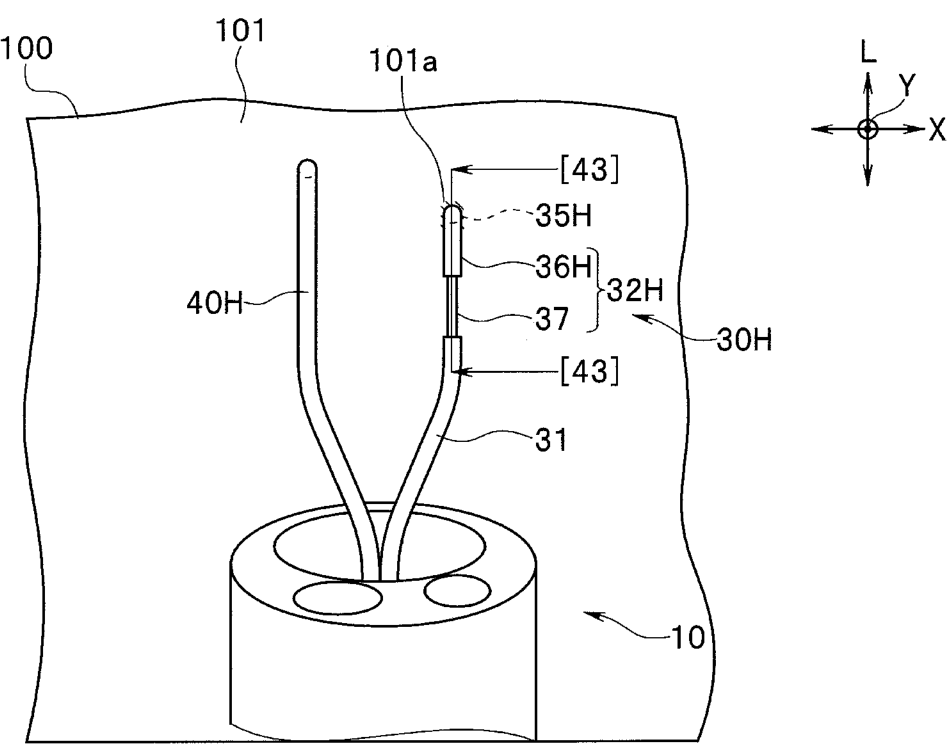
FIG. 42 is a schematic diagram illustrating a procedure for performing one-piece resection processing using a resectoscope to which the electrode unit of the second embodiment of the present invention is applied.
Figure 43:
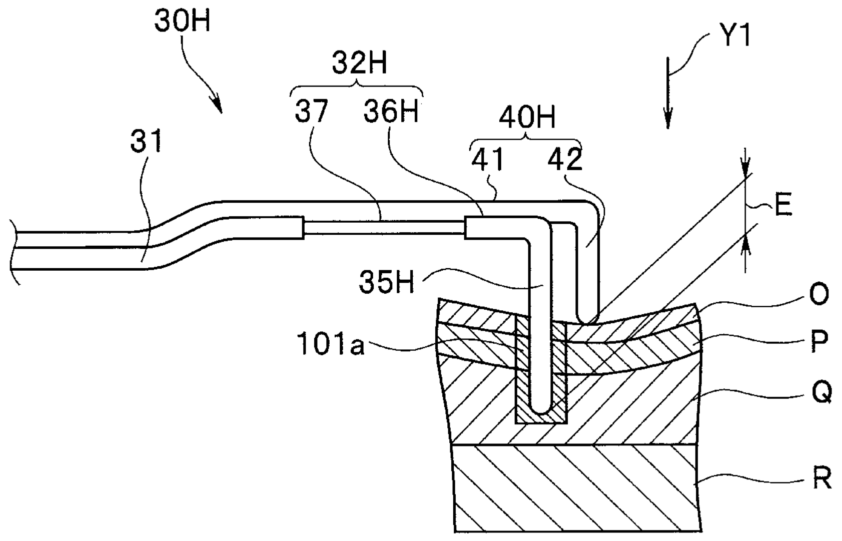
FIG. 43 is a schematic diagram illustrating a section along a line [43]-[43] in FIG. 42.
Figure 59:
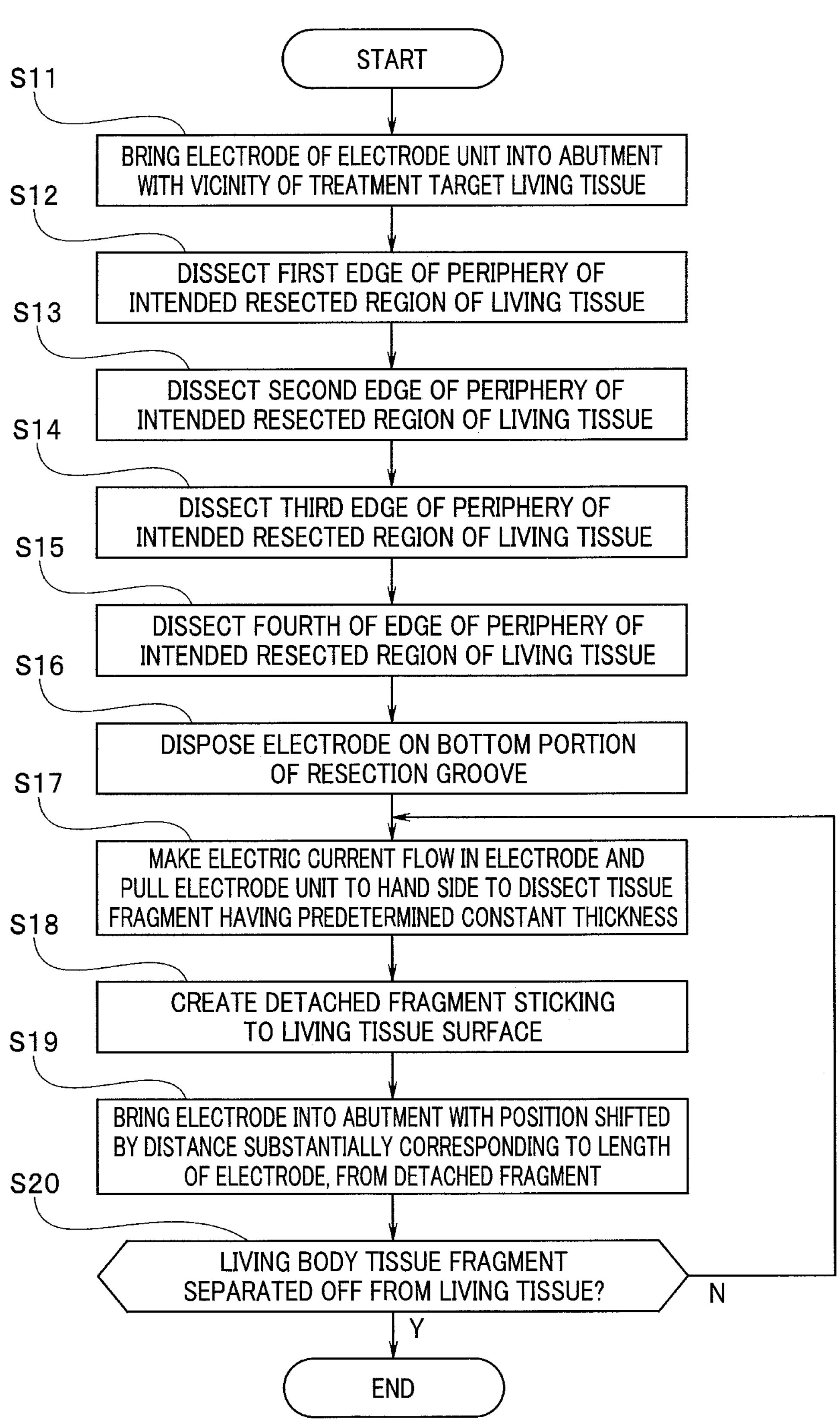
FIG. 59 is a flowchart illustrating a procedure for treatment performed using the resectoscope to which the electrode unit of the second embodiment of the present invention is applied.

FIGS. 42 to 57 are diagrams schematically illustrating a procedure for performing treatment of a living tissue inside a body cavity (organ) of a subject such as a human body using a resectoscope to which the electrode unit of the present embodiment is applied. From among the figures, FIG. 42 is a schematic diagram illustrating a state in which the resectoscope to which the electrode unit of the present embodiment is applied is inserted inside a body cavity (organ) of a subject such as a human body with an electrode brought into abutment with a predetermined position. FIG. 43 is a sectional view illustrating a section along a line [43]-[43] in FIG. 42. Furthermore, FIG. 59 is a flowchart illustrating a procedure for treatment performed using the resectoscope to which the electrode unit of the present embodiment is applied.

FIG. 43 illustrates a state in which the flexed portion 42 functions as a stopper that restricts the electrode 35H from further penetrating into a living tissue, in a case where the electrode 35H is inserted in a living tissue a predetermined amount (length dimension difference amount E) from the distal end, a distal end of the flexed portion 42 of the tissue retaining portion 40H is brought into abutment with a surface of the living tissue and the flexed portion 42 presses the living tissue surface.

In a case where one-piece resection treatment of a living tissue inside an organ 100 is performed using the electrode unit 30H of the present embodiment, first, a user inserts a resectoscope 10 into the organ 100 in a predetermined procedure. Note that, e.g., the procedure for inserting the resectoscope 10 into the organ 100 and a method for filling the inside of the organ 100 with a perfusate are similar to procedures of cases where a conventional resectoscope is used, and thus, description of the procedures will be omitted.

After a distal end portion of the resectoscope 10 being disposed at a predetermined position (position at which a lesion part or the like is located) inside the organ 100, the user inserts the electrode unit 30H through a device channel 10*a* of the resectoscope 10 and performs an operation to make the distal end of the electrode unit 30H project by a predetermined amount from a distal end portion of the device channel toward the outer front side. The operation is also similar to an operation of a conventional resectoscope.

Next, the user brings the electrode unit 30H into a posture in which respective distal ends of the electrode 35H and the flexed portion 42 of the tissue retaining portion 40H face the living tissue that is a treatment target inside the organ 100. Then, the user brings the electrode unit 30H close to a surface of the living tissue with the posture of the electrode unit 30H kept and brings the distal end of the electrode 35H into abutment with a determined position in the vicinity of the treatment target living tissue (living tissue including the lesion part) (step S11 in FIG. 59). At this time, first, the distal end of the electrode 35H is brought into abutment with the tissue surface in a posture in which the electrode 35H and the flexed portion 42 of the tissue retaining portion 40H are as perpendicular to the surface of the living tissue as possible.

Next, the user operates a switch 55*a* to start output of a high-frequency electric current from a high-frequency power supply control device 55. Consequently, the living tissue that is contact with the electrode 35H generates heat and the living tissue is thus cauterized. When cauterization of the living tissue by the electrode 35H is started in this way, as illustrated in FIG. 43, the electrode 35H penetrates into the living tissue. The state at this time is illustrated in FIGS. 42 and 43.

FIGS. 42 and 43 illustrate a state in which the electrode unit 30H projects a predetermined amount from the distal end portion of the resectoscope 10, the distal end of the electrode 35H of the electrode supporting portion 32H of the electrode unit 30H penetrates into the living tissue by a predetermined amount (length dimension difference amount E), and a distal end of the tissue retaining portion 40H presses the surface of the living tissue. FIG. 42 is a schematic diagram of an outer appearance and FIG. 43 is a schematic diagram illustrating a section.

In the state illustrated in FIG. 43, the electrode 35H has penetrated in the living tissue by cauterizing the living tissue. Here, in FIG. 43, the part indicated by cross-hatching and sign 101*a* is the cauterized part.

Generally, as illustrated in FIG. 43, in a living tissue such as an organ, an epithelial layer O, a mucosal layer P, a muscle layer Q and a serosal layer R are formed in the order mentioned from the surface side. When one-piece resection treatment of a living tissue (for example, a living tissue including a lesion part such as a cancer) is performed using the electrode unit 30H of the present embodiment to acquire a desired resected fragment as a pathology specimen, it is necessary to resect the living tissue with the muscle layer Q included, the muscle layer Q being located immediately under the lesion part such a cancer. On the other hand, if the resection extends to a layer under the muscle layer Q, a wall surface of the organ may be perforated. Accordingly, it is desirable to properly and correctly perform resection treatment via the electrode 35H in a stable manner by restricting a depth dimension, in which the electrode 35H penetrates from a living tissue surface, to a predetermined amount.

Therefore, in the electrode unit 30H of the present embodiment, a length dimension of the electrode 35H is set to be longer than a length dimension of the flexed portion 42 of the tissue retaining portion 40H by the length dimension difference amount E. The above configuration of the electrode unit 30H restricts the depth dimension in which the electrode 35H penetrates from a surface of a living tissue, enables proper resection with the muscle layer Q included, and allows resection with no fear of perforation.

For more specific description of the above, as illustrated in FIG. 43, the electrode 35H advances in the arrow Y1 direction in FIG. 43 while cauterizing the living tissue, and penetrates into the tissue. When the distal end of the electrode 35H has reached a predetermined depth, that is, the muscle layer Q in due course, the distal end of the flexed portion 42 of the tissue retaining portion 40H comes into abutment with the surface of the living tissue. Here, the tissue retaining portion 40H comes into abutment with a part in an outer region other than the region cauterized by the electrode 35H.

Therefore, in the electrode unit 30H of the present embodiment, a length of extension in the longitudinal axis L direction of the rod-shaped portion 41 of the tissue retaining portion 40H is longer than a length of extension in the longitudinal axis L direction of the distal end rigid portion 36H by a length dimension difference amount D.

With this configuration, when the electrode 35H cauterizes a living tissue and penetrates into the tissue, the distal end of the flexed portion 42 of the tissue retaining portion 40H comes into abutment with a tissue surface at a position that is away from a region cauterized by the electrode 35H, and presses the tissue surface. However, at this time, the tissue surface that the tissue retaining portion 40H is in abutment with is not cauterized. Accordingly, the tissue retaining portion 40H does not penetrate into the living tissue in this state. Therefore, the tissue retaining portion 40H functions as a stopper that restricts the electrode 35H from penetrating to a depth of a predetermined amount or more in a living tissue.

In the state illustrated in FIG. 43, the electrode 35H can be regarded as being in a stable state in the arrow Y1 direction. In this state, the user performs an operation to make a cut in an outer periphery of a desired region of the living tissue. In the below description, such operation is referred to as "periphery dissection operation". Here, the desired region is a region intended for a resected fragment to be cut off from the living tissue.

Figure 44:
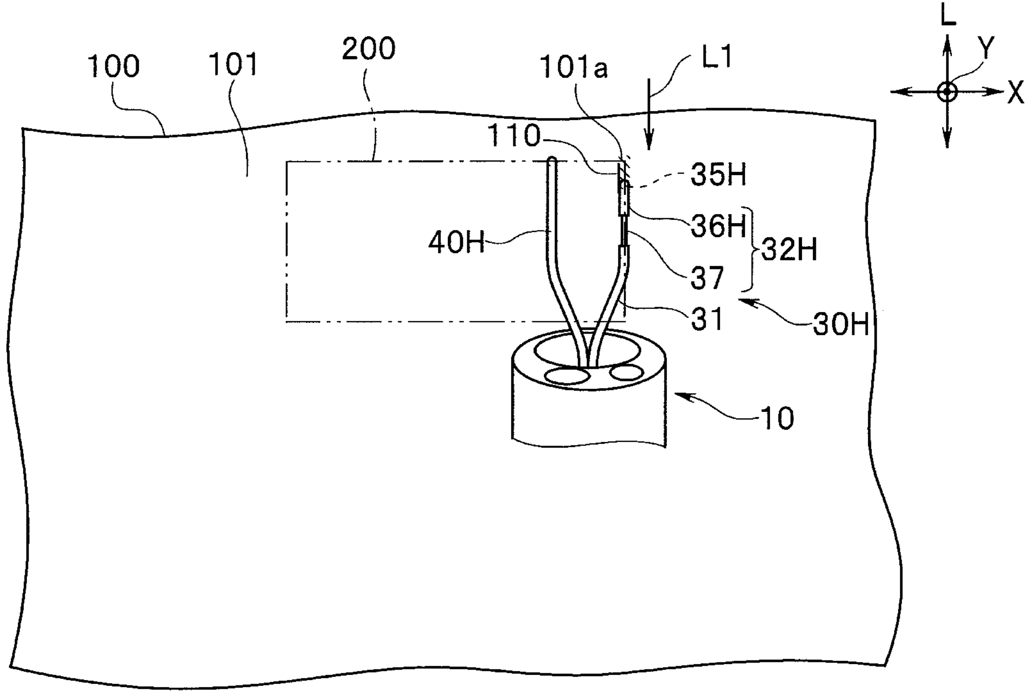
FIG. 44 is a schematic diagram illustrating a state during a first-edge periphery dissection operation in one-piece resection processing via the electrode unit of the second embodiment of the present invention.
Figure 45:
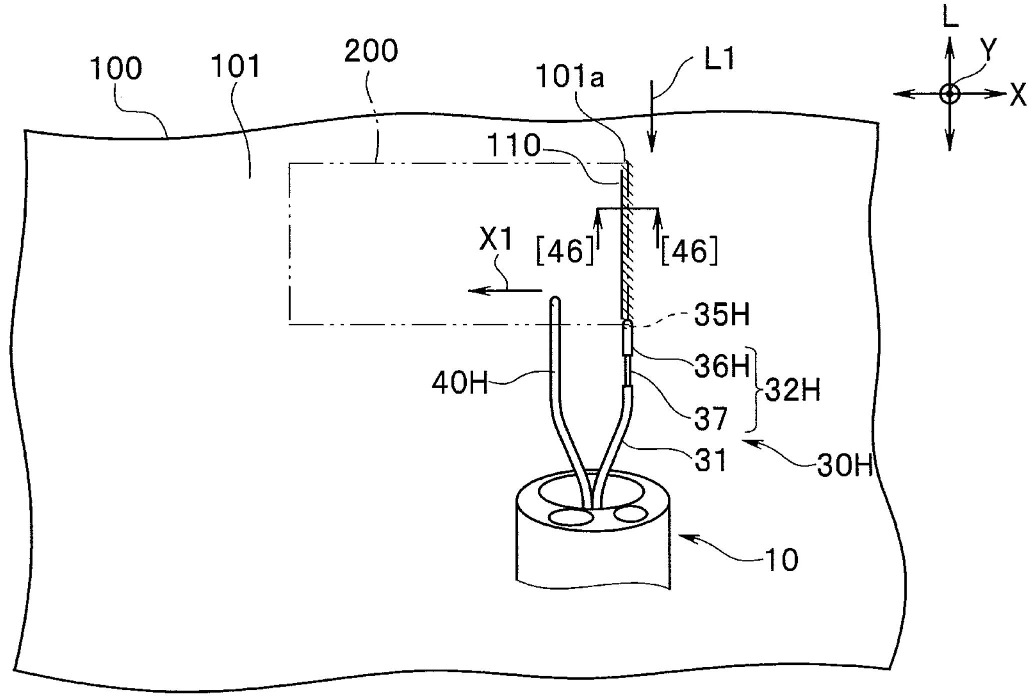
FIG. 45 is a schematic diagram illustrating a state at a time of completion of the first-edge periphery dissection operation after the operation in FIG. 44.
Figure 46:
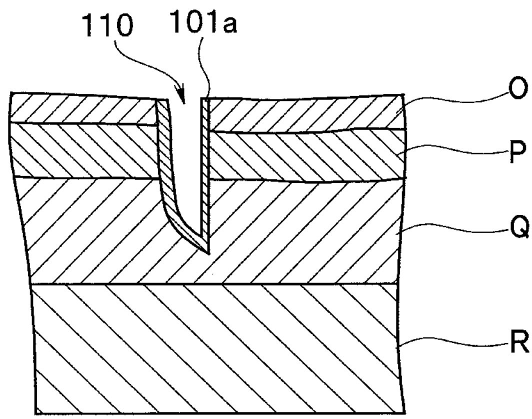

FIGS. 44, 45 and 46 are diagrams illustrating in a state of a periphery dissection operation for a first edge of an outer periphery of an intended region of a living tissue, the intended region being desired to be resected. Of the figures, FIG. 44 is a schematic diagram illustrating a state during a first-edge periphery dissection operation. FIG. 45 is a schematic diagram illustrating a state at a time of completion of the first-edge periphery dissection operation. In FIGS. 44 and 45, the outer periphery of the intended resected region is indicated by alternate long and two short dashes lines and provided with sign 200. FIG. 46 is a schematic diagram illustrating a section along a line [46]-[46] in FIG. 45.

In the first-edge periphery dissection operation, first, in the state illustrated in FIGS. 42 and 43, the user performs an operation to pull the resectoscope 10 to the hand side (proximal end side, that is, the arrow L1 direction in FIGS. 44 and 45) in the direction along the longitudinal axis L together with the electrode unit 30H (step S12 in FIG. 59). Consequently, the electrode supporting portion 32H and the electrode 35H also move in the direction along the longitudinal axis L. At this time, the electrode 35H has penetrated to a predetermined depth dimension in the tissue (see FIG. 43) and a high-frequency electric current is flowing in the electrode 35H. Consequently, the electrode 35H generates a resection groove 110 (see FIG. 46) of the predetermined depth by cauterizing the living tissue. As illustrated in FIG. 46, an inner surface of the resection groove 110 is a cauterized part 101*a*. Note that the resection groove 110 is indicated by a solid line along the cauterized part 101*a* in FIGS. 44 and 45.

When the state in FIG. 45 is thus reached, then, the user performs a second-edge periphery dissection operation (step S13 in FIG. 59). The second-edge periphery dissection operation is an operation to generate a second-edge resection groove 110 that is continuous with the resection groove 110 generated via the first-edge periphery dissection operation and that extends in a predetermined direction substantially orthogonal to the first edge (arrow X1 direction in FIG. 45 in the present example).

Figure 47:
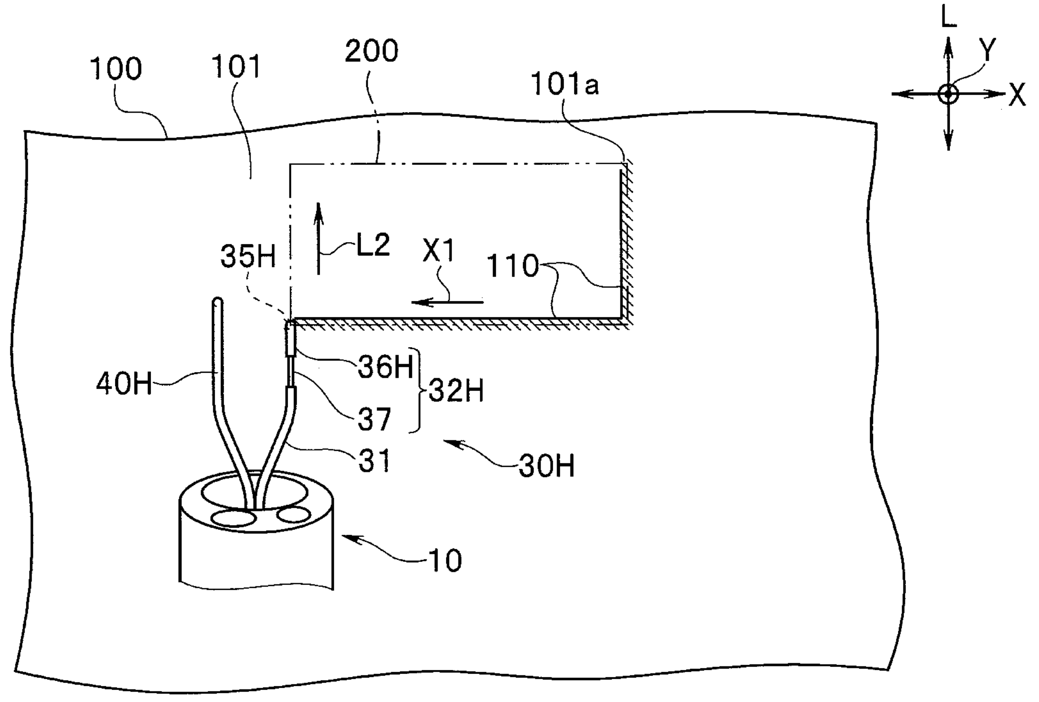
FIG. 47 is a schematic diagram illustrating a state at a time of completion of a second-edge periphery dissection operation.

FIG. 47 is a schematic diagram illustrating a state at a point of time of completion of the second-edge periphery dissection operation in which a second edge of an outer periphery of an intended region of a living tissue, the region being desired to be resected, is subjected to a periphery dissection operation.

In the second-edge periphery dissection operation, in the state illustrated in FIG. 45, the user performs an operation to move the resectoscope 10 in a predetermined direction (arrow X1 direction in FIGS. 45 and 47) orthogonal to the longitudinal axis L together with the electrode unit 30H. Consequently, the electrode supporting portion 32H and the electrode 35H move in the predetermined direction. At this time, also, the electrode 35H has penetrated to the predetermined depth dimension in the tissue and the high-frequency electric current is kept flowing in the electrode 35H. Consequently, the electrode 35H generates a resection groove 110 of the predetermined depth in a manner that is similar to the above, by cauterizing the living tissue.

When the state in FIG. 47 is thus reached, then, the user performs a third-edge periphery dissection operation (step S14 in FIG. 59). The third-edge periphery dissection operation is an operation to generate a third-edge resection groove 110 that is continuous with the second-edge resection groove 110 generated via the second periphery dissection operation and that extends in a predetermined direction (arrow L2 direction in FIG. 47 in the present example) substantially orthogonal to the second edge. Note that a third edge is an edge at a position facing the first side.

Figure 48:
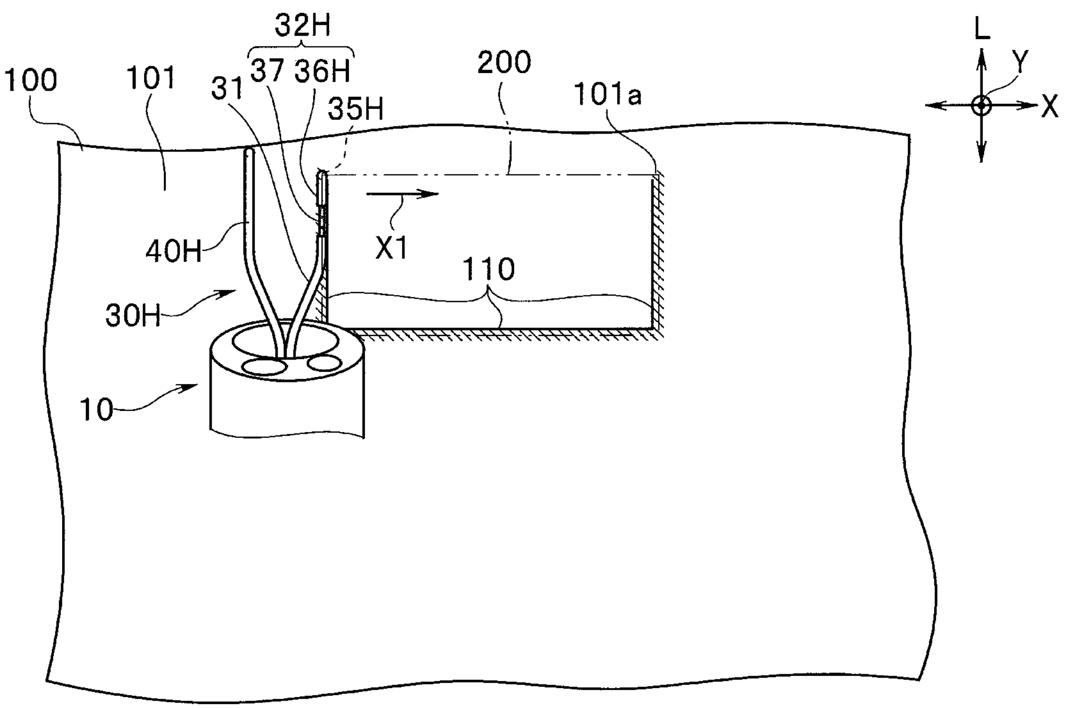
FIG. 48 is a schematic diagram illustrating a state at a time of completion of a third-edge periphery dissection operation.

FIG. 48 is a schematic diagram illustrating a state at a time of completion of the third-edge periphery dissection operation in which the third edge of the outer periphery of the intended region of the living tissue, the region being desired to be resected, is subjected to a periphery dissection operation.

In the third periphery dissection operation, in the state illustrated in FIG. 47, the user performs an operation to push the resectoscope 10 from the hand side (proximal end side) toward the distal end side (arrow L2 direction in FIG. 47) in the direction along the longitudinal axis L together with the electrode unit 30H. Consequently, the electrode supporting portion 32H and the electrode 35H move in the direction along the longitudinal axis L. At this time, also, the electrode 35H has penetrated to the predetermined depth dimension in the tissue and the high-frequency electric current is kept flowing in the electrode 35H. Consequently, the electrode 35H generates a resection groove 110 of the predetermined depth in a manner that is similar to the above, by cauterizing the living tissue.

When the state in FIG. 48 is thus reached, then, the user performs a fourth-edge periphery dissection operation (step S15 in FIG. 59). The fourth-edge periphery dissection operation is an operation to generates a fourth-edge resection groove 110 that is continuous with the resection groove 110 generated via the third periphery dissection operation and that is substantially orthogonal to the third edge (arrow X2 direction in FIG. 48 in the present example). Here, the fourth edge is an edge at a position facing the second edge.

Figure 49:
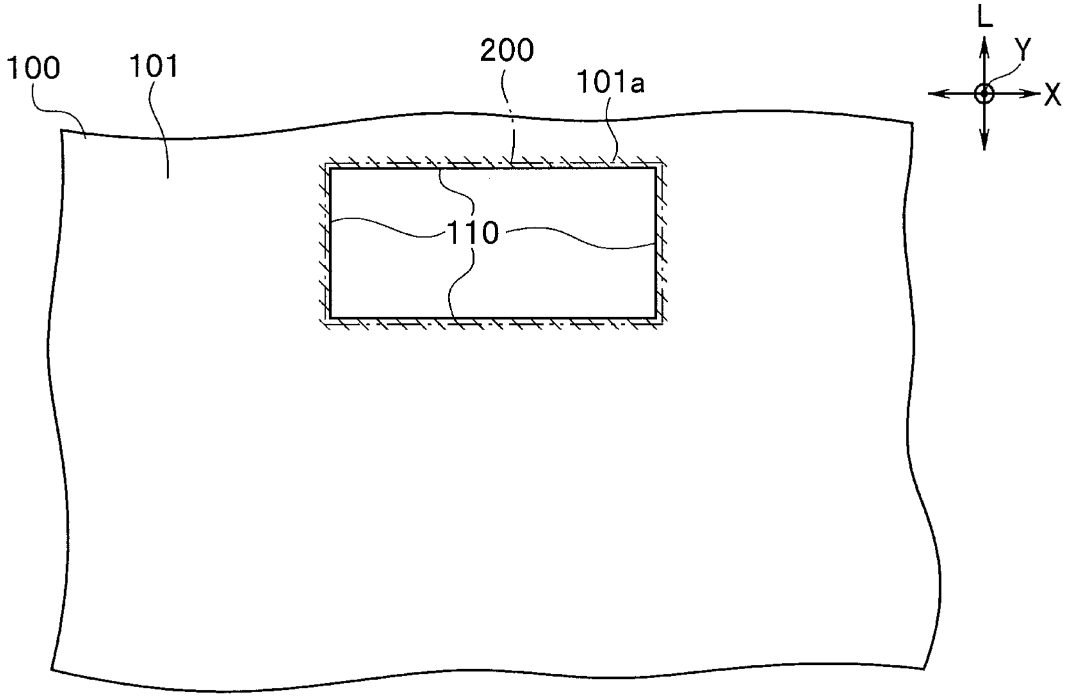
FIG. 49 is a schematic diagram illustrating a resection groove corresponding to an outer periphery of an intended resected region of a living tissue.

When the resectoscope 10 is moved together with the electrode unit 30H to the position indicated in FIG. 45, as illustrated in FIG. 49, a substantially rectangular resection groove 110 is generated. The resection groove 110 indicates an outer periphery of an intended resected region. FIG. 49 is a schematic diagram illustrating a resection groove corresponding to the outer periphery of the intended resected region of the living tissue.

Although in the present embodiment, the outer periphery of the intended resected region has a substantially rectangular shape formed of four edges that are the first to fourth edges (resection grooves 110), the present invention is not limited to this form. Repetition of operations that are similar to the above enables forming an outer periphery of an intended resected region into any shape.

As described above, in one-piece resection processing performed using the electrode unit 30H of the present embodiment, first, a substantially rectangular resection groove 110 corresponding to an outer periphery of an intended resected region of a living tissue is generated. Generating the substantially rectangular resection groove 110 is preparation work for enabling a next fragment detachment operation (operation to detach the intended resected part (resected fragment) in the living tissue from an organ wall surface) to be performed reliably and easily.

In brief, the depth of the substantially rectangular resection groove 110 generated by the above-described periphery dissection operations (operations described with reference to FIGS. 44 to 49) serves as an index for a thickness of the resected fragment, enabling, when the fragment detachment operation is performed, curbing perforation of the wall surface and detaching a fragment in a substantially even thickness. Furthermore, generating a resection groove 110 having a predetermined depth dimension in advance enables, when a fragment detachment operation to be performed subsequently, facilitating an operation to hold a detached resected fragment between the electrode supporting portion 32H and the tissue retaining portion 40H (which will be described later).

Figure 50:
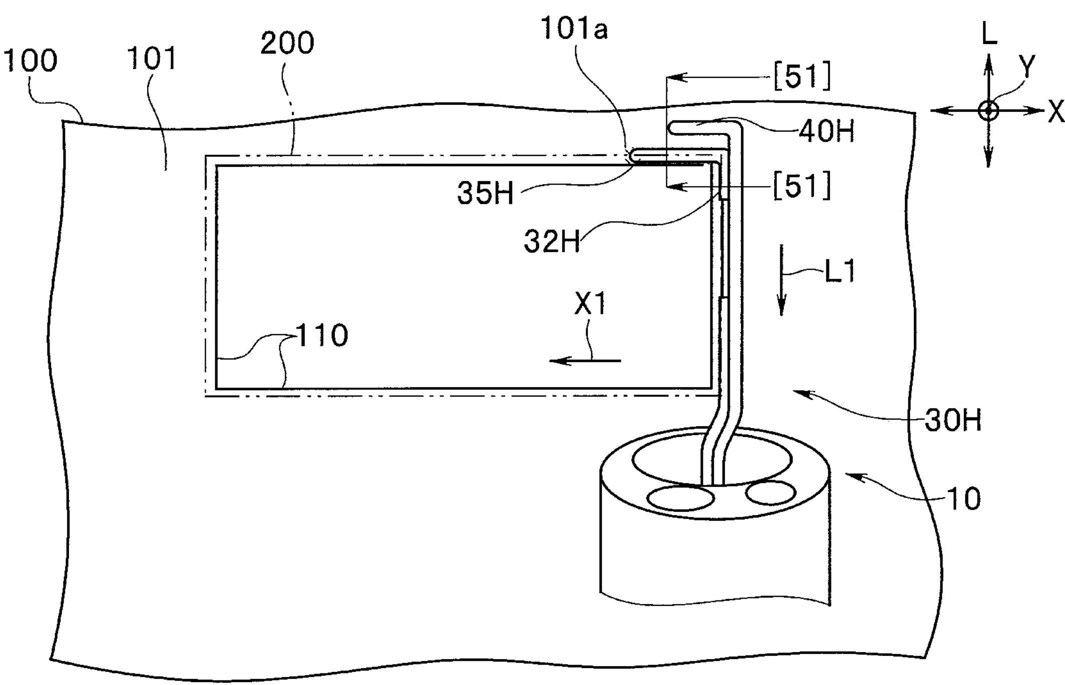
FIG. 50 is a schematic diagram illustrating a disposition of the electrode unit when a first-round fragment detachment operation is started.
Figure 51:
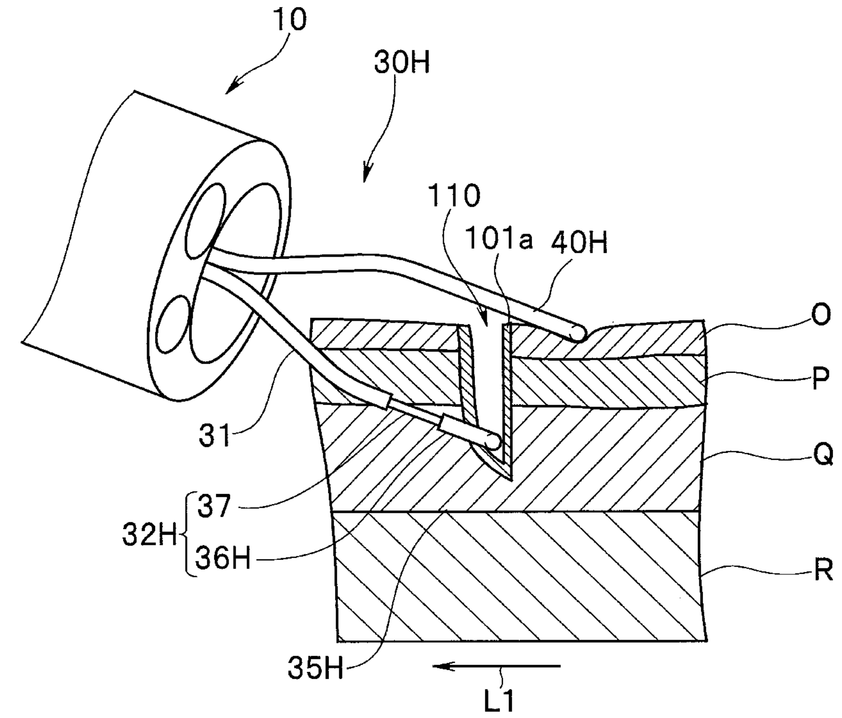
FIG. 51 is a schematic diagram illustrating a section along a line [51]-[51] in FIG. 50.
Figure 52:
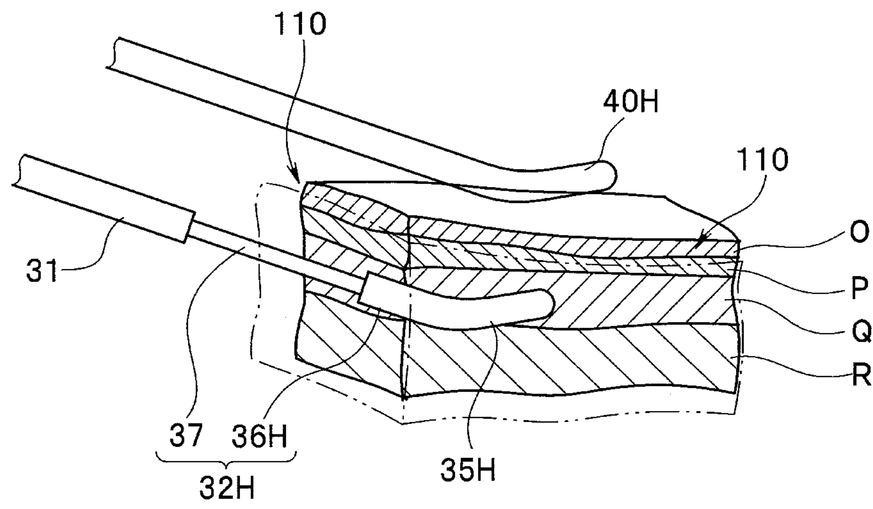
FIG. 52 is a schematic diagram indicating a positional relationship between an electrode and a living tissue in the state in FIG. 51.

Here, a procedure of the fragment detachment operation performed subsequent to the periphery dissection operations will be described below. FIGS. 50, 51 and 52 are diagrams illustrating a state when a fragment detachment operation for an intended region of a living tissue, the region being desired to be resected, is started. Of the figures, FIG. 50 is a schematic diagram illustrating a disposition of an electrode unit when a first-round fragment detachment operation is started. FIG. 51 is a schematic diagram illustrating a section along a line [51]-[51] in FIG. 50. FIG. 52 is a schematic diagram illustrating a positional relationship between an electrode and the living tissue in the state in FIG. 51.

The user disposes the distal end rigid portion 36H of the electrode supporting portion 32H and the electrode 35H of the electrode unit 30H at respective positions illustrated in FIGS. 50 to 52 in the living tissue that is in the state illustrated in FIG. 49. In this case, the electrode 35H and the flexed portion 42 are disposed in parallel with the surface of the living tissue. More specifically, the user rotates the resectoscope 10 with the electrode unit 30H inserted through the device channel by a rotational angle of substantially 90 degrees relative to the state illustrated in FIG. 44. At this time, the electrode 35H and the flexed portion 42 are disposed so as to extend in the arrow X1 direction in FIG. 45.

Furthermore, the distal end rigid portion 36H of the electrode supporting portion 32H is aligned with a resection groove 110 extending in the longitudinal axis L direction, the electrode 35H is aligned with a resection groove 110 extending in a direction orthogonal to the longitudinal axis L direction, and then the electrode 35H is disposed on a bottom portion in the depth direction of the resection groove 110. In brief, the distal end rigid portion 36H and the electrode 35H are disposed on the bottom portions inside the grooves so as to fit in the upper right corner between the resection grooves 110 in FIG. 49 (step S16 in FIG. 59). In this state, a high-frequency electric current is made to flow in the electrode 35H.

Then, the user performs an operation to pull the resectoscope 10 to the hand side (proximal end side, that is, the arrow L1 direction in FIG. 50) in the direction along the longitudinal axis L together with the electrode unit 30H (step S17 in FIG. 59). Consequently, the electrode 35H also moves in the arrow L1 direction. Then, the electrode 35H detaches a region of the living tissue, the region corresponding to a width dimension of the electrode 35H itself, in the form of a tissue fragment having a predetermined constant thickness. The operation at this time is substantially the same as the first-round dissection operation in the above-described operation procedure in the first embodiment.

Figure 53:
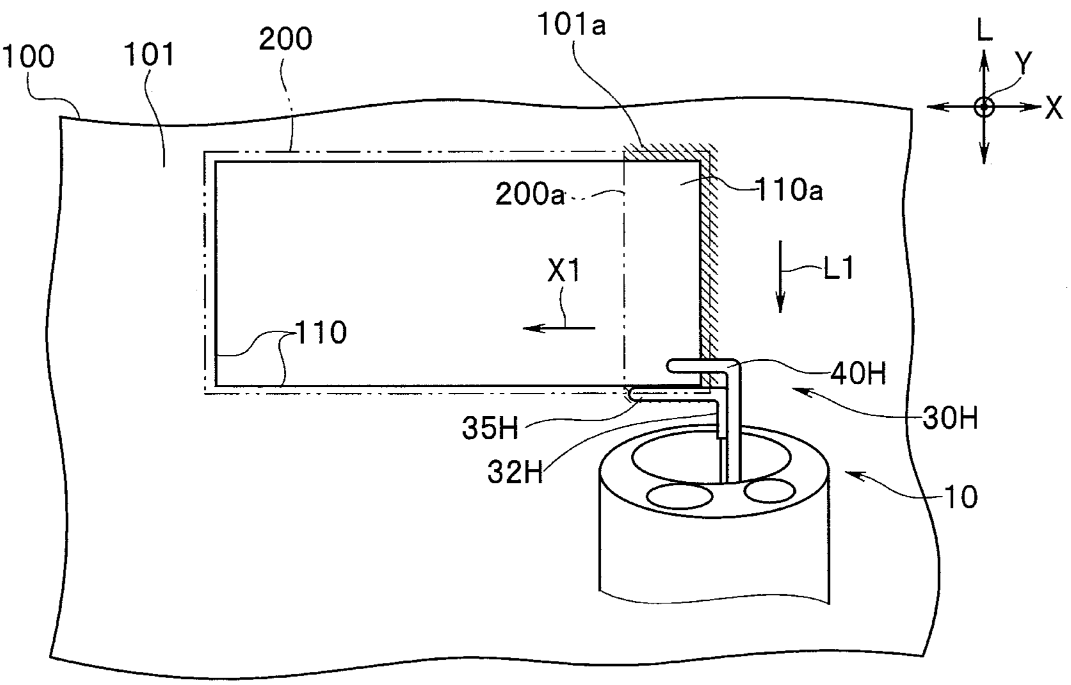
FIG. 53 is a schematic diagram illustrating a state in which the electrode has reached a detachment end position as a result of the first-round fragment detachment operation being performed.

FIG. 53 is a schematic diagram illustrating the electrode that has reached a detachment end position as a result of the first-round fragment detachment operation being performed. In this state, a detached fragment, a part of the detached fragment sticking to the living tissue surface, has been created (step S18 in FIG. 59). In FIG. 53, sign 200*a* indicated by an alternate long and two short dashes line denotes a resection straight line of a fragment 110*a* detached via the first-round fragment detachment operation.

Figure 54:
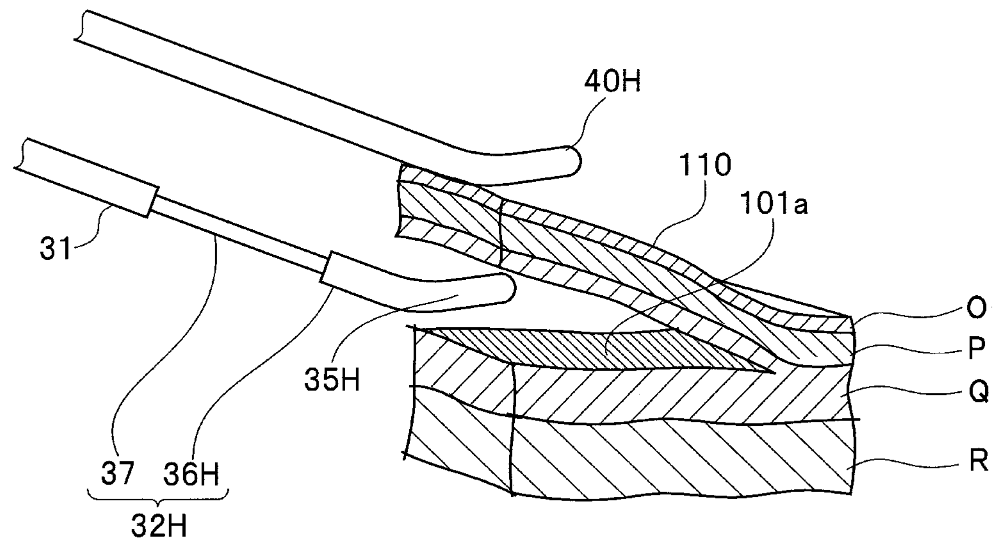
FIG. 54 is a schematic diagram illustrating a state when the electrode is moved from the detachment end position of the first-round fragment detachment operation to a start position of a second-round fragment detachment operation, with a partial section of a living tissue.
Figure 55:
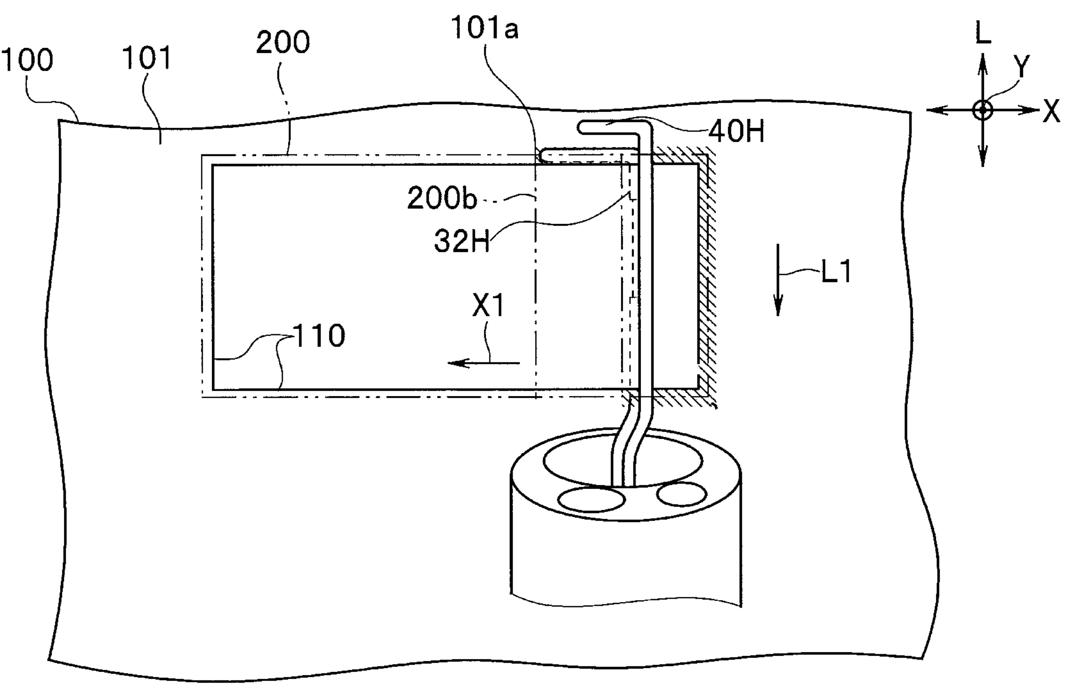
FIG. 55 is a schematic diagram illustrating a disposition of the electrode unit when the second-round fragment detachment operation is started.

FIG. 54 is a schematic diagram illustrating a state when the electrode is moved from the detachment end position in the first-round fragment detachment operation in FIG. 53 to a start position of a second-round fragment detachment operation, with a partial section of the living tissue. FIG. 55 is a schematic diagram illustrating a disposition of the electrode unit when the second-round fragment detachment operation is started.

As illustrated in FIG. 53, when the electrode 35 has reached the detachment end position as described above, the application of the high-frequency electric current to the electrode 35H is stopped, and then, as illustrated in FIG. 54, the electrode 35H with no electric current applied is moved away from the cauterized surface and is returned to the position indicated in FIG. 50 while the detached part is lifted to the upper side by the electrode 35H.

Furthermore, the electrode 35H is moved in the arrow X1 direction inside the resection groove 110 and disposed at a start position of a next second-round detachment operation (position indicated in FIG. 55) (step S19 in FIG. 59). At this time, the fragment 110*a* detached via the first-round fragment detachment operation is maintained so as to be held between the electrode 35H and the distal end rigid portion 36H, and the tissue retaining portion 40H. Furthermore, during fragment detachment operations of the next time onwards being performed, also, the detached fragment 110*a* is consistently held between the electrode 35H and the distal end rigid portion 36H, and the tissue retaining portion 40H. Consequently, the tissue retaining portion 40H prevents the detached fragment 110*a* from being turned up during a detachment operation being performed, enabling the detachment operation to be performed smoothly.

Then, a high-frequency electric current is applied again to the electrode 35H returned to the state in FIG. 55. An operation that is similar to the first-round fragment detachment operation is repeated until the resulting living tissue fragment is separated off from the living tissue (looped processing in steps S17 to 20 in FIG. 59).

Figure 56:
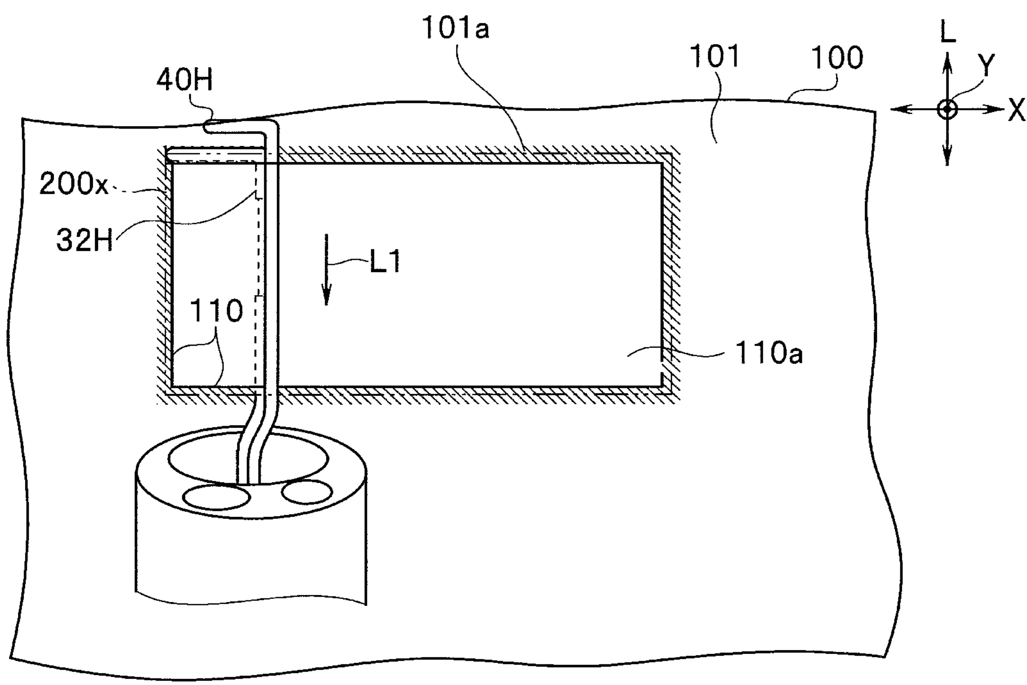
FIG. 56 is a plan view of a disposition of the electrode unit when a final-round fragment detachment operation is started, from the upper side.
Figure 57:
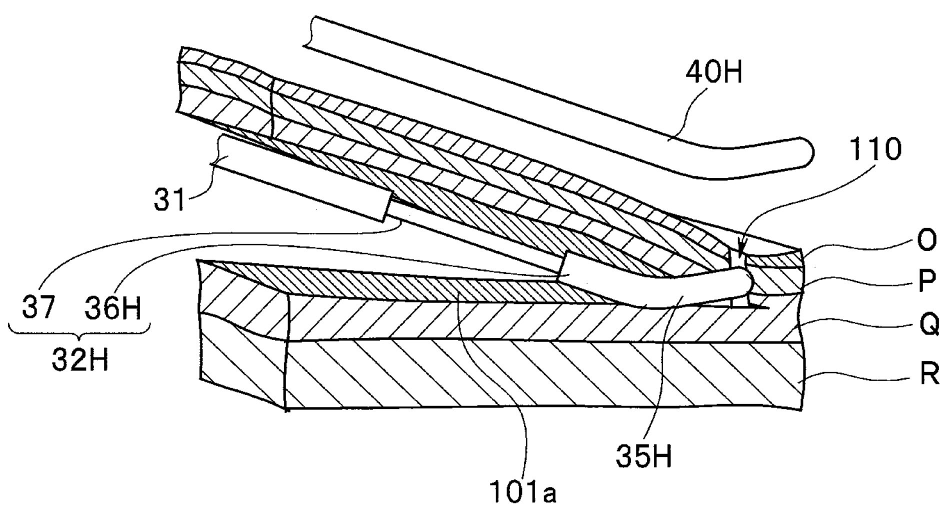
FIG. 57 is a partial cross-sectional view of a living tissue in the state in FIG. 56.

After the above-described fragment detachment operation is repeated a plurality of times, as illustrated in FIGS. 56 and 57, the electrode 35H is disposed at a start position of a final-round fragment detachment operation. FIGS. 56 and 57 are schematic diagrams illustrating a disposition of the electrode unit when the final-round fragment detachment operation is started. FIG. 56 is a plan view of the electrode unit from the upper side and FIG. 57 is a partial cross-sectional view of the living tissue.

As illustrated in FIG. 56, in the final-round fragment detachment operation, the distal end of the electrode 35H is disposed so as to project into a resection groove 110. In this state, the electrode 35H to which a high-frequency electric current is applied is moved in the arrow L1 direction. Then, when the electrode 35H has reached the detachment end position, the resection treatment-target living tissue fragment (living tissue including the lesion part such as a cancer) is separated off from a wall surface 101 of the organ 100 (step S20 in FIG. 59). Consequently, one-piece resection processing via the electrode unit 30H of the present embodiment is completed.

Here, during an operation to detach the final fragment 110*a* being performed, the previously detached part of the fragment 110*a* is maintained so as to be held between the electrode 35H and the distal end rigid portion 36H, and the tissue retaining portion 40H until completion of the detachment.

In this case, since the length in the longitudinal axis L direction of the tissue retaining portion 40H is set to be longer than the length in the longitudinal axis L direction of the distal end rigid portion 36H by the length dimension difference amount D, when the detachment operation in the arrow L direction reaches the end position, the electrode 35H and the distal end rigid portion 36H are disposed at respective positions outside the previously detached part of the fragment 110*a*, but the tissue retaining portion 40H is consistently kept retaining the previously detached part of the fragment 110*a*. Therefore, no trouble of re-catching the previously detached part of the fragment 110*a* between the electrode 35H and the distal end rigid portion 36H, and the tissue retaining portion 40H is needed.

As described above, according to the second embodiment, a resection groove 110 having a predetermined depth dimension is created in advance, and thus, it is possible to during an operation to perform one-piece resection processing of a living tissue being performed, complete treatment with no need for a difficult operation to turn up the previously detached part of the fragment 110*a*.

Furthermore, in the configuration of the present embodiment, in one-piece resection processing of a living tissue, the tissue retaining portion 40H consistently retains a previously detached part of a fragment 110*a*, preventing problems of, e.g., the previously detached part of the fragment 110*a* being caught in the periphery of the device during the operation for treatment and thus enabling always easily acquiring the resected fragment as a pathology specimen of a desired form.

It should be understood that the present invention is not limited to the respective embodiments described above and various modifications and application are possible without departing from the gist of the invention. Furthermore, each of the above-described embodiments includes various phases of invention, and various aspects of the invention can be extracted by appropriate combinations of a plurality of elements disclosed. For example, for each of the embodiments, even in a case where some elements are deleted from all the elements indicated in the embodiment, a configuration with such elements deleted may be extracted as an aspect of the invention if such configuration can solve a problem to be solved by the invention and provide an effect of the invention. Furthermore, elements in different embodiments may appropriately be combined. This invention is not restricted by any particular embodiment except for being limited by the accompanying claims.

What is claimed is:

1. An electrode unit comprising:

a cantilevered electrode including a first end and an unsupported second end;

an electrode support that supports the first end of the electrode, the electrode support extending along a longitudinal axis direction; and an arm disposed at a position at which the arm faces the electrode support, such that the electrode is interposed between the arm and the electrode support, the arm being configured to retain a surface of a tissue;

wherein an entirety of the electrode extends in a direction offset from the longitudinal axis direction;

the electrode directly extends from a side surface of the electrode support; and the electrode extends from the electrode support towards the arm.

2. The electrode unit according to claim 1, wherein the arm has a rod shape, an outer surface of the arm includes a material having an electrical insulating property, such that the electrode is interposed between the arm and the electrode support.

3. The electrode unit according to claim 1, wherein the arm extends on a far end side relative to a distal end of the electrode support.

4. The electrode unit according to claim 1, wherein the electrode has a first portion exposed from the electrode support directly extending from the electrode support and a second portion exposed from the electrode support bent relative to the first portion.

5. The electrode unit according to claim 4, wherein the second portion of the electrode is bent in one of an upward projecting shape or a downward projecting shape relative to the first portion.

6. The electrode unit according to claim 5, wherein the upward projecting shape is a curved upward bending shape.

7. The electrode unit according to claim 5, wherein the downward projecting shape is a curved downward projecting shape.

8. The electrode unit according to claim 1, wherein the electrode includes a surface with an insulating coating.

9. The electrode unit according to claim 1, further comprising a plate having one end supported by the electrode support, the plate extending in parallel with a direction in which the electrode extends.

10. The electrode unit according to claim 1, wherein the electrode extends in a direction offset from the longitudinal axis direction and is disposed in a second plane different from a first plane in which the electrode support is moved to advance or withdraw when the electrode support is moved to advance or withdraw in a direction along a longitudinal axis direction of the electrode support; and the first plane and the second plane are parallel to each other.

11. The electrode unit according to claim 10, wherein the electrode is supported by the electrode support via a flexed portion projecting from the first plane to the second plane.

12. The electrode unit according to claim 1, wherein a distal end of the electrode support and a distal end of the arm are disposed in parallel with each other.

13. The electrode unit according to claim 1, wherein the electrode support comprises a rigid portion and an elastic portion that has a lower rigidity than the rigid portion; and the rigid portion is disposed distally relative to the elastic portion.

14. The electrode unit according to claim 1, wherein the arm faces the electrode support and the electrode is between the arm and the electrode support.

15. A treatment system comprising:

an endoscope including an insertion portion; and the electrode unit according to claim 1 that projects from a distal end of the insertion portion.

* * * * *